US012661651B2

(12) United States Patent
Xie et al.

(10) Patent No.: US 12,661,651 B2
(45) Date of Patent: Jun. 23, 2026

(54) NUCLEIC ACID EXTRACTION DEVICE

(71) Applicant: Hangzhou Bigfish Bio-tech Co., Ltd., Hangzhou City (CN)

(72) Inventors: Lianyi Xie, Hangzhou City (CN); Ming Li, Hangzhou City (CN); Peng Wang, Hangzhou City (CN); Ning Chen, Hangzhou City (CN); Guojun Tong, Hangzhou City (CN); Jin Hu, Hangzhou City (CN); Zhuo Tan, Hangzhou City (CN); Wenyu Ren, Hangzhou City (CN); Xiaojuan Xu, Hangzhou City (CN)

(73) Assignee: HANGZHOU BIGFISH BIO-TECH CO., LTD., Hangzhou City (CN)

( * ) Notice: Subject to any disclaimer, the term of this patent is extended or adjusted under 35 U.S.C. 154(b) by 661 days.

(21) Appl. No.: 17/980,069

(22) Filed: Nov. 3, 2022

(65) Prior Publication Data

US 2023/0135264 A1 May 4, 2023

(30) Foreign Application Priority Data

Nov. 3, 2021 (CN) .......................... 202111293592.7
Sep. 27, 2022 (CN) .......................... 202211183647.3

(51) Int. Cl.
*B01L 3/00* (2006.01)
*C12N 15/10* (2006.01)
(Continued)

(52) U.S. Cl.
CPC .... *B01L 3/502761* (2013.01); *C12N 15/1013* (2013.01); *C12Q 1/6844* (2013.01); *G01N 35/1011* (2013.01); *B01L 2200/0652*
(2013.01); *B01L 2200/0668* (2013.01); *B01L 2200/10* (2013.01); *B01L 2300/0645* (2013.01); *B01L 2300/0861* (2013.01); *B01L 2400/0478* (2013.01); *B01L 2400/0644* (2013.01); *G01N 2035/1034* (2013.01)

(58) Field of Classification Search
CPC ....... B01L 3/502761; B01L 2200/0652; B01L 2200/0668; B01L 2200/10; B01L 2300/0645; B01L 2300/0861; B01L 2400/0478; B01L 2400/0644; B01L 2300/0809; B01L 2400/0622; B01L 3/502; C12N 15/1013; C12Q 1/6844; G01N 35/1011; G01N 2035/1034
See application file for complete search history.

(56) References Cited

U.S. PATENT DOCUMENTS

2010/0262389 A1* 10/2010 Nakanishi ................. H02P 5/60
 702/56
2014/0099646 A1* 4/2014 Connolly ............... C12M 47/06
 435/6.12
2024/0390886 A1* 11/2024 Hirsch .................... B01L 3/502

* cited by examiner

*Primary Examiner* — Benjamin R Whatley
(74) *Attorney, Agent, or Firm* — MUNCY, GEISSLER, OLDS & LOWE, P.C.

(57) ABSTRACT

Provided herein is a nucleic acid extraction and the structure of a reaction chamber is improved such that a piston, a reaction chamber and a magnetic rod are independent of one another, magnetic beads are more concentrated, more sufficient adsorption, washing and elution are achieved, dead corners are eliminated, when the nucleic acid extraction and amplification device is used to perform nucleic acid extraction and amplification. The sensitivity and accuracy of nucleic acid detection can be further improved, and missing and wrong detection can be avoided.

17 Claims, 37 Drawing Sheets

(51) Int. Cl.
    *C12Q 1/6844*        (2018.01)
    *G01N 35/10*         (2006.01)

22

7

4

1

5

2

3

8

6

11    10

42

43                                           47

40

44

36

45

48                                            46

40

47

43

First state

Second state

Fourth state

Third state (1)                    (2)

(1)                                      (2)

(2)

104

122

123

113

105

112

118

103

113

111

120

112

119

118

103

(1)                                    (2)

NUCLEIC ACID EXTRACTION DEVICE

CROSS-REFERENCE TO RELATED APPLICATIONS

The present application claims priority to a Chinese prior application No. 2021112935927 and filed on Nov. 3, 2021, and a Chinese prior provisional application No. 2022111836473 and filed on Sep. 21, 2022; the entire contents of the two patent applications, including but not limited to the description, accompanying drawings, claims and abstract of which are incorporated herein as a portion of the present invention.

TECHNICAL FIELD

The disclosure belongs to the field of biological detection, and relates to a nucleic acid detection device, in particular to a nucleic acid extraction and amplification device.

BACKGROUND OF THE INVENTION

Nucleic acids are the basis of molecular biology studies, and high-quality nucleic acids are prerequisites for molecular marker, gene cloning and gene expression studies. Since biological samples (for example, blood, saliva, semen or other secretions) have complex composition, target nucleic acids therein usually need to be extracted, purified and amplified before follow-up studies can be carried out. At present, the existing nucleic acid extraction and amplification mainly have the following problems: (1) in the face of a huge number of complex sample processing, nucleic acid extraction, purification and amplification steps, manual operation is prone to errors, and the overall operation steps are complex, which makes it impossible to perform efficient and rapid extraction and amplification of the target nucleic acids; (2) most molecular diagnosis needs to be carried out in laboratories, but many grassroots units do not have the conditions to establish standard molecular diagnosis laboratories, and in addition, different operators have different operation habits and proficiency levels, so that the nucleic acids are prone to cross contamination of samples in the process of extraction and amplification; and (3) existing nucleic acid extraction instruments and polymerase chain reaction (PCR) instruments are often bulky and not suitable for use in sampling sites, which limits the application range of molecular diagnosis to a certain extent. The full-automatic, totally-enclosed and integrated operation of nucleic acid extraction and amplification can shorten the process of nucleic acid extraction and amplification, reduce the impact of human factors, enhance the safety and effectiveness of nucleic acid sample preparation, and meet the requirements of miniaturization and portability of devices that meet the needs of grassroots or on-site rapid detection, which is the main study direction for developing new nucleic acid extractors.

Since consumables for nucleic acid extraction and purification are usually disposable articles, the nucleic acid extractors need to dock with the disposable consumables by means of piston-related assemblies; however, the existing nucleic acid extractors are generally manually combined with the consumables for use and separated after use, and the manual operation affects the efficiency of nucleic acid extraction and reduces the automation level, so that there is an urgent need for a device capable of automatically combining and separating a nucleic acid extractor and consumables.

The existing consumables for nucleic acid extraction and purification are of complex structures and are generally provided with relatively large chambers for accommodating waste liquid generated after reaction or washing; meanwhile, nucleic acid amplification portions generally adopt the relatively complex designs, which mainly aim to ensure the sealing effect while said portions can be disassembled and transferred to other devices for heating; in addition, only one nucleic acid can be amplified at a time, and when there are multiple items, multiple operations are required, which consumes a lot of time.

In the process of nucleic acid extraction and amplification by the nucleic acid extractors, it is necessary to drive channel turntables thereof to rotate accurately as per preset rotation angles and drive pistons thereof to move vertically. Therefore, in order to achieve full automation, the nucleic acid extractors must also be equipped with motor driving devices of complex and precise structures, which is expensive and can hardly meet the requirements for miniaturization and portability. In addition, there are no relevant reports on the nucleic acid extractors that can achieve the full-automatic, totally-enclosed and integrated operation of nucleic acid extraction, amplification and detection.

Therefore, there is an urgent need for a nucleic acid extraction and amplification device which can achieve integration of nucleic acid extraction, amplification, detection and analysis, is of a simple structure, has a small size, has the high automation level and can detect multiple items at the same time.

SUMMARY OF THE INVENTION

In order to solve the above-mentioned problems, the disclosure provides a nucleic acid extraction and amplification device. The structure of a reaction chamber is improved such that a piston, the reaction chamber and a magnetic rod are independent of one another, magnetic beads are more concentrated, more sufficient adsorption, washing and elution are achieved, dead corners are eliminated, when the nucleic acid extraction and amplification device is used to perform nucleic acid extraction and amplification, the sensitivity and accuracy of nucleic acid detection can be further improved, and missing and wrong detection can be avoided. In addition, a piston driving mechanism is provided to successfully achieve the automatic combination and separation of the piston and a driving mechanism, to achieve the vertical movement of the piston, to increase the automation level of a nucleic acid extractor, to make a nucleic acid extraction experiment more convenient, and to improve the efficiency of the nucleic acid extraction. By means of a nucleic acid extraction and detection integrated machine in the disclosure, the full-automatic, totally-enclosed and integrated operation of nucleic acid extraction, amplification, detection and analysis can be really achieved, and the machine is of a simple structure, has a small size, has the high automation level, can detect multiple items at the same time and particularly meets the needs of grassroots or on-site rapid detection.

In one aspect, the disclosure provides the nucleic acid extraction and detection integrated machine, comprising the nucleic acid extraction and amplification device and a driving component, wherein the nucleic acid extraction and amplification device is configured to extract, purify and amplify nucleic acids in samples; the driving component is configured to carry and drive the nucleic acid extraction and amplification device to operate, and comprises the piston driving mechanism and a worm gear and worm transmission mechanism; the piston driving mechanism is configured to drive the piston in the nucleic acid extraction and amplification device to move vertically; the worm gear and worm transmission mechanism is configured to drive a channel turntable to rotate, thereby connecting and disconnecting different chambers of the nucleic acid extraction and amplification device; and the worm gear and worm transmission mechanism is provided with an elastic element capable of resetting, which is configured to provide thrust for a worm shaft to make a worm close to a worm gear so as to eliminate a backlash.

In order to achieve the full-automatic, totally-enclosed and integrated operation of nucleic acid extraction and amplification, it is necessary to drive the channel turntable of the nucleic acid extraction and detection integrated machine to rotate accurately as per a preset rotation angle at the specified time, so as to ensure that a micro-channel in the nucleic acid extraction and detection integrated machine is connected precisely when needed and disconnected accurately when needed according to working program settings. The micro-channel in the nucleic acid extraction and detection integrated machine is very narrow, if there is a little error in the rotation angle or the rotation time of the channel turntable, the micro-channel may not be connected at the specified time, and thus the nucleic acid extraction or amplification process is interrupted and cannot be carried out normally; therefore, the driving mechanism must be used to achieve the precision control to ensure that the channel turntable rotates accurately as per the preset angle each time without any error. At the same time, the channel turntable has a relatively slow rotation speed and rotates at low speed and low load, and the accurate control on the rotation angle can only be achieved by a transmission device that is most suitable for the low speed and low load and can achieve high-precision transmission. It can be seen that in order to achieve full automation of nucleic acid extraction and amplification, a motor of a complex and precise structure must be adopted by the nucleic acid extraction and detection integrated machine to drive the channel turntable to rotate; however, a complex and precise driving apparatus is usually expensive and can hardly meet the requirements for miniaturization and portability.

Micro-pores and the micro-channel have the apertures of 600 microns. According to working program settings, the disclosure must realize the operation that the channel turntable rotates by 35-151 degrees accurately each time it needs to be connected, so as to be connected to the different chambers in the nucleic acid extractor, and maintain stability without liquid leakage. Moreover, the channel turntable is simple in structure, low in cost and convenient to install, debug and maintain, and is particularly suitable for the miniaturized and portable nucleic acid extraction and detection integrated machine.

In order to achieve the accurate control on the rotation angle of the channel turntable in the nucleic acid extraction and detection integrated machine, a device capable of achieving high-precision transmission at low speed and low load is needed, and the device is required to be simple in structure, low in cost and convenient to install, debug and maintain. The improved worm gear and worm transmission mechanism is adopted in the disclosure, so as to achieve the accurate control on the rotation angle of the channel turntable of the nucleic acid extraction and detection integrated machine in a way of simpler structure and lower cost.

Further, the elastic element capable of resetting is a reset spring, the reset spring is located at a first end of the worm shaft, and a second end of the worm shaft is flexibly fixed by means of an angular contact bearing.

Further, one reset spring is provided, a first end of the reset spring is movably connected to the worm shaft by means of a connecting module, and the connecting module is provided with an arc-shaped recess and is in direct contact with the worm shaft by means of the arc-shaped recess, so that the worm shaft will not be affected by the friction force during rotation.

In some embodiments, the arc-shaped recess in the connecting module is a semi-circular recess, which is convenient to connect and remove.

Further, the connecting module is made of lubricating materials, and the arc-shaped recess is provided with an arc-shaped rib which matches with an arc-shaped groove in the worm shaft.

In some embodiments, the arc-shaped groove is provided at the end of the worm shaft, the arc-shaped rib on the arc-shaped recess matches with the arc-shaped groove in the worm shaft, thus the connecting module can be further fixed, thereby preventing the left-and-right displacement from affecting the anti-backlash effect.

Further, the connecting module is made of POM (poly-oxymethylene/polyformaldehyde) or Teflon (polytetrafluoroethylene) materials.

In some embodiments, the connecting module of the disclosure is made of self-lubrication material POM which is lower in price, thus free rotation of the worm shaft can be achieved without adding lubricating oil and the like in the use process, the worm shaft will not be affected by the friction force in the rotation process, and the wear is reduced as much as possible.

Further, a second end of the reset spring is fixed to a base, and the reset spring has an elastic modulus of 0.5-1.0 $N/m^2$.

In some embodiments, the elasticity of the reset spring can be calculated according to the driving force required to drive the worm gear and the worm for gapless transmission; the excessively high elasticity of the reset spring will result in increase of the rotating friction force of the worm shaft and reduction of the rotation speed, which affects the transmission accuracy; and the excessively low elastic modulus of the reset spring will result in reduction of the anti-backlash effect of the worm gear and the worm, which also affects the transmission accuracy. The elasticity of the reset spring required by the nucleic acid extractor of the disclosure needs to reach 3-5 N, at this moment, the elastic modulus is 0.5-1.0 $N/m^2$, the transmission accuracy is high, the anti-backlash effect of the worm gear and the worm is optimal, and the rotation angle of the channel turntable in the nucleic acid extractor can be accurately controlled at the specified time.

Further, the worm gear and worm transmission mechanism comprises the worm gear, a worm gear shaft, the worm, the worm shaft, a worm gear and worm anti-backlash mechanism including the reset spring, and a bracket configured to fix the worm gear, the worm and the worm gear and worm anti-backlash mechanism.

In some embodiments, the worm is locked on the worm shaft by means of a set screw, and the worm gear is locked on the worm gear shaft by means of a set screw.

Further, the angular contact bearing is pressed into the bracket in a shrink-fit manner, and the second end of the worm shaft is locked on the angular contact bearing by means of a lock nut; and the base of the reset spring is fixed to the bracket.

In some embodiments, the angular contact bearing can also be fixed to the bracket by pressing two sides of the angular contact bearing by means of bearing end caps, and then is further fixed by means of screws.

Further, the motor is further included and can drive a motor shaft to rotate; the worm shaft is connected to the motor shaft by means of a coupling; and the coupling is a diaphragm coupling having flexibility.

The motor drives the motor shaft to rotate, and the motor shaft drives, in a high-precision and rotation-gap-free manner, the worm shaft to rotate by means of the diaphragm coupling.

Further, the nucleic acid extraction and amplification device comprises the piston, the reaction chamber and a permanent magnet, wherein the piston is configured to control the flow direction of a fluid in the nucleic acid extraction and amplification device; the reaction chamber is configured to provide a place for the magnetic beads to adsorb, wash and elute nucleic acids; the permanent magnet is configured to provide a magnetic attraction force for the magnetic beads; and the piston is located inside or outside the reaction chamber.

The nucleic acid extraction and amplification device of the disclosure is a disposable consumable (hereinafter referred to as the consumable) used in the nucleic acid extraction and detection integrated machine, is made of plastics and other materials, is configured to help the nucleic acid extraction and detection integrated machine to achieve the extraction, purification and amplification of the nucleic acids, mainly changes the air pressure in each area of the consumable and controls the flow direction of the fluid in the consumable by means of the pumping and suction force generated by driving the piston to perform vertical pumping and suction movements, and cooperates with the vertical movement of the magnetic rod to control the positions of the magnetic beads, so as to complete the adsorption of the nucleic acids, the washing of the magnetic beads, and the elution of the nucleic acids in the consumable (mainly the reaction chamber). The magnetic rod, a magnetic rod driving device and the piston driving device thereof are reusable and are not disposable consumables. Therefore, in order to improve the nucleic acid detection sensitivity and accuracy of the nucleic acid extraction and detection integrated machine, the nucleic acid extraction and purification in the consumable must be fully and thoroughly completed.

Further, when the piston is located inside the reaction chamber, the reaction chamber is internally provided with the piston and a hollow accommodating chamber; the hollow accommodating chamber is configured to accommodate the permanent magnet, the piston is a hollow cylinder, and the hollow cylinder in the piston has the diameter matching that of the hollow accommodating chamber, so that the piston can be sleeved outside the hollow accommodating chamber and move vertically along an outer wall of the hollow accommodating chamber; the displacement of the piston causes the pressure change, thereby promoting the fluids to flow between the reaction chamber and other chambers; and the permanent magnet is the magnetic rod.

Further, when the piston is located inside the reaction chamber, the piston driving mechanism comprises a piston rod, a combined movement assembly and a separated movement assembly; the combined movement assembly can combine the piston with the piston rod, thereby enabling the piston rod to drive the piston to move vertically; and the separated movement assembly prevents the piston from moving by ejecting a push rod, thereby enabling the piston to be separated from the piston rod that moves continuously.

The nucleic acid extraction and detection integrated machine also needs to achieve the extraction, purification and amplification of the nucleic acids by means of the disposable consumable, a piston pushing rod (hereinafter referred to as the piston rod) in the nucleic acid extractor is mainly configured to drive the piston in the consumable to perform the vertical pumping and suction movement, and the pumping and suction force generated changes the air pressure in each area of the consumable, so as to control the fluids in the consumable to flow among the different areas. In order to achieve the automatic docking of the piston rod of the nucleic acid extraction and detection integrated machine with the piston of the consumable, the disclosure also designs a piston device movement assembly (piston driving mechanism), and the automatic combination and separation of the piston and the piston rod are achieved by means of the combined movement assembly and the separated movement assembly.

Further, the separated movement assembly prevents a jacking plate from moving upwards by ejecting the push rod, and under the restriction of the jacking plate, the piston stops moving upwards, thus enabling the piston to be separated from the piston rod that moves upwards continuously.

In some embodiments, the jacking plate is of a plate structure, the push rod is just across the jacking plate when being ejected, making the jacking plate impossible to move upwards continuously, and the piston below the jacking plate is also blocked by the jacking plate, making the piston impossible to move upwards continuously together with the piston rod, causing the piston to be separated from the piston rod that moves upwards continuously.

Further, the push rod is controlled by an electromagnet to be ejected or retracted, the push rod is ejected when the electromagnet is energized in one direction, and the push rod is retracted when the electromagnet is energized in the opposite direction.

The electromagnet generates the magnetism when being energized in one direction, so that the push rod is pushed out due to the fact that like magnetic poles repel each other; and the electromagnet generates the opposite magnetism when being energized in the other direction, so that the push rod is retracted due to the fact that unlike magnetic poles attract each other.

Further, the combined movement assembly comprises a movement module, the movement module is configured to control the vertical movements of the piston and the piston rod, and the jacking plate is arranged below the movement module and can move vertically with the movement module.

In some embodiments, the movement module is controlled by the motor in the nucleic acid extractor to move vertically so as to drive the piston rod, and the piston rod drives the piston to move vertically together.

Further, the piston rod penetrates through the jacking plate to be integrally connected with the movement module, and the jacking plate is movably sleeved on the piston rod from bottom to top.

In some embodiments, the piston rod is of a cylindrical rod structure, the piston rod and the movement module are integrally connected, and the piston rod moves vertically with the movement module; and the jacking plate is provided with a first round through hole whose diameter matches that of the cross section of the cylinder of the piston rod, so that the jacking plate can be sleeved on the piston rod from bottom to top.

Further, a spring is arranged below the jacking plate; when the push rod is ejected to prevent the jacking plate from moving upwards, the spring is compressed; and when the push rod is retracted, the spring is restored to push the jacking plate to return upwards.

Further, the spring is sleeved on a slide rod, the slide rod penetrates through the jacking plate to be connected to the movement module, the jacking plate can move vertically along the slide rod, a base is arranged below the slide rod, and the base has a diameter larger than that of the spring.

In some embodiments, after the jacking plate is sleeved on the piston rod from bottom to top, the other side of the jacking plate is provided with a second round through hole whose diameter matching that of the slide rod, the slide rod is sleeved with the spring, the base is arranged below the slide rod, and the base has the diameter larger than that of the spring, so that the lower end of the spring is fixed by the base. The spring and the slide rod are used together to support the jacking plate, meanwhile, the slide rod has a certain length, and the length of the slide rod determines the maximum distance of the jacking plate from the movement module.

In some embodiments, when the push rod extends, the jacking plate is blocked such that it cannot move upwards continuously with the movement module, thus the piston is prevented from moving upwards continuously with the piston rod, and the piston is separated from the piston rod. The slide rod provides the sufficient length to ensure that the jacking plate leaves the movement module and the piston and piston rod are separated.

Further, the combined movement assembly comprises a groove formed in an outer wall of the piston rod and a rib arranged on an inner wall of the piston; and when the piston rod moves downwards to be inserted into the piston, the groove can match with the rib, so that the piston and the piston rod are combined.

In some embodiments, the groove in the outer wall of the piston rod is an annular groove surrounding the circumference;

in some embodiments, the rib on the inner wall of the piston is an annular rib surrounding the circumference; and in some embodiments, the rib on the inner wall of the piston is composed of a plurality of symmetrically arranged small ribs.

Further, the piston is the hollow cylinder, and an upper end of the piston has a cross section diameter larger than that of a lower end and matching that of the piston rod, so that the piston rod and the upper end of the piston can be closely combined.

Further, a cylindrical wall of the upper end of the piston is provided with a longitudinal open groove, when the piston rod is inserted into the open groove, the cross section diameter of the upper end of the piston can be increased under the effect of the open groove, and thus the piston rod can be conveniently inserted into the piston and combined with the rib by means of the groove.

The configuration of the open groove provides an elastic space for outward expansion for the cross section diameter of the cylindrical wall of the upper end of the piston.

In some embodiments, when the piston rod is inserted, the piston rod makes the cylindrical wall of the piston slightly expand around under the action of the open groove, so as to facilitate the smooth insertion of the piston rod; and after the groove of the piston rod matches with the rib of the piston, the original diameter of the cylindrical wall of the upper end of the piston is restored, so that the piston rod and the upper end of the piston are closely combined.

Further, when the piston is located outside the reaction chamber, the permanent magnet and the piston are separately arranged.

In the first embodiment designed and completed by our study group, in the consumable, the reaction chamber, the piston and the magnetic rod are all of nested structures, the piston is the hollow cylinder and is located inside the reaction chamber and outside the hollow accommodating chamber, the reaction chamber is a very narrow annular channel surrounding the periphery of the hollow accommodating chamber, and the magnetic rod is located in the hollow cylinder of the hollow accommodating chamber and transmits the magnetic attraction force through an outer surface of the piston to the magnetic beads in the reaction chamber. When the magnetic rod moves downwards to attract the magnetic beads, the magnetic beads are adsorbed on the surface of the hollow accommodating chamber after being magnetized; when the magnetic rod moves upwards without magnetization, the magnetic beads are scattered in the narrow annular channel; the magnetic beads are difficult to gather and dead corners cannot be avoided in either case, and the vertically moving piston may also directly enter the reaction chamber to be in contact with the magnetic beads and the samples, which may be bonded by the piston such that some of the magnetic beads and the samples are taken away, resulting in insufficient adsorption, washing or elution in the process of nucleic acid adsorption, washing and nucleic acid elution by means of the magnetic beads. In addition, the piston is the hollow cylinder, the magnetic rod is located inside the piston, and both the piston and the magnetic rod need to move vertically precisely; the vertical movement of the internal magnetic rod and the vertical movement of the external piston need to be controlled simultaneously in such a design, which brings great difficulties to the design of a mechanism that drives the piston and the magnetic rod to operate, it is difficult to achieve the simultaneous and precise vertical movements of the piston and the magnetic rod, mistakes are made easily, and errors occur easily. Therefore, such design is likely to result in the reduction of the sensitivity of nucleic acid detection results of the nucleic acid extraction and detection integrated machine, and even result in missing and wrong detection.

In order to make the magnetic beads more concentrated in the reaction chamber, make the nucleic acid adsorption, washing and elution more sufficient, and ensure that the vertical movement of the piston and the vertical movement of the magnetic rod do not interfere with each other, the disclosure further provides another embodiment, so as to improve the structure of the nucleic acid extraction and amplification device, so that the reaction chamber, the piston and the magnetic rod can be arranged independently, the defects caused by nesting are avoided, meanwhile, the structure of the consumable is still compact without affecting the external dimensions, the internal structure operates more smoothly, and the overall operation of the nucleic acid extraction and detection integrated machine is not affected.

Further, the permanent magnet and the piston are respectively located at different positions outside the reaction chamber.

Further, the piston is located above the reaction chamber.

Further, the permanent magnet is located below the reaction chamber.

Further, the permanent magnet is the vertically placed magnetic rod, and the piston, the reaction chamber and the magnetic rod are arranged vertically in sequence from top to bottom.

The magnetic rod is originally located inside the hollow accommodating chamber, the hollow accommodating chamber is located in the middle of the reaction chamber, and when the magnetic rod moves downwards to enter the reaction chamber, the magnetic beads in the reaction chamber are attracted by the magnetic attraction force to be scattered and attracted on the outer wall of the hollow accommodating chamber; when the piston performs pumping, after the fluid sucked from other chambers is sucked into the reaction chamber via the micro-channel, the fluid can hardly evenly flush each magnetic bead scattered and attracted on the outer wall of the hollow accommodating chamber, and the dead corners appear easily; and in the pumping process of the piston, some of the samples may be bonded to the piston, which may result in errors.

In this embodiment, the piston, the reaction chamber and the magnetic rod are arranged vertically and independently in sequence from top to bottom, and when the magnetic rod moves upwards to get close to the reaction chamber, the magnetic attraction force is located at the bottom of the reaction chamber, so that the magnetic beads are gathered at the bottom of the reaction chamber, are more concentrated and are easy to collect, and thus the errors are reduced; when the magnetic rod moves downwards to get away from the reaction chamber, the magnetic attraction force disappears, and the magnetic beads are scattered in the cylindrical reaction chamber, so that the magnetic beads can make contact with the samples more completely and sufficiently and can also be washed and eluted more sufficiently; therefore, there is no dead corner in the reaction chamber for the magnetic beads, the adsorption, washing and elution of the nucleic acids by the magnetic beads can be more sufficient and thorough, the influence of the dead corners is eliminated, the efficiency of the nucleic acid extraction is improved, and the sensitivity of the nucleic acid detection is improved.

Further, the reaction chamber is a recess with an upward opening; and the piston moves vertically in a piston channel, and the piston channel is in communication with the reaction chamber.

In some embodiments, the reaction chamber is the cylindrical recess with the upward opening. Of course, the reaction chamber may also be in any shape such as a cube and a sphere.

The reaction chamber is changed from the original narrow annular channel surrounding the periphery of the piston into the cylindrical recess with the upward opening under the piston, that is, the reaction chamber is still in communication with the piston, but the piston cannot move downwards to the bottom of the reaction chamber and can only reach the upper side of the reaction chamber.

When the annular channel is used as the reaction chamber, the magnetic beads are distributed in each corner of the narrow annular channel, or are attracted to an outer wall of the piston channel by the magnetic rod in the concentric circle of the piston; when the piston performs pumping, after the fluid (for example, a washing liquid in a washing bin or an eluent in an elution bin) sucked from other chambers is sucked into the reaction chamber via the micro-channel (only one micro-channel), the fluid can hardly evenly flush the magnetic beads scattered in each corner, and the dead corners appear easily, resulting in insufficient washing or flushing; the dead corners may also exists even in the adsorption process, resulting in insufficient adsorption; therefore, the reaction chamber of the annular channel is not friendly to the nucleic acid extraction, and there may be problems of low extraction efficiency and insufficient extraction.

In the disclosure, the reaction chamber is separated from the piston to form the complete reaction chamber independently, the magnetic beads can be more evenly scattered in the samples in the reaction chamber and can be quickly and completely converged when being attracted by the magnetic rod, thus the dead corners are eliminated, and the efficiency of the processes of nucleic acid adsorption, washing and elution is effectively improved.

Since the piston cannot enter the reaction chamber, the problem that the piston may stick and take away the samples or the magnetic beads due to the vertical movement of the piston can be avoided, which further ensures the precision of the nucleic acid extraction process.

The reaction chamber is connected to the piston channel, and when the piston performs the vertical pumping and suction in the piston channel, the piston can generate the pumping and suction force on the fluid in the reaction chamber, thereby changing the air pressure in each area of the consumable (including the reaction chamber and other chambers in the consumable).

Further, the reaction chamber is located on the channel turntable; and the micro-channel in communication with the reaction chamber is provided in the channel turntable.

Further, the reaction chamber is the recess with the upward opening that is provided in the center of the channel turntable.

The reaction chamber of the consumable of the disclosure is essentially a groove formed in the center of the channel turntable, the groove may rotate along with the channel turntable, but is always located at the position of a rotating shaft in the center of the channel turntable, and the groove is always located under the piston.

The groove is formed in the center of the channel turntable to serve as the reaction chamber, and a magnetic rod channel for the magnetic rod to move is provided at the central rotating shaft below the channel turntable, so that the piston, the reaction chamber and the magnetic rod are independent of one another and are arranged in sequence from top to bottom; during operation, the magnetic beads are extracted in the cylindrical reaction chamber, and the magnetic rod attracts the magnetic beads under the reaction chamber, so that the magnetic beads are more concentrated, the adsorption, washing and elution are more sufficient, and the dead corners are eliminated; and since the magnetic rod and the piston are separated, the piston driving mechanism and a magnetic rod driving mechanism are also completely separated, and the vertical movements of the piston and the magnetic rod can be controlled more conveniently and accurately. When the nucleic acid extraction and amplification device is used to perform the nucleic acid extraction and amplification, the sensitivity and accuracy of the nucleic acid detection can be further improved, and the missing and wrong detection can be avoided.

Further, the size of the lower end of the piston and the size of the lower end of the piston channel are reduced; and when the piston moves downwards to the lowest position, the piston is blocked by the piston channel and cannot enter the reaction chamber.

Further, when the piston moves downwards to the lowest position, a bottom surface of the piston and the reaction chamber in the center of the channel turntable form a sealed chamber jointly.

Since a relatively small reaction chamber is required by the nucleic acid extraction, the reaction chamber has the relatively small cross section diameter. The lower end of the piston, that is, a piston head is in the shape of an inverted cone (funnel), and the cross section thereof is gradually reduced, and meanwhile, the lower end of the piston channel is also gradually reduced, so that when the piston moves downwards to the lowest position, the piston head is blocked by the piston channel and cannot enter the reaction chamber.

Further, a lower portion of the channel turntable is provided with a cross-shaped fixing element, a central rotating shaft of the fixing element is a hollow cylinder, and the hollow cylinder is the magnetic rod channel for the vertical displacement of the magnetic rod.

Further, a bottom surface of the reaction chamber is a top end of the magnetic rod channel.

The lower portion of the channel turntable is provided with the cross-shaped fixing element, so that the channel turntable can be fixed to the worm gear and worm transmission mechanism; and the worm gear and worm transmission mechanism drives the channel turntable to rotate precisely, thereby ensuring that the micro-channel in the channel turntable is precisely connected to certain chambers when needed and disconnected accurately when needed according to the working program settings.

When the worm gear and worm transmission mechanism rotates to drive the channel turntable to rotate, although the rotating shaft in the center of the fixing element also rotates, it will not move, while other positions will move annularly around the rotating shaft. In the disclosure, by skillfully using the characteristic that the rotating shaft rotates without displacement, the rotating shaft is changed into the hollow cylinder to serve as the magnetic rod channel, so that the magnetic rod can move vertically in the hollow cylinder of the rotating shaft; and at this moment, it should be noted that although the magnetic rod channel is rotating, the magnetic rod does not rotate, and the magnetic rod can only move vertically in the rotating magnetic rod channel.

Further, the upper end of the piston is provided with the piston driving mechanism for controlling the vertical displacement of the piston in the piston channel.

Further, it is characterized in that the lower end of the magnetic rod is provided with the magnetic rod driving mechanism for controlling the vertical displacement of the magnetic rod in the magnetic rod channel.

The piston needs to change the air pressure in each area in the consumable by means of the pumping and suction force generated by the vertical pumping and suction movements, thereby controlling the flow directions of the fluids in the consumable; when the piston moves downwards, the air pressure in the reaction chamber is increased, and the fluid in the reaction chamber is pressed into other chambers via the micro-channel; when the piston moves upwards, the air pressure in the reaction chamber is decreased, and the fluids in other chambers flow into the reaction chamber via the micro-channel. The magnetic rod needs to control the positions of the magnetic beads through the vertical movement; when the magnetic rod moves upwards to get close to the bottom surface of the reaction chamber, the magnetic rod generates the magnetic attraction force on the magnetic beads in the reaction chamber, so that the magnetic beads are gathered on the bottom surface of the reaction chamber; and when the magnetic rod moves downwards to get away from the bottom surface of the reaction chamber, the magnetic attraction force on the magnetic beads in the reaction chamber is reduced, so that the magnetic beads are scattered in the reaction chamber.

The magnetic rod is fixed in the nucleic acid extraction and detection integrated machine, and the lower end of the magnetic rod is also fixedly provided with the magnetic rod driving mechanism, which drives the magnetic rod to move vertically by means of the motor. In addition, the piston is a part of the consumable and needs to be replaced frequently, thus the design of the piston driving mechanism is more complex, and the piston driving mechanism needs to be automatically combined with the piston before driving the piston to move vertically and also needs to be automatically separated from the piston after the piston moves vertically.

When the piston is located inside the reaction chamber, the piston is the hollow cylinder, and the magnetic rod is sleeved with the piston; the design of a piston movement assembly is very complex, the piston rod of a specific structure is required to be provided firstly to be combined with the hollow cylinder type piston, then the vertical pumping and suction movements are performed after the firm combination, at the same time, a proper space is also required to be reserved for the magnetic rod inside the piston, so as not to hinder the vertical movement of the magnetic rod, in addition, the piston rod is difficult to separate after being combined with the hollow cylinder type piston, a complex separation mechanism is also required to promote the smooth separation of the hollow cylinder type piston from the piston rod, precise control is difficult, and the condition that the combination of the piston fails or the piston is difficult to separate after being combined occurs easily, so that the nucleic acid detection process is stuck.

When the piston is located outside the reaction chamber, in the nucleic acid extraction and detection integrated machine provided by the embodiment, the piston is no longer the hollow cylinder, and the magnetic rod has also been moved out of the piston and placed below the piston and the reaction chamber, which also brings great benefits to the design of the piston driving mechanism. The piston in the consumable does not need to be in the hollow cylinder shape any more, but can be a solid piston directly, and a piston cover is provided at the top of the piston. The piston driving mechanism is redesigned for the solid piston provided with the piston cover, so that it can drive the piston more easily and smoothly to complete the pumping and suction movements to complete the extraction and purification of the nucleic acids.

Further, the piston driving mechanism comprises a vertical movement module and a lateral movement module, wherein the vertical movement module is configured to drive the piston to move vertically; the lateral movement module is configured to realize the combination or separation of the piston and the piston driving mechanism; and the vertical movement module and the lateral movement module are integrally nested and combined.

After the consumable is placed into the nucleic acid extraction and detection integrated machine, the pumping and suction movements of the piston inside the consumable are mainly completed in the following steps: 1. grasping the piston; 2. enabling the piston to move vertically; 3. releasing the piston. That is, 1. the piston driving mechanism is combined with the piston; 2. the piston driving mechanism drives the piston to move vertically; 3. the piston driving mechanism is separated from the piston.

The piston driving mechanism of the disclosure is combined with and separated from the piston by means of the lateral movement module, and the vertical movement of the piston is achieved by means of the vertical movement module, so that the whole process can be more quickly and conveniently completed in a full-automatic manner.

The vertical movement module of the piston driving mechanism can drive the piston to move vertically, thereby controlling the pumping and suction actions of the piston in the consumable. The lateral movement module of the piston driving mechanism can move left and right, thereby achieving the combination and separation of the driving mechanism and the piston. In the working process of the nucleic acid extraction and detection integrated machine, the consumable is required to be placed to a specific position inside the nucleic acid extraction and detection integrated machine firstly, at this moment, the piston and the piston driving mechanism are separated, then the piston driving mechanism is started to enable the lateral movement module of the piston driving mechanism to move to the left or right, and when the lateral movement module moves to the proper position, the piston driving mechanism is combined with the piston, so that the next vertical pumping and suction movement of the piston can be carried out; and after the vertical pumping and suction movement of the piston is completed, the lateral movement module moves to the right or left in the opposite direction, so that the piston driving mechanism is separated from the piston.

Further, the lateral movement module comprises a curved rod structure and a slider structure; the curved rod structure is located above the slider structure; and the curved rod structure rotates to enable the slider structure to move left and right, so as to drive the piston and the driving mechanism to be combined or separated.

Further, the curved rod structure comprises a fixed shaft and a rocking handle, one end of the rocking handle is connected to the fixed shaft, and the rocking handle can perform the circular movement around the fixed shaft.

The lateral movement module moves left and right mainly by means of the principle of the curved rod and slider structures, and the rocking handle of the curved rod structure performs the circular movement by means of the motor, so as to drive the slider structure to move left and right.

Further, the slider structure is provided with a slide rail with an upward opening; the other end of the rocking handle is provided with a connecting rod; and in the process of the circular movement of the rocking handle, when the connecting rod is inserted into the slide rail, the rocking handle rotates to drive, by means of the connecting rod, the slide rail to move, thereby driving the slider structure to move left and right.

In some embodiments, the slider structure is provided with the slide rail with the upward opening; when the rocking handle performs the clockwise circular movement around the fixed shaft, in the process that the rocking handle rotates to a lower semicircle, the connecting rod of the rocking handle may slide into the slide rail, and in the process of the continuous clockwise circular movement, the connecting rod of the rocking handle may continue to move downwards and to the left at the same time; in the process of the downward movement, the connecting rod also moves downwards along the slide rail, in the process of the leftward movement, the connecting rod drives the slider structure to move to the left, and when the slider structure moves to the left to reach a specific position, the slider structure and the piston are smoothly combined.

In a similar way, when the rocking handle performs the anticlockwise circular movement around the fixed shaft, in the process that the rocking handle rotates to the lower semicircle, the connecting rod of the rocking handle may slide into the slide rail, and in the process of the continuous clockwise circular movement, the connecting rod of the rocking handle may continue to move downwards and to the right at the same time; in the process of the downward movement, the connecting rod also moves downwards along the slide rail, in the process of the rightward movement, the connecting rod drives the slider structure to move to the right, and when the slider structure moves to the right to reach a specific position, the slider structure and the piston are smoothly separated.

Therefore, all that is needed for smoothly combining the slider structure with the piston is to control the rocking handle to perform the clockwise circular movement of the lower semicircle around the fixed shaft firstly, and then the pumping and suction movement of the piston can be started; and after the pumping and suction movement is completed, all that is needed for smoothly separating the slider structure from the piston is to control the rocking handle to perform the anticlockwise circular movement of the lower semicircle around the fixed shaft.

In some embodiments, the rocking handle is just required to perform the clockwise or anticlockwise rotation around a quarter of the circumference on the lower semicircle, and the left-and-right displacement of the slider structure and the combination and separation of the slider structure and the piston can be achieved.

Further, the curved rod structure is provided with a bracket, and the curved rod structure is fixed above the vertical movement module by means of the bracket.

In some embodiments, the bracket is composed of a horizontal plate and a vertical plate, the horizontal plate is fixed to the vertical movement module, a lower end of the vertical plate is fixed to the slider structure, and an upper end thereof is used to fix the fixed shaft of the curved rod structure.

Further, a bottom surface of the slider structure is provided with an arc-shaped notch with an opening; the piston comprises a top cover and the piston rod, and the top cover has the diameter greater than the cross section diameter of the piston rod; and when the slider structure gets close to the piston, an open portion of the arc-shaped notch is sleeved on the piston rod, so that the piston is combined with the driving mechanism and moves vertically with the vertical movement module.

In some embodiments, the top cover has the cross section diameter obviously greater than that of the piston rod, and the top cover is in a shape similar to a cake structure. Since the consumable is fixed in the nucleic acid extraction and detection integrated machine, the piston of the consumable is also fixed, can only perform the vertical pumping and suction movement and cannot move left and right. Therefore, after the slider structure moves to the left and the arc-shaped notch in the bottom surface is sleeved on the piston rod, as long as the slider structure does not retreat to the right, the piston is always combined with the slider structure and cannot be separated, and at this moment, the vertical movement module can move vertically to drive the piston to perform the pumping and suction movement; and after the pumping and suction movement is completed, the slider structure moves to the right, and then the piston can be separated from the slider structure.

Further, the lateral movement module is integrally nested with the vertical movement module by means of the slider structure and can move left and right relative to the vertical movement module.

The vertical movement module can only move vertically and cannot move left and right; and although the lateral movement module is integrally nested with the vertical movement module, the lateral movement module can move left and right relative to the vertical movement module, that is, the lateral movement module can slide left and right relative to the vertical movement module.

Further, the slider structure is provided with two bumps, which are respectively a first bump and a second bump; the vertical movement module is provided with two grooves, which are respectively a first groove and a second groove; and when the vertical movement module and the lateral movement module are integrally nested and combined, the first bump and the second bump are embedded into the first groove and the second groove respectively.

Further, the first bump, the second bump, the first groove and the second groove are all obliquely provided at an angle of 1-10 degrees with the horizontal direction; and when the lateral movement module moves left and right, the first bump and the second bump slide left and right in the first groove and the second groove respectively.

The vertical movement module comprises a movement handle and a main movement body, the first groove and the second groove are provided on the main movement body, the first bump and the second bump of the slider structure can be inserted into the first groove and the second groove respectively from one side of the main movement body, and the slider structure can translate left and right along the first groove and the second groove, that is, the lateral movement module translates left and right relative to the vertical movement module.

The first bump, the second bump, the first groove and the second groove are all obliquely provided at an angle of 1-10 degrees with the horizontal direction, because if they are completely horizontal, the piston driving mechanism and the piston are difficult to fit completely in the process of combination and separation; however, if they are provided at a certain inclination angle, the piston driving mechanism and the piston can be combined and separated more easily and can fit seamlessly. Of course, the inclination angle should not be too large, the first bump, the second bump, the first groove and the second groove are just slightly inclined, and the inclination angle needs to be controlled at an angle of 1-10 degrees, preferably 2 degrees.

Therefore, the lateral movement module can only move left and right, relative to the vertical movement module, in the first groove and the second groove, and in the process that the rocking handle rotates to drive, by means of the connecting rod, the slide rail to move, conditions such as higher-degree inclination of the lateral movement module that is away from the groove and relative to the vertical movement module and the like can be avoided.

Further, a limiting mechanism is arranged on a side wall of the vertical movement module, a limiting rail is arranged on a side wall of the lateral movement module, and the limiting mechanism moves left and right in the limiting rail and is configured to limit the left-and-right displacement of the lateral movement module.

The limiting mechanism can only move left and right in the limiting rail, which limits the maximum distance of the left-and-right displacement of the lateral movement module. Meanwhile, after the rocking handle performs the clockwise circular movement of the lower semicircle around the fixed shaft firstly, the lateral movement module moves to the left to reach the leftmost end, the limiting mechanism is located at the rightmost end of the limiting rail at this moment, and the slider structure is smoothly combined with the piston; and after the rocking handle performs the anticlockwise circular movement of the lower semicircle around the fixed shaft, the lateral movement module moves to the right to reach the rightmost end, the limiting mechanism is located at the leftmost end of the limiting rail at this moment, and the slider structure is smoothly separated from the piston.

Further, the nucleic acid extraction and amplification device comprises a nucleic acid extraction assembly and a nucleic acid amplification assembly; the nucleic acid extraction assembly is configured to extract the nucleic acids in the samples; the piston, the reaction chamber and the permanent magnet belong to the nucleic acid extraction assembly; and the nucleic acid amplification assembly is configured to amplify the nucleic acids extracted by the nucleic acid extraction assembly.

Further, the nucleic acid extraction assembly further comprises the pyrolysis bin, the washing bin and the elution bin; the pyrolysis bin is configured to store the samples, a pyrolysis liquid, the magnetic beads and a waste liquid generated after pyrolysis; the washing bin is configured to store the washing liquid and a waste liquid generated after washing; one or more washing bins are provided; the elution bin is configured to store the eluent; through holes are provided in a bottom of the pyrolysis bin, a bottom of the washing bin and a bottom of the elution bin; the micro-channel is provided in the channel turntable; and the channel turntable can be rotated to enable the micro-channel to be in selective communication with the bottom through hole of the pyrolysis bin, the washing bin or the elution bin, so that the reaction chamber is in selective communication with the pyrolysis bin, the washing bin or the elution bin.

The communication of the disclosure refers to fluid communication, and the fluid can flow from one place to another and may pass through some physical structures to play a guiding role in the flow process. Passing through the physical structures generally means that the fluid passes through surfaces of the physical structures or internal spaces of the structures to passively or actively flow to another place; the passivity generally refers to the flow caused by an external force, for example, the flow under pressure. In the disclosure, it specifically means that the fluid can enter the reaction chamber from other chambers of the consumable and can also enter other chambers from the reaction chamber and the fluid can be switched repeatedly between the different chambers.

The term "selective" here means that when the reaction chamber is in fluid communication with the pyrolysis bin, the washing bin and the elution bin are not in fluid communication with the reaction chamber; when the washing bin is in fluid communication with the reaction chamber, the reaction chamber is not in fluid communication with the pyrolysis bin and the elution bin; when the elution bin is in fluid communication with the reaction chamber, the reaction chamber is not in fluid communication with the pyrolysis bin and the washing bin; and that is, the reaction chamber is in selective fluid communication with other chambers of the consumable at the proper time.

In some embodiments, the channel turntable is only provided with one bottom channel, so that the reaction chamber can only be in communication with one chamber by means of the bottom channel each time.

Further, the nucleic acid amplification assembly comprises a PCR tube and a PCR tube channel; and after the nucleic acid extraction is completed, the channel turntable is rotated to enable the micro-channel to be in selective communication with the PCR tube channel, so that the reaction chamber is in selective communication with the PCR tube.

Further, the PCR tube is detachably connected to a bottom surface of the nucleic acid extraction and amplification device, and the sealed connection can be realized after the connection.

In some embodiments, the PCR tube of the nucleic acid amplification assembly of the disclosure is of a detachable structure, that is, other portions of the consumable are integrally formed and prepared, and a connection port is reserved at the position of the PCR tube; the PCR tube is prepared separately, meanwhile, the reagent required by a nucleic acid amplification reaction is placed in the PCR tube in advance, and the PCR tube is covered with a lid for sealed storage; when nucleic acid detection is required to be performed, the lid of the PCR tube is removed, and then the PCR tube is connected to the reserved connection port of the consumable to achieve the sealed connection.

The PCR tube of the original consumable is directly integrally formed with the consumable, the PCR tube prepared in such a way may have a relatively thick wall, and the heating process is slow in the process of isothermal nucleic acid amplification, which prolongs the time required for nucleic acid detection; the PCR tube having a thinner wall and prepared in advance is adopted in the disclosure and is connected to the consumable when used, so that the problem of slow heating can be well solved, and thereby greatly improving the detection efficiency. In addition, the PCR tube prepared separately can store the reaction reagent in advance, which is more beneficial to storage and transportation.

In some embodiments, the PCR tube channel at an inlet of the PCR tube deviates from the center line of the PCR tube.

The nucleic acid extraction and amplification device of the disclosure is a core component installed in the nucleic acid extraction and detection integrated machine. Since the component can be used only after it is thoroughly cleaned to be sterile each time, it is generally made into the disposable consumable for use. Therefore, the nucleic acid extraction and amplification device is also called the consumable in the disclosure, and of course, it can also be made into a reusable component.

A fluid inlet of the PCR tube deviating from the center line means that the fluid does not enter the PCR tube from the middle of a tube port, but needs to deviate from the center and enter from the position close to one side of the PCR tube, and cannot directly enter along a tube port wall. Since an inner wall of the tube port of the PCR tube needs to be subjected to hydrophobic treatment, the fluid cannot enter directly along the tube port wall; however, if the fluid enters from the middle of the tube port, fluid sputtering occurs very easily, which affects the detection sensitivity; when the fluid enters from the position deviating from the center of the tube port, the fluid can be in contact with part of the inner wall of a lower side of the PCR tube in the falling process and then flows downwards along the inner wall, which obviously reduces fluid sputtering and ensures that the inner wall near the tube port is not stained with the fluid, thereby ensuring the more accurate detection result.

The PCR tube of the nucleic acid extraction and amplification device of the disclosure can be directly heated by the driving component of the nucleic acid extraction and detection integrated machine, and can also be disassembled and transferred to other devices to be heated.

In some embodiments, a film is further included and is provided with through holes in communication with the reaction chamber, a nucleic acid extraction element and a nucleic acid amplification element, wherein the through hole of the film at the inlet of the PCR tube deviates from the center line of the PCR tube.

The through holes in the film are used as a part of the fluid channel, and the PCR tube channel can be led to the inlet of the PCR tube by means of the film.

Further, the nucleic acid amplification element also comprises a PCR reagent bin and a paraffin oil bin, wherein the PCR reagent bin is configured to store a PCR reagent, and the paraffin oil bin is configured to store paraffin oil which is used for heat-sealing of the PCR tube; and a bottom of the PCR reagent bin and a bottom of the paraffin oil bin are both provided with through holes, so that the PCR reagent bin and the paraffin oil bin can be in communication with the reaction chamber respectively.

Further, the nucleic acid extraction and amplification device further comprises an upper cover and a bottom cover, wherein the upper cover is attached with a waterproof and gas-permeable membrane for gas exchange and biological pollution prevention; the bottom cover is provided with a penetrating area for accommodating the channel turntable, and the PCR tube is connected to the bottom cover; one or more PCR tubes and PCR tube channels are provided; and the nucleic acid extraction element or the nucleic acid amplification element is also provided with a reservation bin which can be in communication with the reaction chamber respectively.

The nucleic acid extraction and amplification device of the disclosure does not need to be provided with a chamber for storing the waste liquid. After DNA to be tested is adsorbed by the magnetic beads, the magnetic beads are always attracted in the reaction chamber under the attraction action of the magnetic rod on the magnetic beads, and the waste liquid generated after pyrolysis and washing is pressed back to the pyrolysis bin and the washing bin respectively under the action of the piston. Since the channel turntable is only provided with one bottom channel, with the rotation of the channel turntable, the pyrolysis bin and the washing bin are no longer in communication with the reaction chamber, so that the DNA to be tested is completely separated from the waste liquid.

Further, the driving component can also heat and control the temperature of the nucleic acid extraction and amplification device.

Further, a light path component, a vertical movement component and a horizontal movement component are further included; the light path component is configured to perform fluorescence collection on amplification results of the nucleic acid extraction and amplification device; the vertical movement component is configured to control the vertical movements of the piston rod and the magnetic rod; and the horizontal movement component is configured to control the forward and backward movement of the vertical movement component.

Further, the nucleic acid extraction and detection integrated machine of the disclosure also comprises a bottom plate which provides a supporting frame for the nucleic acid extraction and detection integrated machine.

In another aspect, the disclosure further provides the above-mentioned worm gear and worm transmission mechanism for the nucleic acid extraction and detection integrated machine to accurately control the rotation angle of the channel turntable of the nucleic acid extractor each time. The aperture of the micro-channel of the channel turntable is 600 microns, and the rotation angle of the channel turntable is 35-151 degrees each time.

The nucleic acid extraction and detection integrated machine of the disclosure comprises the nucleic acid extraction and amplification device (the consumable) and the channel turntable, wherein the channel turntable precisely matches with a turntable base connected to the worm gear shaft; the nucleic acid extraction and amplification device is mainly composed of a housing having a plurality of chambers, the chambers include the reaction chamber, the pyrolysis bin, the washing bin (which may include a primary washing bin and a secondary washing bin), the elution bin, the PCR reagent bin, the paraffin oil bin, the PCR tube and the PCR tube channel, and the bottom of each chamber is respectively provided with the micro-pores. In some embodiments, the nine micro-pores corresponding to the pyrolysis bin, the primary washing bin, the secondary washing bin, the PCR reagent bin, the paraffin oil bin and the three PCR tube channels are respectively provided around the bottom of the reaction chamber; and the channel turntable is provided with two turntable micro-pores and one bottom channel in communication with the two turntable micro-pores. The channel turntable can be rotated to enable the reaction chamber to be in communication with the pyrolysis bin, the primary washing bin, the secondary washing bin, the PCR reagent bin, the paraffin oil bin or the PCR tube channel respectively by means of the bottom channel. In the initial position, the reaction chamber is in communication with the pyrolysis bin by means of the micro-channel of the channel turntable; after the pyrolysis is completed, the channel turntable needs to rotate clockwise by 50 degrees to communicate the reaction chamber with the primary washing bin; after the primary washing is completed, the channel turntable needs to rotate clockwise by 50 degrees to communicate the reaction chamber with the secondary washing bin; after the secondary washing is completed, the channel turntable needs to rotate clockwise by 42 degrees to communicate the reaction chamber with the PCR reagent bin; after the nucleic acid extraction is completed, the nucleic acids to be tested are transferred to the reaction chamber, and the channel turntable needs to rotate clockwise by 128 degrees at this moment to communicate the reaction chamber with the second PCR tube channel; after the nucleic acids to be tested are transferred to the PCR tube, the channel turntable needs to rotate anticlockwise by 93 degrees to communicate the reaction chamber with the paraffin oil bin; and after the paraffin oil is transferred to the reaction chamber, the channel turntable needs to rotate clockwise by 128 degrees to communicate the reaction chamber with the second PCR tube channel again to transfer the paraffin oil to the PCR tube for heat-sealing, and then the PCR amplification reaction is performed.

In some embodiments, the micro-pores of the various chambers of the nucleic acid extraction and detection integrated machine of the disclosure, as well as the micro-pores and the micro-channel of the channel turntable, all have the apertures of 600 microns. It can be understood that the smaller the aperture, the higher the precision of the rotation angle of the channel turntable that needs to be controlled, and a slight error may lead to sample leakage and other problems; and in addition, the stability needs to be provided by the worm gear shaft for the precise matching of the channel turntable with the turntable base, so that the turntable base is more stable, and the precise rotation of the channel turntable is guaranteed.

In some embodiments, the piston driving mechanism may also cause slight shaking of the consumable when vertically driving, by means of the piston rod, the piston to move, which will easily affects the precise matching of the channel turntable with the turntable base. With regard to the worm gear and worm transmission mechanism, the stability of the channel turntable can be sufficiently ensured by means of the worm gear shaft, so that the channel turntable precisely matched with the turntable base, the accurate rotation of the channel turntable is achieved under low-speed rotation of the worm gear, and thus the smooth nucleic acid extraction and amplification are ensured.

In the disclosure, the expensive precision motor used in the early stage of study is replaced by the driving device which is simple in structure, low in cost, small and convenient to install, debug and maintain, so that accurate communication of the micro-pores having the aperture of 600 microns and the micro-channel under the load-speed and low-load conditions of the nucleic acid extractor is successfully achieved, the stability can be kept after the communication, and the problem of sample leakage can be avoided.

In another aspect, the disclosure provides the nucleic acid extraction and amplification device (consumable), comprising the piston, the reaction chamber and the permanent magnet, wherein the piston is configured to control the flow direction of the fluid in the nucleic acid extraction and amplification device; the reaction chamber is configured to provide the place for the magnetic beads to adsorb, wash and elute the nucleic acids; the permanent magnet is configured to provide the magnetic attraction force for the magnetic beads; and the piston is located outside the reaction chamber.

Further, the permanent magnet and the piston are separately arranged.

Further, the permanent magnet and the piston are respectively located at the different positions outside the reaction chamber.

Further, the piston is located above the reaction chamber.

Further, the permanent magnet is located below the reaction chamber.

Further, the permanent magnet is the vertically placed magnetic rod, and the piston, the reaction chamber and the magnetic rod are arranged vertically in sequence from top to bottom.

Further, the reaction chamber is the recess with the upward opening; and the piston moves vertically in the piston channel, and the piston channel is in communication with the reaction chamber.

Further, the reaction chamber is located on the channel turntable; and the micro-channel in communication with the reaction chamber is provided in the channel turntable.

Further, the reaction chamber is the recess with the upward opening that is provided in the center of the channel turntable.

Further, the size of the lower end of the piston and the size of the lower end of the piston channel are reduced; and when the piston moves downwards to the lowest position, the piston is blocked by the piston channel and cannot enter the reaction chamber.

Further, when the piston moves downwards to the lowest position, a bottom surface of the piston and the reaction chamber in the center of the channel turntable form the sealed chamber jointly.

Further, the lower portion of the channel turntable is provided with the cross-shaped fixing element, the central rotating shaft of the fixing element is the hollow cylinder, and the hollow cylinder is the magnetic rod channel for the vertical displacement of the magnetic rod.

Further, the bottom surface of the reaction chamber is the top end of the magnetic rod channel.

Further, the lower end of the magnetic rod is provided with the magnetic rod driving mechanism for controlling the vertical displacement of the magnetic rod in the magnetic rod channel; and the upper end of the piston is provided with the piston driving mechanism for controlling the vertical displacement of the piston in the piston channel.

In another aspect, the disclosure comprises the following embodiments:

In one embodiment, the nucleic acid extraction and detection integrated machine includes the nucleic acid extraction and amplification device and the driving component, wherein the nucleic acid extraction and amplification device is configured to extract, purify and amplify the nucleic acids in the samples;

the driving component is configured to carry and drive the nucleic acid extraction and amplification device to operate, and comprises the piston driving mechanism and the worm gear and worm transmission mechanism; the piston driving mechanism is configured to drive the piston in the nucleic acid extraction and amplification device to move vertically;

the worm gear and worm transmission mechanism is configured to drive the channel turntable to rotate, thereby connecting and disconnecting the different chambers of the nucleic acid extraction and amplification device; and the worm gear and worm transmission mechanism is provided with the elastic element capable of resetting, which is configured to provide thrust for the worm shaft to make the worm close to the worm gear so as to eliminate the backlash.

In one embodiment, the elastic element capable of resetting is the reset spring, the reset spring is located at the first end of the worm shaft, and the second end of the worm shaft is flexibly fixed by means of the angular contact bearing.

In one embodiment, one reset spring is provided, the first end of the reset spring is movably connected to the worm shaft by means of the connecting module, and the connecting module is provided with the arc-shaped recess and is in direct contact with the worm shaft by means of the arc-shaped recess.

In one embodiment, the connecting module is made of the lubricating materials, and the arc-shaped recess is provided with the arc-shaped rib which matches with the arc-shaped groove in the worm shaft.

In one embodiment, the connecting module is made of the POM or Teflon materials, the second end of the reset spring is fixed to the base, and the reset spring has the elastic modulus of 0.5-1.0 N/m$^2$.

In one embodiment, the machine further comprises the bracket configured to fix the worm gear and worm transmission mechanism; the angular contact bearing is pressed into the bracket in the shrink-fit manner, and the second end of the worm shaft is locked on the angular contact bearing by means of the lock nut; the base of the reset spring is fixed to the bracket; the machine further comprises the motor which can drive the motor shaft to rotate; the worm shaft is connected to the motor shaft by means of the coupling; and the coupling is the diaphragm coupling having flexibility.

In one embodiment, the nucleic acid extraction and amplification device comprises the piston, the reaction chamber and the permanent magnet; the piston is configured to control the flow direction of the fluid in the nucleic acid extraction and amplification device; the reaction chamber is configured to provide the place for the magnetic beads to adsorb, wash and elute the nucleic acids; the permanent magnet is configured to provide the magnetic attraction force for the magnetic beads; and the piston is located inside or outside the reaction chamber.

In one embodiment, when the piston is located inside the reaction chamber, the reaction chamber is internally provided with the piston and the hollow accommodating chamber; the hollow accommodating chamber is configured to accommodate the permanent magnet, the piston is the hollow cylinder, and the hollow cylinder in the piston has the diameter matching that of the hollow accommodating chamber, so that the piston can be sleeved outside the hollow accommodating chamber and move vertically along the outer wall of the hollow accommodating chamber; the displacement of the piston causes the pressure change, thereby promoting the fluids to flow between the reaction chamber and other chambers; and the permanent magnet is the magnetic rod.

In one embodiment, when the piston is located inside the reaction chamber, the piston driving mechanism comprises the combined movement assembly and the separated movement assembly; the combined movement assembly can combine the piston with the piston rod, thereby enabling the piston rod to drive the piston to move vertically; and the separated movement assembly prevents the piston from moving by ejecting the push rod, thereby enabling the piston to be separated from the piston rod that moves continuously.

In one embodiment, the separated movement assembly prevents the jacking plate from moving upwards by ejecting the push rod, and under the restriction of the jacking plate, the piston stops moving upwards, thus enabling the piston to be separated from the piston rod that moves upwards continuously.

In one embodiment, the push rod is controlled by the electromagnet to be ejected or retracted, the push rod is ejected when the electromagnet is energized in one direction, and the push rod is retracted when the electromagnet is energized in the opposite direction.

In one embodiment, the combined movement assembly comprises the movement module, the movement module is configured to control the vertical movements of the piston and the piston rod, and the jacking plate is arranged below the movement module and can move vertically with the movement module.

In one embodiment, the piston rod penetrates through the jacking plate to be integrally connected with the movement module, and the jacking plate is movably sleeved on the piston rod from bottom to top.

In one embodiment, the spring is arranged below the jacking plate; when the push rod is ejected to prevent the jacking plate from moving upwards, the spring is compressed; and when the push rod is retracted, the spring is restored to push the jacking plate to return upwards.

In one embodiment, the spring is sleeved on the slide rod, the slide rod penetrates through the jacking plate to be connected to the movement module, the jacking plate can move vertically along the slide rod, the base is arranged below the slide rod, and the base has the diameter larger than that of the spring.

In one embodiment, the combined movement assembly comprises the groove formed in the outer wall of the piston rod and the rib arranged on the inner wall of the piston; and when the piston rod moves downwards to be inserted into the piston, the groove can match with the rib, so that the piston and the piston rod are combined.

In one embodiment, the piston is the hollow cylinder, and the upper end of the piston has the cross section diameter larger than that of the lower end and matching that of the piston rod, so that the piston rod and the upper end of the piston can be closely combined.

In one embodiment, the cylindrical wall of the upper end of the piston is provided with the longitudinal open groove, when the piston rod is inserted into the open groove, the cross section diameter of the upper end of the piston can be increased under the effect of the open groove, and thus the piston rod can be conveniently inserted into the piston and combined with the rib by means of the groove.

In one embodiment, when the piston is located outside the reaction chamber, the permanent magnet and the piston are separately arranged.

In one embodiment, the permanent magnet and the piston are respectively located at the different positions outside the reaction chamber.

In one embodiment, the piston is located above the reaction chamber.

In one embodiment, the permanent magnet is located below the reaction chamber.

In one embodiment, the permanent magnet is the vertically placed magnetic rod, and the piston, the reaction chamber and the magnetic rod are arranged vertically in sequence from top to bottom.

In one embodiment, the reaction chamber is the recess with the upward opening; and the piston moves vertically in the piston channel, and the piston channel is in communication with the reaction chamber.

In one embodiment, the reaction chamber is located on the channel turntable; and the micro-channel in communication with the reaction chamber is provided in the channel turntable.

In one embodiment, the reaction chamber is the recess with the upward opening that is provided in the center of the channel turntable.

In one embodiment, the size of the lower end of the piston and the size of the lower end of the piston channel are reduced; and when the piston moves downwards to the lowest position, the piston is blocked by the piston channel and cannot enter the reaction chamber.

In one embodiment, when the piston moves downwards to the lowest position, the bottom surface of the piston and the reaction chamber in the center of the channel turntable form the sealed chamber jointly.

In one embodiment, the lower portion of the channel turntable is provided with the cross-shaped fixing element, the central rotating shaft of the fixing element is the hollow cylinder, and the hollow cylinder is the magnetic rod channel for the vertical displacement of the magnetic rod.

In one embodiment, the bottom surface of the reaction chamber is the top end of the magnetic rod channel.

In one embodiment, the lower end of the magnetic rod is provided with the magnetic rod driving mechanism for controlling the vertical displacement of the magnetic rod in the magnetic rod channel; and the upper end of the piston is provided with the piston driving mechanism for controlling the vertical displacement of the piston in the piston channel.

In one embodiment, the piston driving mechanism comprises the vertical movement module and the lateral movement module; the vertical movement module is configured to drive the piston to move vertically; the lateral movement module is configured to realize the combination or separation of the piston and the piston driving mechanism; and the vertical movement module and the lateral movement module are integrally nested and combined.

In one embodiment, the lateral movement module comprises the curved rod structure and the slider structure; the curved rod structure is located above the slider structure; and the curved rod structure rotates to enable the slider structure to move left and right, so as to drive the piston and the driving mechanism to be combined or separated.

In one embodiment, the curved rod structure comprises the fixed shaft and the rocking handle, one end of the rocking handle is connected to the fixed shaft, and the rocking handle can perform the circular movement around the fixed shaft.

In one embodiment, the slider structure is provided with the slide rail with the upward opening; the other end of the rocking handle is provided with the connecting rod; and in the process of the circular movement of the rocking handle, when the connecting rod is inserted into the slide rail, the rocking handle rotates to drive, by means of the connecting rod, the slide rail to move, thereby driving the slider structure to move left and right.

In one embodiment, the curved rod structure is provided with the bracket, and the curved rod structure is fixed above the vertical movement module by means of the bracket.

In one embodiment, the bottom surface of the slider structure is provided with the arc-shaped notch with the opening; the piston comprises the top cover and the piston rod, and the top cover has the diameter greater than the cross section diameter of the piston rod; and when the slider structure gets close to the piston, the open portion of the arc-shaped notch is sleeved on the piston rod, so that the piston is combined with the driving mechanism and moves vertically with the vertical movement module.

In one embodiment, the lateral movement module is integrally nested with the vertical movement module by means of the slider structure and can move left and right relative to the vertical movement module.

In one embodiment, the slider structure is provided with the two bumps, which are respectively the first bump and the second bump; the vertical movement module is provided with the two grooves, which are respectively the first groove and the second groove; and when the vertical movement module and the lateral movement module are integrally nested and combined, the first bump and the second bump are embedded into the first groove and the second groove respectively.

In one embodiment, the first bump, the second bump, the first groove and the second groove are all obliquely provided at the angle of 1-10 degrees with the horizontal direction; and when the lateral movement module moves left and right, the first bump and the second bump slide left and right in the first groove and the second groove respectively.

In one embodiment, the limiting mechanism is arranged on the side wall of the vertical movement module, the limiting rail is arranged on the side wall of the lateral movement module, and the limiting mechanism moves left and right in the limiting rail and is configured to limit the left-and-right displacement of the lateral movement module.

In one embodiment, the nucleic acid extraction and amplification device comprises the nucleic acid extraction assembly and the nucleic acid amplification assembly; the nucleic acid extraction assembly is configured to extract the nucleic acids in the samples; the piston, the reaction chamber and the permanent magnet belong to the nucleic acid extraction assembly; and the nucleic acid amplification assembly is configured to amplify the nucleic acids extracted by the nucleic acid extraction assembly.

In one embodiment, the nucleic acid extraction assembly further comprises the pyrolysis bin, the washing bin and the elution bin; the pyrolysis bin is configured to store the samples, the pyrolysis liquid, the magnetic beads and the waste liquid generated after pyrolysis; the washing bin is configured to store the washing liquid and the waste liquid generated after washing; one or more washing bins are provided; the elution bin is configured to store the eluent; through holes are provided in the bottom of the pyrolysis bin, the bottom of the washing bin and the bottom of the elution bin; the micro-channel is provided in the channel turntable; and the channel turntable can be rotated to enable the micro-channel to be in selective communication with the bottom through hole of the pyrolysis bin, the washing bin or the elution bin, so that the reaction chamber is in selective communication with the pyrolysis bin, the washing bin or the elution bin.

In one embodiment, the nucleic acid amplification assembly comprises the PCR tube and the PCR tube channel; and after the nucleic acid extraction is completed, the channel turntable is rotated to enable the micro-channel to be in selective communication with the PCR tube channel, so that the reaction chamber is in selective communication with the PCR tube.

In one embodiment, the PCR tube is detachably connected to the bottom surface of the nucleic acid extraction and amplification device, and the sealed connection can be realized after the connection.

In one embodiment, the PCR tube channel at the inlet of the PCR tube deviates from the center line of the PCR tube.

In one embodiment, the nucleic acid amplification element also comprises the PCR reagent bin and the paraffin oil bin, wherein the PCR reagent bin is configured to store the PCR reagent, the paraffin oil bin is configured to store the paraffin oil which is used for heat-sealing of the PCR tube; and the bottom of the PCR reagent bin and the bottom of the paraffin oil bin are both provided with through holes, so that the PCR reagent bin and the paraffin oil bin can be in communication with the reaction chamber respectively.

In one embodiment, the nucleic acid extraction and amplification device further comprises the upper cover and the bottom cover, wherein the upper cover is attached with the waterproof and gas-permeable membrane for gas exchange and biological pollution prevention; the bottom cover is provided with the penetrating area for accommodating the channel turntable, and the PCR tube is connected to the bottom cover; one or more PCR tubes and PCR tube channels are provided; and the nucleic acid extraction element or the nucleic acid amplification element is also provided with the reservation bin which can be in communication with the reaction chamber respectively.

In one embodiment, the driving component can also heat and control the temperature of the nucleic acid extraction and amplification device.

In one embodiment, the machine further comprises the light path component, the vertical movement component and the horizontal movement component; the light path component is configured to perform the fluorescence collection on the amplification results of the nucleic acid extraction and amplification device; the vertical movement component is configured to control the vertical movements of the piston rod and the magnetic rod; and the horizontal movement component is configured to control the forward and backward movement of the vertical movement component.

In one embodiment, the nucleic acid extraction device includes the piston, the reaction chamber and the permanent magnet, wherein the piston is configured to control the flow direction of the fluid in the nucleic acid extraction and amplification device; the reaction chamber is configured to provide the place for the magnetic beads to adsorb, wash and elute the nucleic acids; the permanent magnet is configured to provide the magnetic attraction force for the magnetic beads; and the piston is located outside the reaction chamber.

In one embodiment, the permanent magnet and the piston are separately arranged.

In one embodiment, the permanent magnet and the piston are respectively located at the different positions outside the reaction chamber.

In one embodiment, the piston is located above the reaction chamber.

In one embodiment, the permanent magnet is located below the reaction chamber.

In one embodiment, the permanent magnet is the vertically placed magnetic rod, and the piston, the reaction chamber and the magnetic rod are arranged vertically in sequence from top to bottom.

In one embodiment, the reaction chamber is the recess with the upward opening; and the piston moves vertically in the piston channel, and the piston channel is in communication with the reaction chamber.

In one embodiment, the reaction chamber is located on the channel turntable; and the micro-channel in communication with the reaction chamber is provided in the channel turntable.

In one embodiment, the reaction chamber is the recess with the upward opening that is provided in the center of the channel turntable.

In one embodiment, the size of the lower end of the piston and the size of the lower end of the piston channel are reduced; and when the piston moves downwards to the lowest position, the piston is blocked by the piston channel and cannot enter the reaction chamber.

In one embodiment, when the piston moves downwards to the lowest position, the bottom surface of the piston and the reaction chamber in the center of the channel turntable form the sealed chamber jointly.

In one embodiment, the lower portion of the channel turntable is provided with the cross-shaped fixing element, the central rotating shaft of the fixing element is the hollow cylinder, and the hollow cylinder is the magnetic rod channel for the vertical displacement of the magnetic rod.

In one embodiment, the bottom surface of the reaction chamber is the top end of the magnetic rod channel.

In one embodiment, the lower end of the magnetic rod is provided with the magnetic rod driving mechanism for controlling the vertical displacement of the magnetic rod in the magnetic rod channel; and the upper end of the piston is provided with the piston driving mechanism for controlling the vertical displacement of the piston in the piston channel.

In one embodiment, the piston driving mechanism comprises the vertical movement module and the lateral movement module; the vertical movement module is configured to drive the piston to move vertically; the lateral movement module is configured to realize the combination or separation of the piston and the piston driving mechanism; and the vertical movement module and the lateral movement module are integrally nested and combined.

In one embodiment, the lateral movement module comprises the curved rod structure and the slider structure;

the curved rod structure is located above the slider structure; the curved rod structure rotates to enable the slider structure to move left and right, so as to drive the piston and the driving mechanism to be combined or separated; the curved rod structure comprises the fixed shaft and the rocking handle, one end of the rocking handle is connected to the fixed shaft, and the rocking handle can perform the circular movement around the fixed shaft; the slider structure is provided with the slide rail with the upward opening; the other end of the rocking handle is provided with the connecting rod; and in the process of the circular movement of the rocking handle, when the connecting rod is inserted into the slide rail, the rocking handle rotates to drive, by means of the connecting rod, the slide rail to move, thereby driving the slider structure to move left and right.

In one embodiment, the bottom surface of the slider structure is provided with the arc-shaped notch with the opening; the piston comprises the top cover and the piston rod, and the top cover has the diameter greater than the cross section diameter of the piston rod; when the slider structure gets close to the piston, the open portion of the arc-shaped notch is sleeved on the piston rod, so that the piston is combined with the driving mechanism and moves vertically with the vertical movement module; and the lateral movement module is integrally nested with the vertical movement module by means of the slider structure and can move left and right relative to the vertical movement module.

In one embodiment, the nucleic acid extraction assembly further comprises the pyrolysis bin, the washing bin and the elution bin; the channel turntable can be rotated to enable the micro-channel to be in selective communication with the bottom through hole of the pyrolysis bin, the washing bin or the elution bin, so that the reaction chamber is in selective communication with the pyrolysis bin, the washing bin or the elution bin; the nucleic acid amplification assembly comprises the PCR tube and the PCR tube channel; after the nucleic acid extraction is completed, the channel turntable is rotated to enable the micro-channel to be in selective communication with the PCR tube channel, so that the reaction chamber is in selective communication with the PCR tube; and the PCR tube is detachably connected to the bottom surface of the nucleic acid extraction and amplification device, and the sealed connection can be realized after the connection.

The nucleic acid extraction and detection integrated machine of the disclosure has the following beneficial effects:

(1) the worm gear and worm transmission mechanism of the specific structure can drive the channel turntable to rotate accurately as per the preset rotation angle at the specified time, so as to ensure that the internal micro-channel is connected precisely when needed and disconnected accurately when needed according to the working program settings;

the accurate communication of the micro-pores having the aperture of 600 microns and the micro-channel under the load-speed and low-load conditions of the nucleic acid extractor is achieved, the rotation angle is accurately controlled, the precise rotation at the angle of 35-151 degrees each time is guaranteed, and the problem of sample leakage is avoided; and after the accurate communication of the micro-pores having the aperture of 600 microns and the micro-channel, the stability can be continuously kept, and the precision of the next rotation angle cannot be affected by the vibration caused by the fact that the piston rod vertically drives the piston to move in the working process of the nucleic acid extractor;

(2) two embodiments are provided for arrangement of the reaction chamber, wherein when the piston is located outside the reaction chamber, by skillfully using the characteristic that the rotating shaft rotates without displacement, the groove is formed at the upper central rotating shaft above the channel turntable to serve as the reaction chamber, and the magnetic rod channel for the movement of the magnetic rod is formed at the central rotation axis below the channel turntable, so that the piston, the reaction chamber and the magnetic rod are independent of one another and are arranged in sequence from top to bottom, but the overall dimensions are unchanged, and the structure is still compact;

since the piston, the reaction chamber and the magnetic rod are independent, the magnetic beads can be extracted in the wider cylindrical reaction chamber rather than the narrow annular reaction chamber, the magnetic beads can be more evenly scattered in the samples in the reaction chamber and can be quickly and completely converged when being attracted by the magnetic rod, the dead corners are eliminated, and the efficiency of the processes of nucleic acid adsorption, washing and elution is effectively improved;

the magnetic rod directly attracts the magnetic beads under the reaction chamber, and when the magnetic rod moves upwards to get close to the reaction chamber, the magnetic attraction force is located at the bottom of the reaction chamber, so that the magnetic beads can be quickly gathered at the bottom of the reaction chamber and are more concentrated, more sufficient adsorption, washing and elution are achieved, dead corners are eliminated, and the efficiency of the nucleic acid extraction is improved; and the piston cannot enter the reaction chamber in the pumping and suction process and cannot be in direct contact with the samples and the magnetic beads, and the problems that the samples are bonded to the piston can be avoided, so that the errors are reduced;

(3) two kinds of piston driving mechanisms are provided; when the piston is located inside the reaction chamber, the automatic combination and separation of the piston pushing rod on the nucleic acid extractor and the piston in the consumable are successfully realized by providing the combined movement assembly and the separated movement assembly, so that the automation level of the nucleic acid extractor is further increased, the structure is simple, the design is ingenious, the nucleic acid extraction experiment is more convenient, and the efficiency of the nucleic acid extraction is improved; and when the piston is located outside the reaction chamber, the structure of the piston is improved, the structure of the piston driving mechanism is improved, the automatic combination, the vertical pumping and suction movements and the automatic separation of the piston are successfully realized by providing the vertical movement module and the lateral movement module that are nested with each other, so that the automation level is increased, and the process of the nucleic acid extraction and purification is easier, more convenient and smoother;

(4) the nucleic acid extraction and amplification device (consumable) does not need to be provided with the chamber for storing the waste liquid;

(5) the plurality of PCR tubes are provided, so that the multiple items can be detected at the same time;

(6) the efficiency of the nucleic acid extraction and purification is improved, and the sensitivity and accuracy of the nucleic acid detection is guaranteed;

(7) the PCR tube in the consumable is of the detachable structure, so that the PCR tube can be prepared separately; the wall is thinner, thus the temperature rises quickly during isothermal amplification, and the detection efficiency is greatly improved; and the reaction reagent can be stored in the PCR tube in advance, which is more beneficial to storage and transportation; and (8) the machine is simpler in structure, smaller in size, more complete in function, low in cost, low in energy consumption and convenient to install, debug and maintain, and meets the requirements for miniaturization and portability of the nucleic acid extractor.

DETAILED DESCRIPTION OF THE INVENTION

The preferred embodiments of the disclosure are further described in detail in conjunction with accompanying drawings below, it should be noted that the following embodiments are intended to facilitate the understanding of the disclosure without any limitation, and all features disclosed in the embodiments of the disclosure or steps in all disclosed methods or processes, except for mutually exclusive features and/or steps, can be combined in any way.

Embodiment 1. Nucleic Acid Extraction and Detection Integrated Machine (Piston of Consumable being Located Inside Reaction Chamber) of Disclosure The nucleic acid extraction and detection integrated machine provided in this embodiment is shown in FIGS. 1-2, wherein FIG. 1 is an overall structure diagram of the nucleic acid extraction and detection integrated machine, and FIG. 2 is a split structure diagram of FIG. 1.

Figure 1:
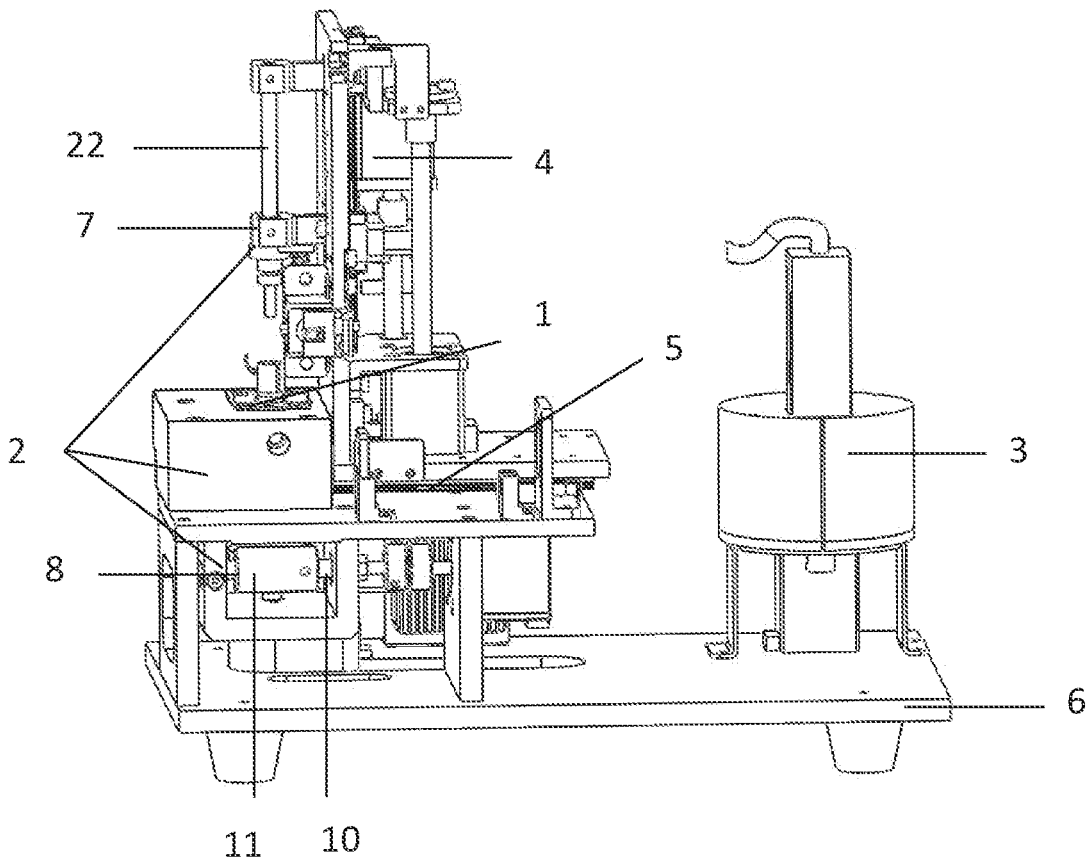
FIG. 1 is an overall structure diagram of a nucleic acid extraction and detection integrated machine in Embodiment 1.
Figure 2:
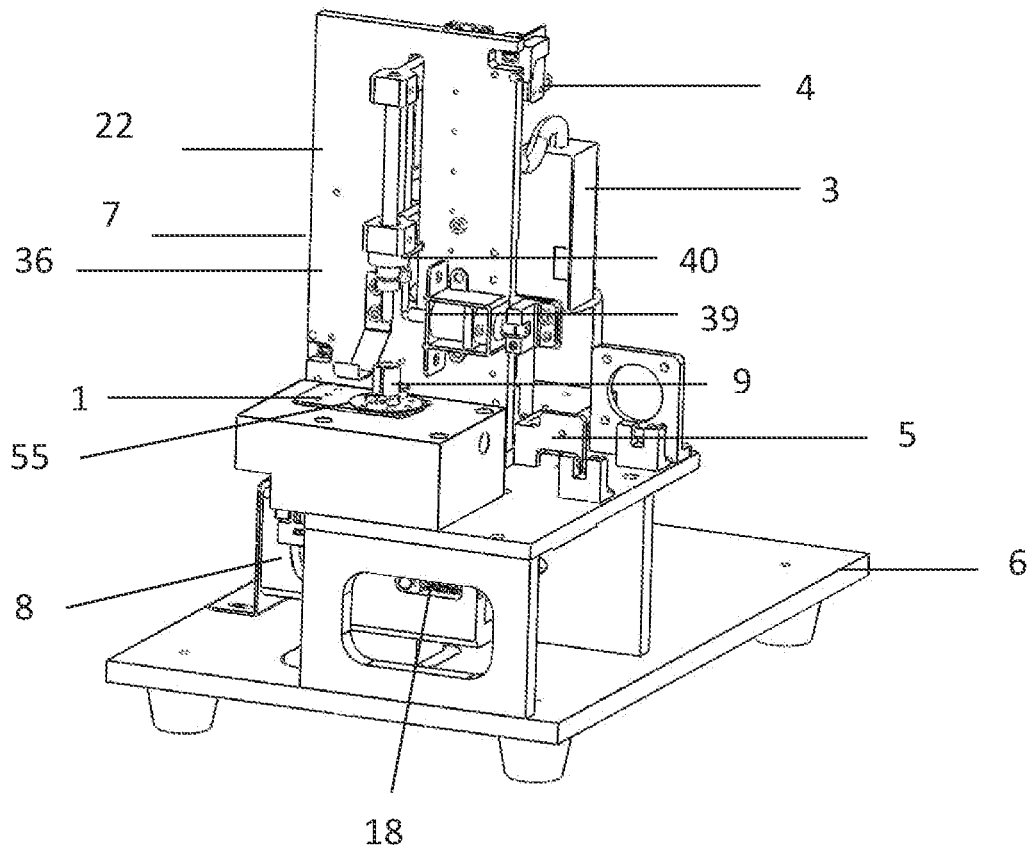
FIG. 2 is a split structure diagram of FIG. 1 in Embodiment 1.
Figure 3:
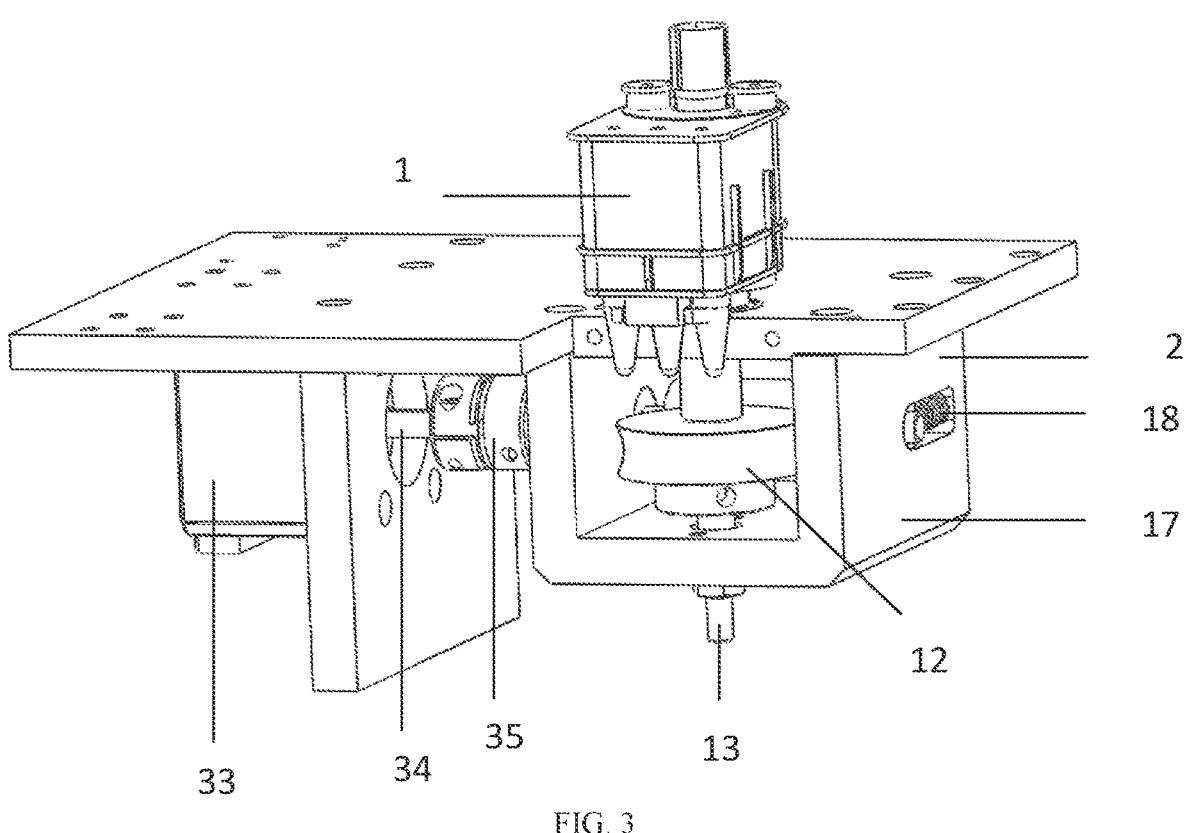
FIG. 3 is a structure diagram of an integrated worm gear and worm transmission mechanism and consumable in Embodiment 1.

The nucleic acid extraction and detection integrated machine of the disclosure is shown in FIG. 1, and mainly comprises a nucleic acid extraction and amplification device 1 (consumable), a driving component 2, a light path component 3, a vertical movement component 4, a horizontal movement component 5 and a bottom plate 6, wherein the nucleic acid extraction and amplification device 1 is configured to extract, purify and amplify nucleic acids in samples; the driving component 2 is configured to carry and drive the nucleic acid extraction and amplification device 1 to operate, and can also heat and control the temperature of the nucleic acid extraction and amplification device 1; the driving component 2 comprises a piston driving mechanism 7 and a worm gear and worm transmission mechanism 8; as shown in FIG. 2, the piston driving mechanism 7 is configured to drive a piston 9 in the nucleic acid extraction and amplification device 1 to move vertically; and the worm gear and worm transmission mechanism 8 is provided with an elastic element capable of resetting, which is configured to provide thrust for a worm shaft 10 to make a worm 11 close to a worm gear 12 so as to eliminate a backlash (FIG. 3). The light path component 3 is configured to perform fluorescence collection on amplification results of the nucleic acid extraction and amplification device 1, so as to acquire detection results; the vertical movement component 4 is configured to control the vertical movements of the nucleic acid extraction and amplification device 1 and a magnetic rod 22; and the horizontal movement component 5 is configured to control the forward and backward movement of the vertical movement component 4. The nucleic acid extraction and amplification device 1 can be made into the low-cost disposable consumable and can also be made into a device that can be disinfected and used repeatedly, and in this embodiment, the nucleic acid extraction and amplification device 1 is the disposable consumable, hereinafter referred to as the consumable 1. The bottom plate 6 provides a supporting frame for a nucleic acid extraction and detection integrated machine.

Figure 4:
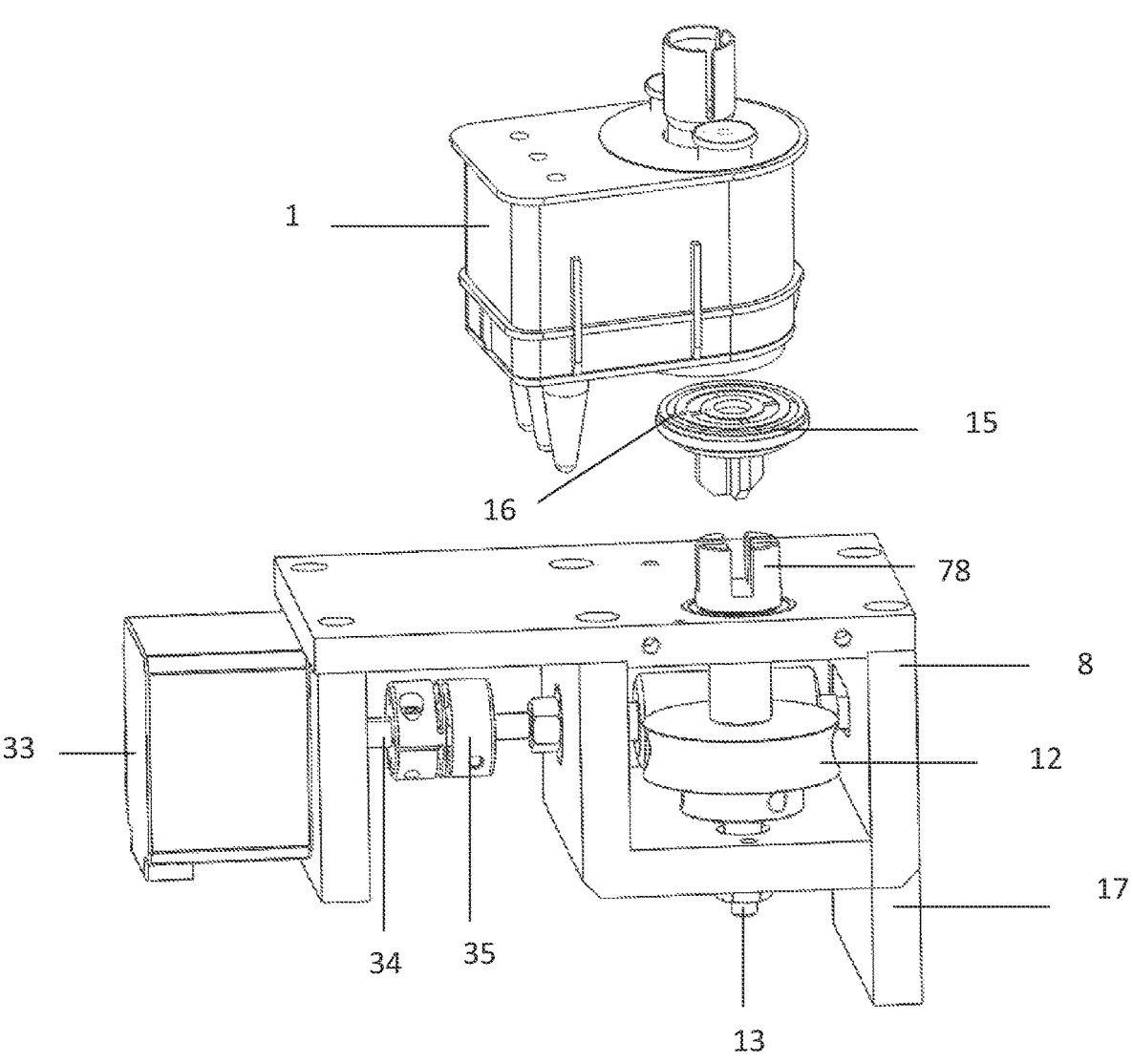
FIG. 4 is an exploded view of FIG. 3 in Embodiment 1.
Figure 5:
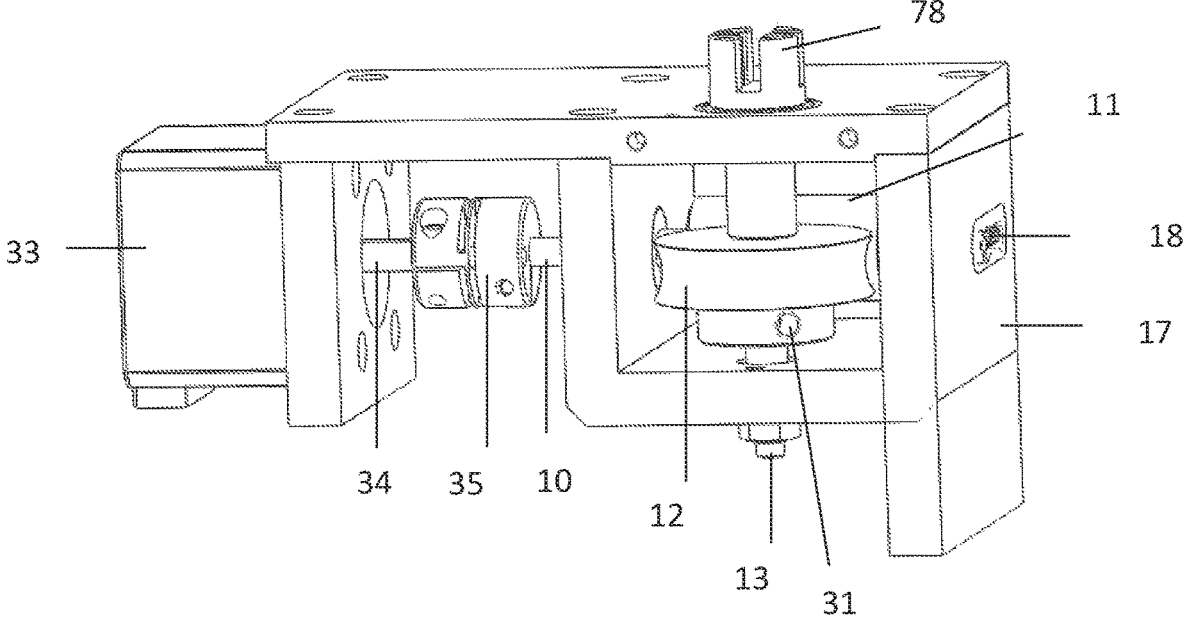
FIG. 5 is an overall structure diagram of a worm gear and worm transmission mechanism for the nucleic acid extraction and detection integrated machine in Embodiment 1.
Figure 6:
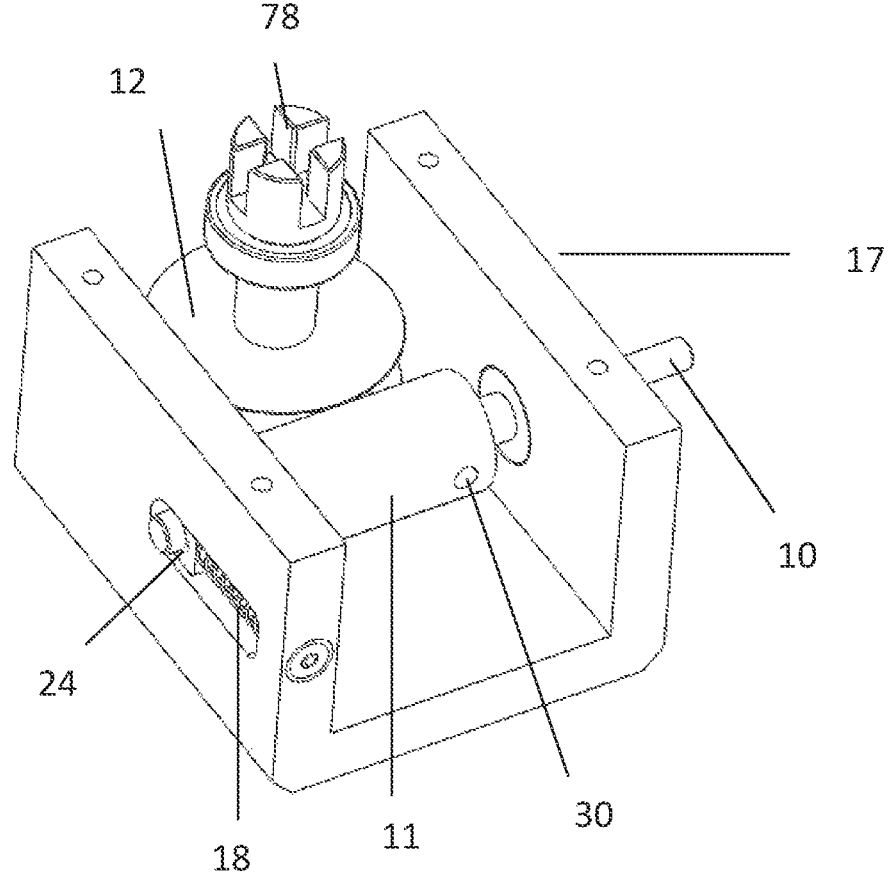
FIG. 6 is a structure diagram of a main body portion of the worm gear and worm transmission mechanism for the nucleic acid extraction and detection integrated machine in Embodiment 1.
Figure 7:
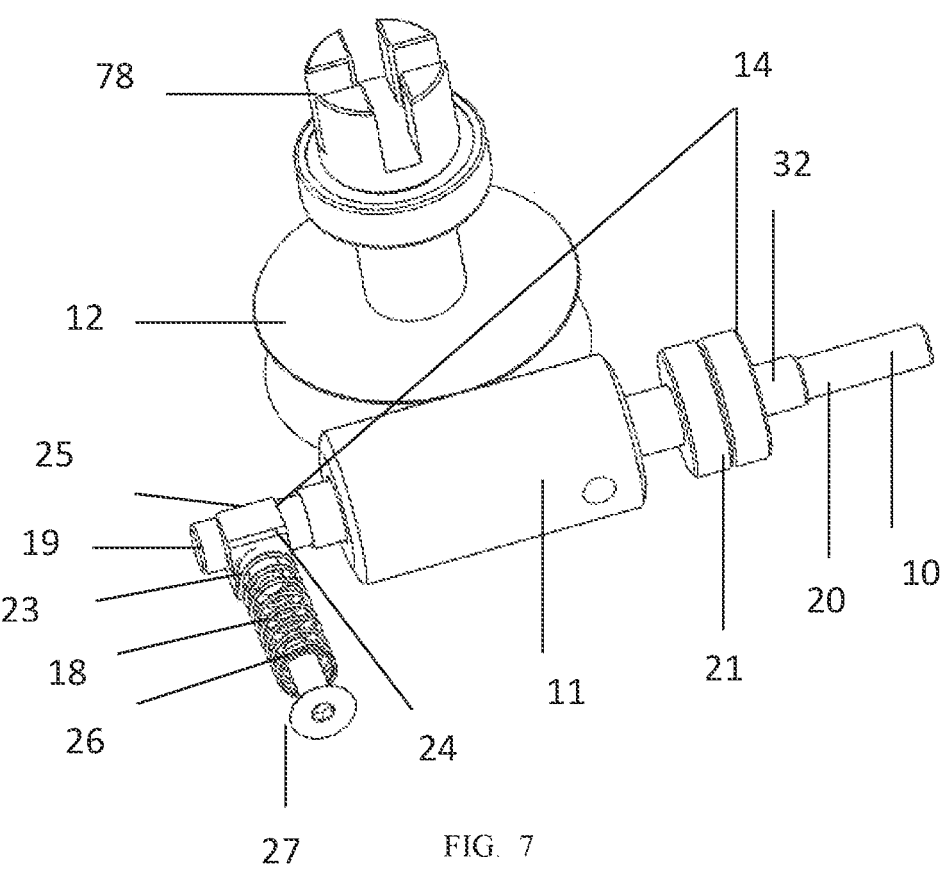
FIG. 7 is a structure diagram of a worm gear and worm anti-backlash mechanism for the nucleic acid extraction and detection integrated machine in Embodiment 1.
Figure 8:
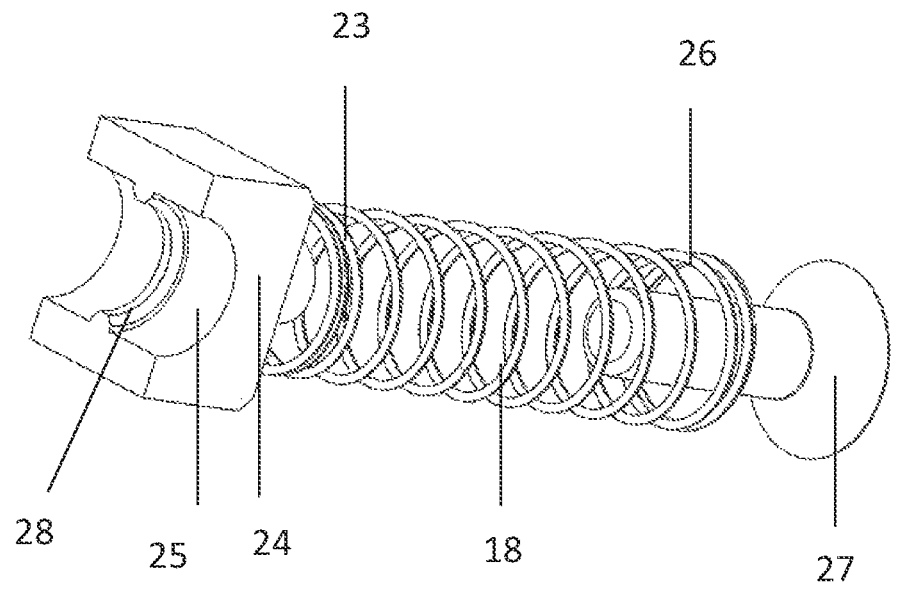
FIG. 8 is a structure diagram of a connecting module, a reset spring and a base thereof in Embodiment 1.
Figure 9:
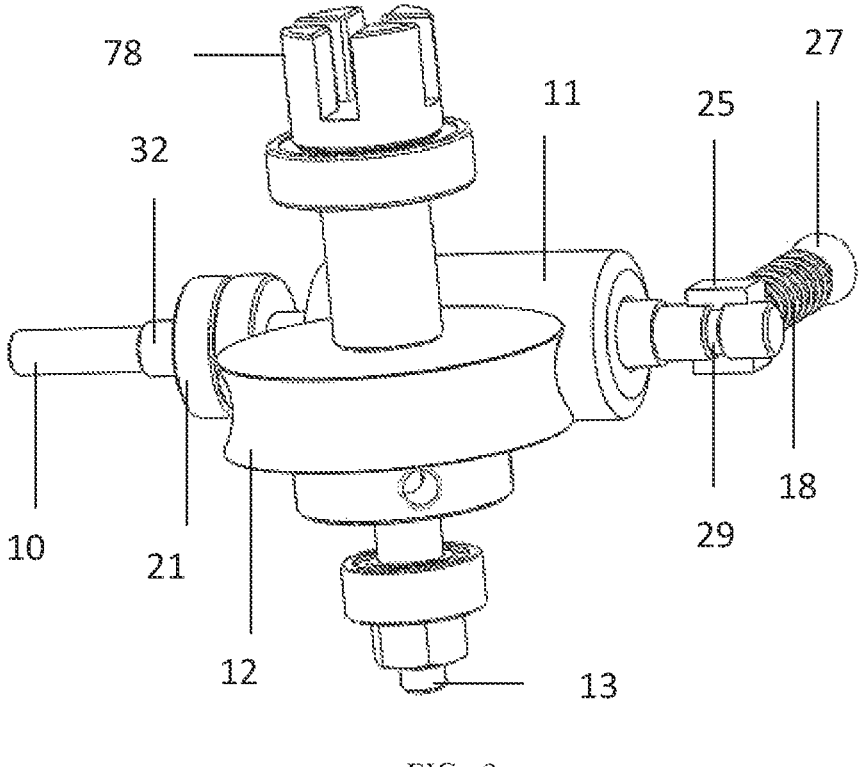
FIG. 9 is a rear view of FIG. 7 in Embodiment 1.

The worm gear and worm transmission mechanism 8 provided in this embodiment is shown in FIGS. 3-9, wherein FIG. 3 is a structure diagram of an integrated worm gear and worm transmission mechanism and consumable, FIG. 4 is an exploded view of FIG. 3, FIG. 5 is an overall structure diagram of the worm gear and worm transmission mechanism for the nucleic acid extraction and detection integrated machine, FIG. 6 is a structure diagram of a main body portion of the worm gear and worm transmission mechanism for the nucleic acid extraction and detection integrated machine, FIG. 7 is a structure diagram of a worm gear and worm anti-backlash mechanism for the nucleic acid extraction and detection integrated machine, FIG. 8 is a structure diagram of a connecting module, a reset spring and a base thereof, and FIG. 9 is a rear view of FIG. 7.

Figure 10:
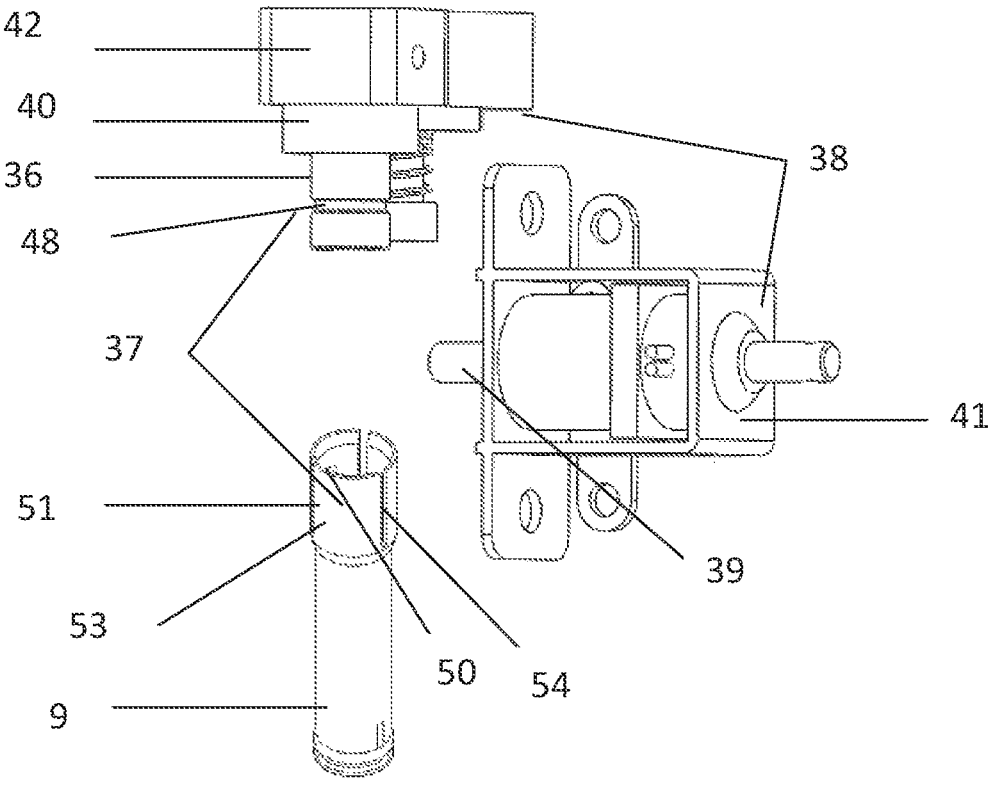
FIG. 10 is a structure diagram of a combined movement assembly and a separated movement assembly in Embodiment 1.
Figure 11:
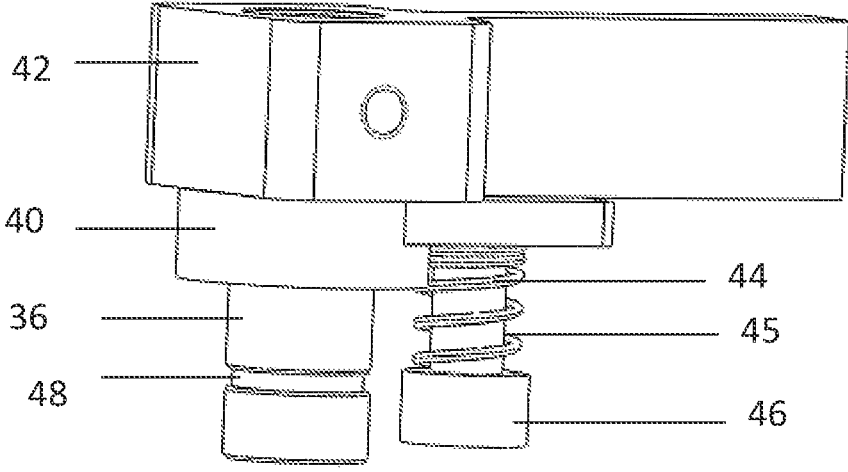
FIG. 11 is a structure diagram of an integrated piston rod, movement module and jacking plate in Embodiment 1.
Figure 12:
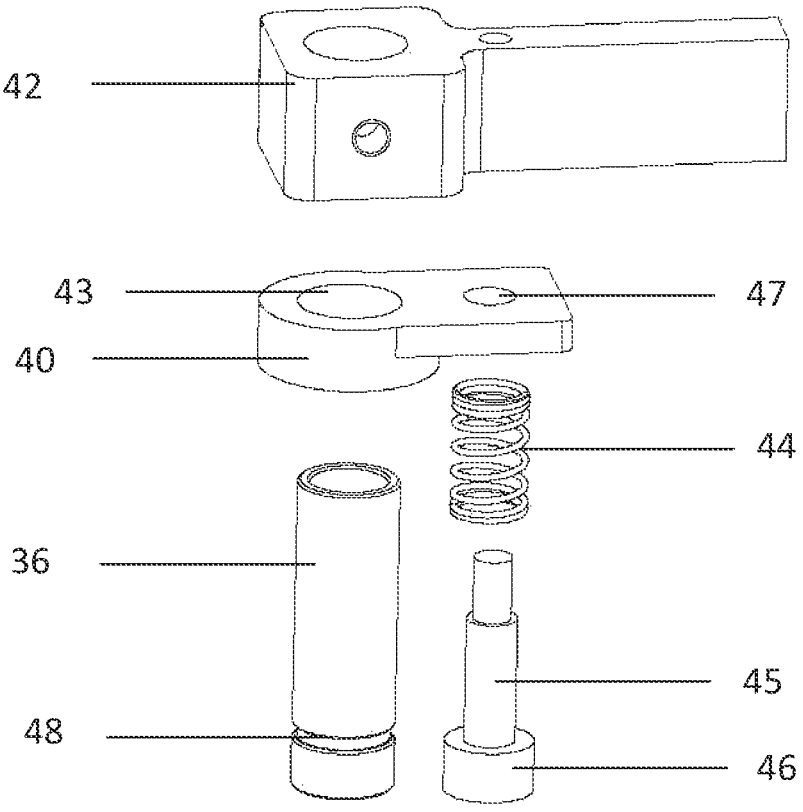
FIG. 12 is an exploded view of an assembly structure of a piston rod, a movement module and a jacking plate in Embodiment 1.
Figure 13:
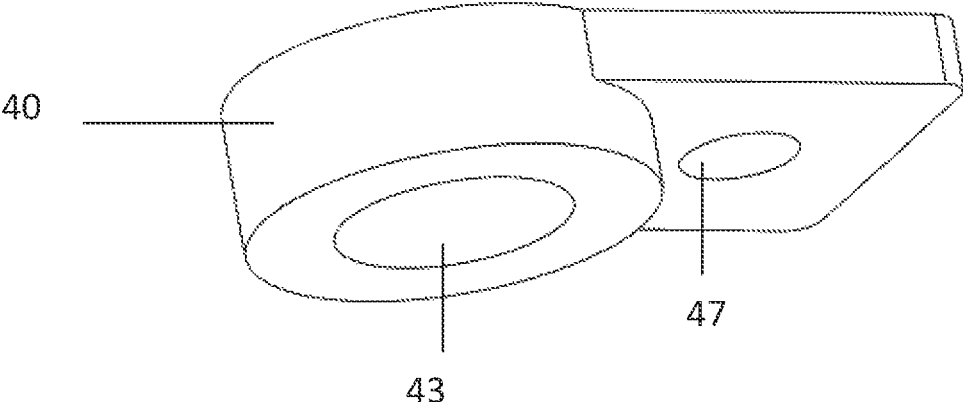
FIG. 13 is a structure diagram of the jacking plate in Embodiment 1.
Figure 14:
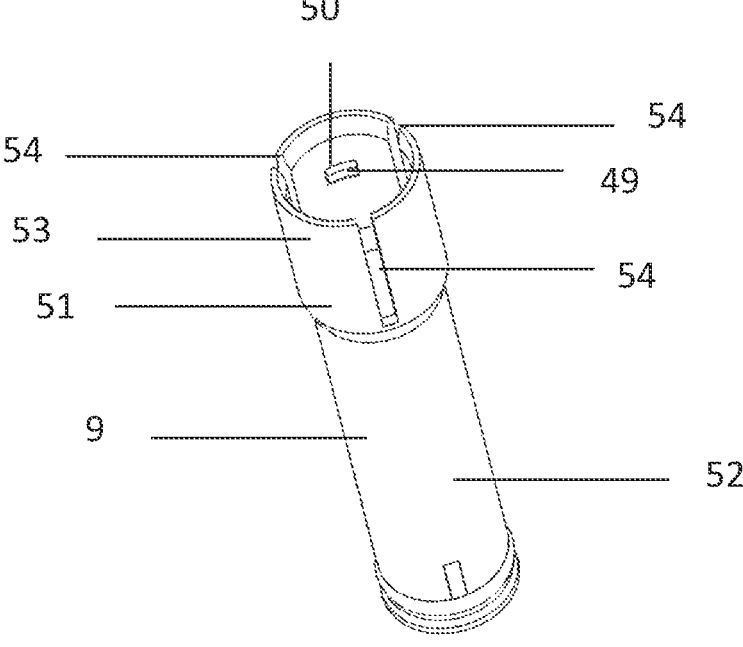
FIG. 14 is a structure diagram of a piston in Embodiment 1.
Figure 15:
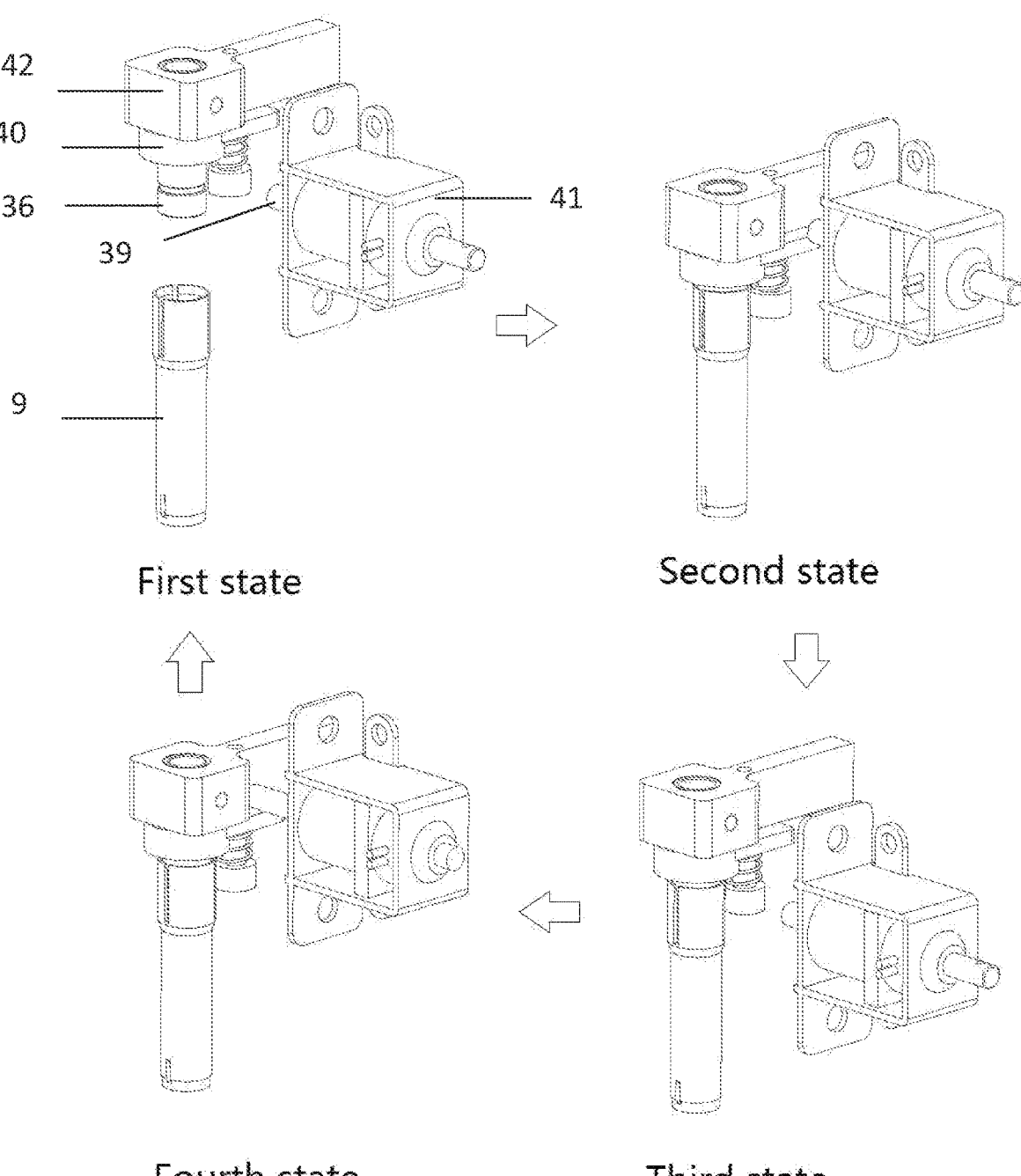
FIG. 15 is a change diagram of combined and separated states of the piston and the piston rod in Embodiment 1.

The piston driving mechanism 7 provided in this embodiment is shown in FIGS. 10-15, wherein FIG. 10 is a structure diagram of a combined movement assembly and a separated movement assembly; FIG. 11 is a structure diagram of an integrated piston rod, movement module and jacking plate; FIG. 12 is an exploded view of an assembly structure of a piston rod, a movement module and a jacking plate; FIG. 13 is a structure diagram of the jacking plate; FIG. 14 is a structure diagram of the piston; and FIG. 15 is a change diagram of combined and separated states of the piston and the piston rod.

Figure 16:
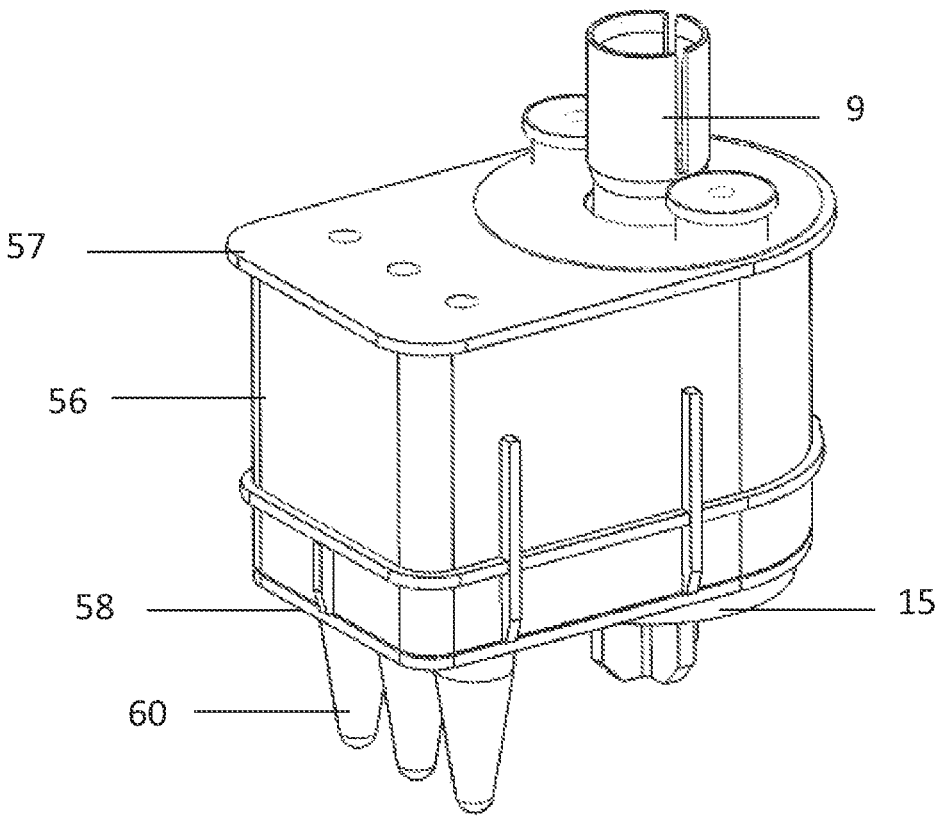
FIG. 16 is an overall structure diagram of a nucleic acid extraction and amplification device in Embodiment 1.
Figure 17:
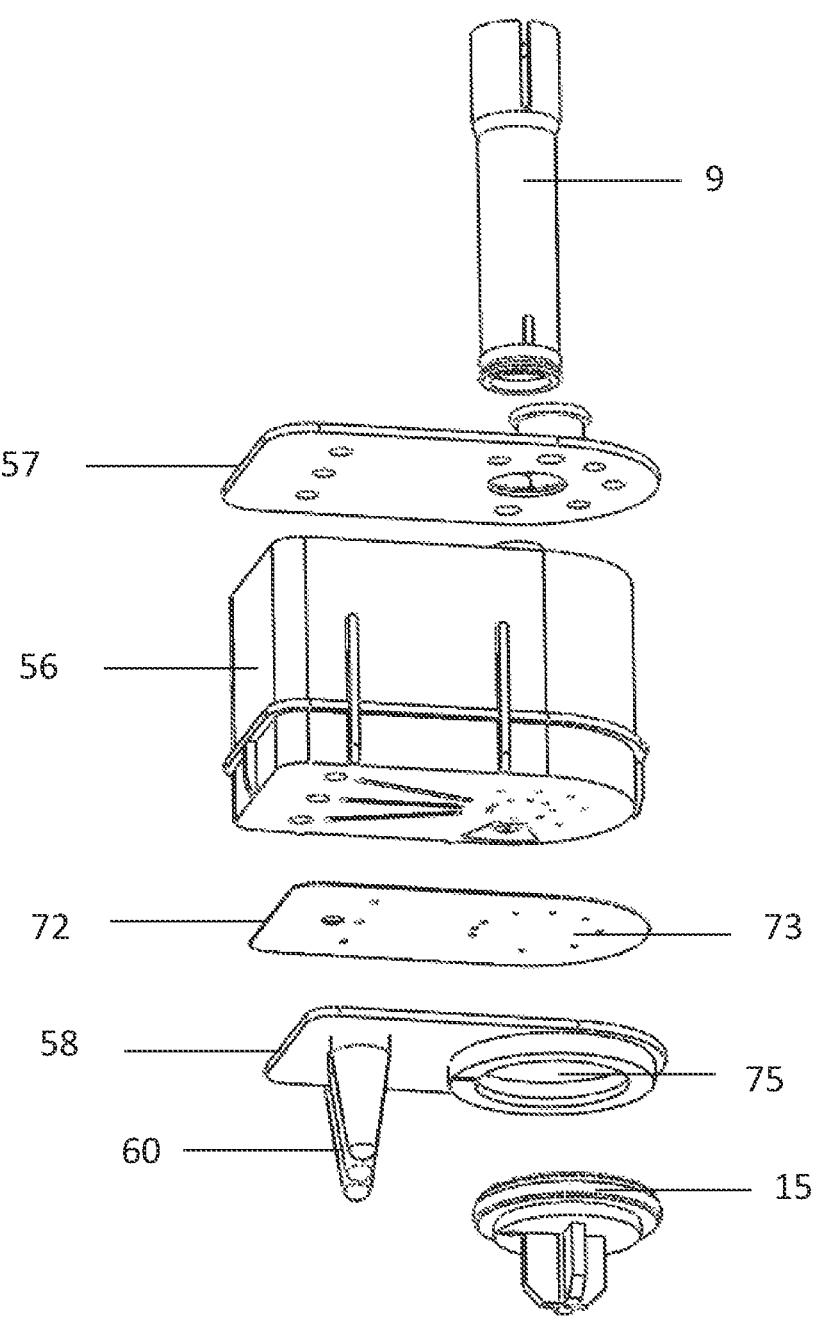
FIG. 17 is an exploded view of the nucleic acid extraction and amplification device in Embodiment 1.
Figure 18:
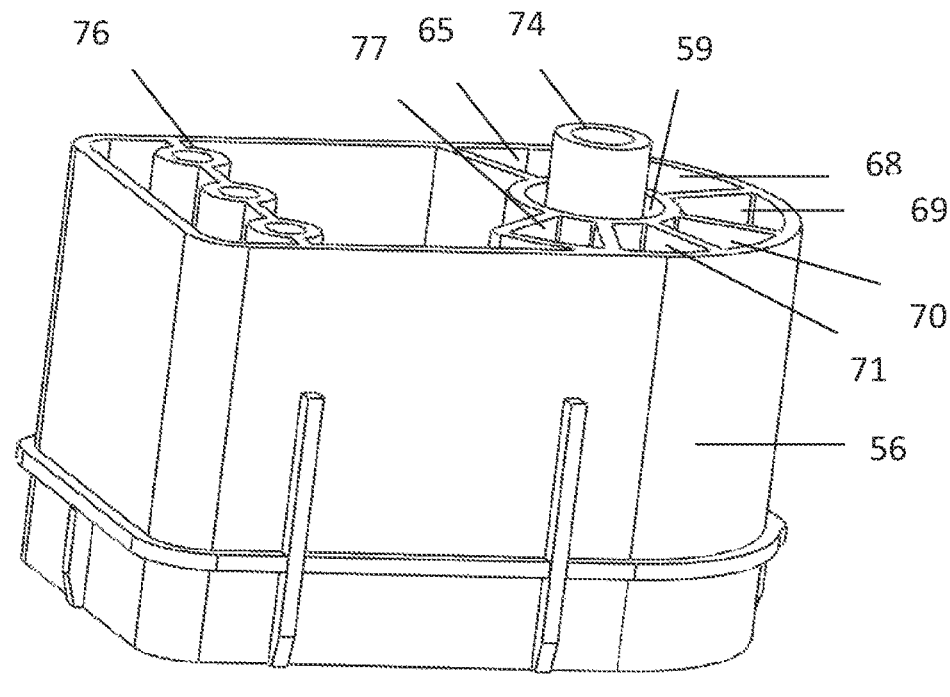
FIG. 18 is a structure diagram of a housing of the nucleic acid extraction and amplification device in Embodiment 1.
Figure 19:
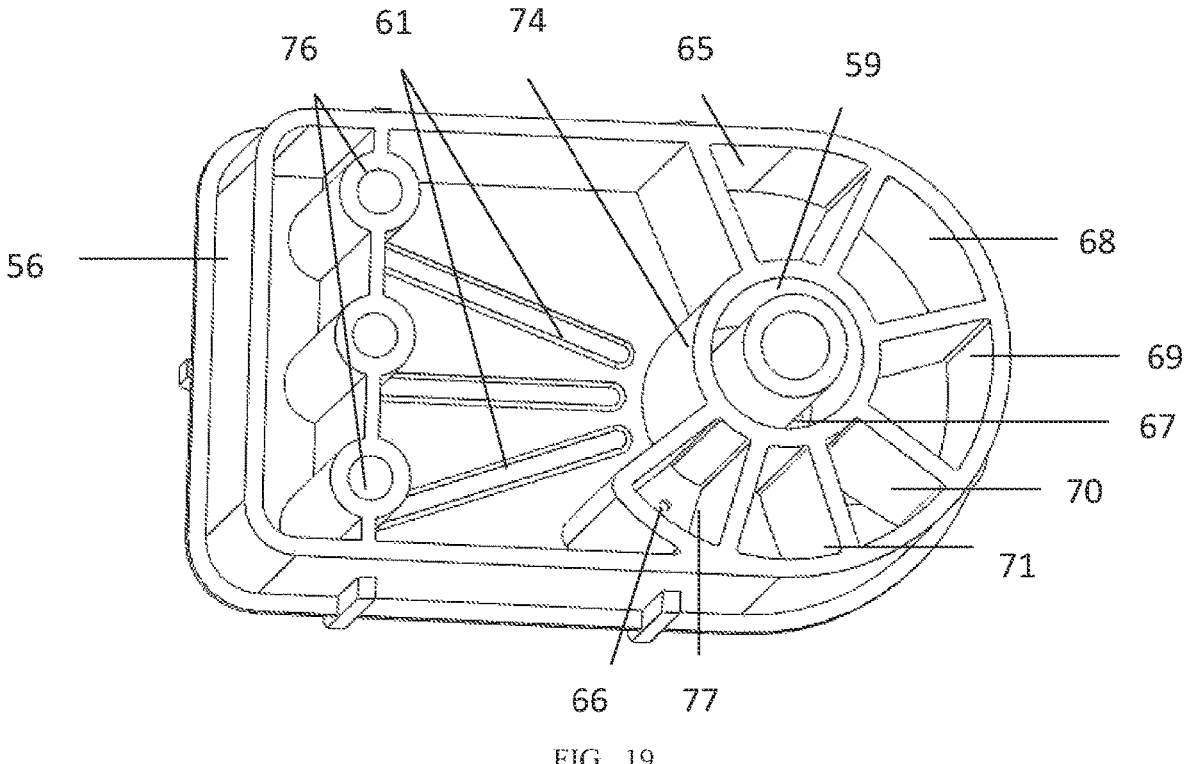
FIG. 19 is an internal structure diagram of the housing in Embodiment 1.
Figure 20A:
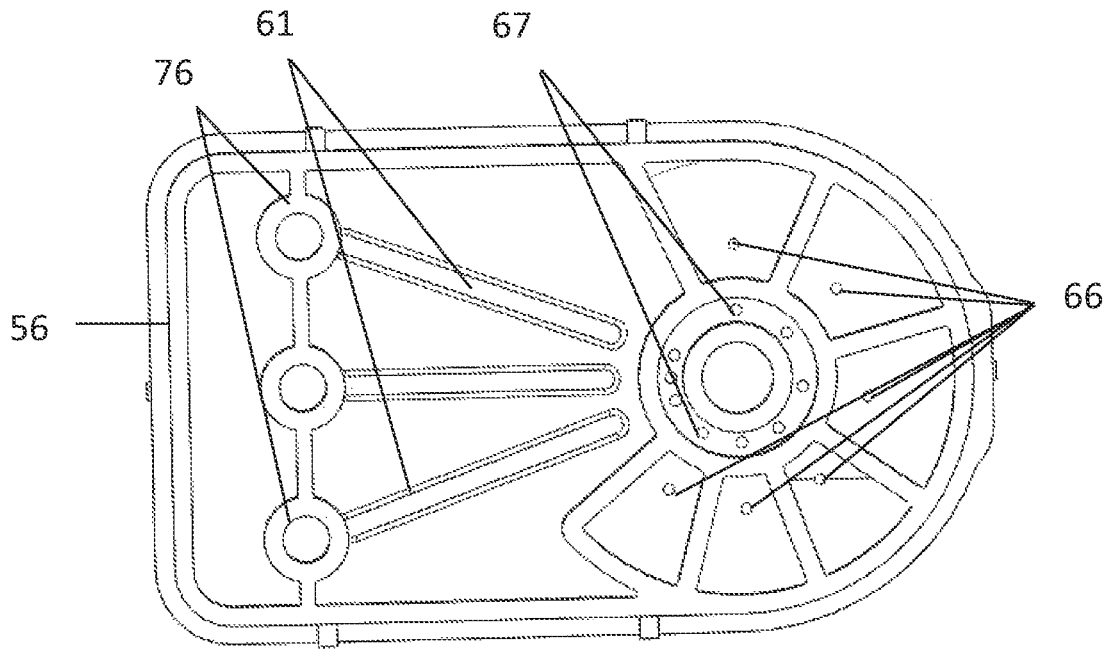
FIG. 20A is a top view of the housing in Embodiment 1.
Figure 20B:
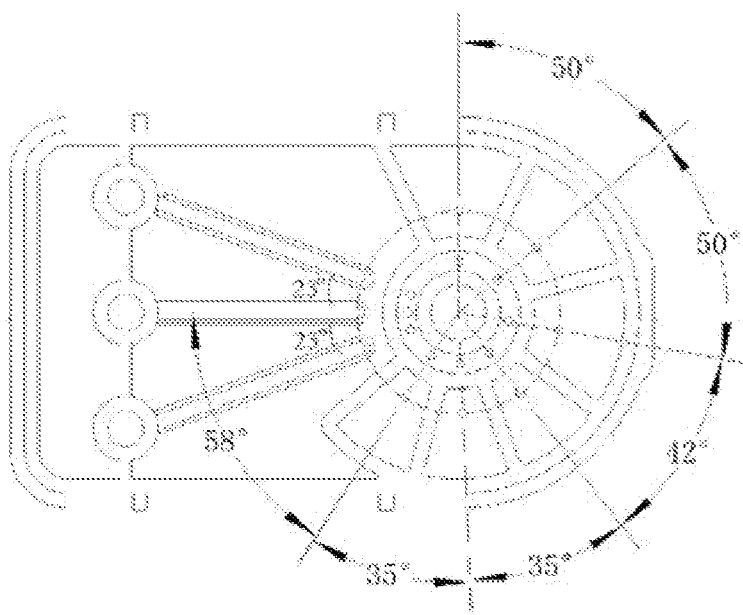
FIG. 20B is a schematic diagram of rotation angles of all chambers of the housing in Embodiment 1.
Figure 21:
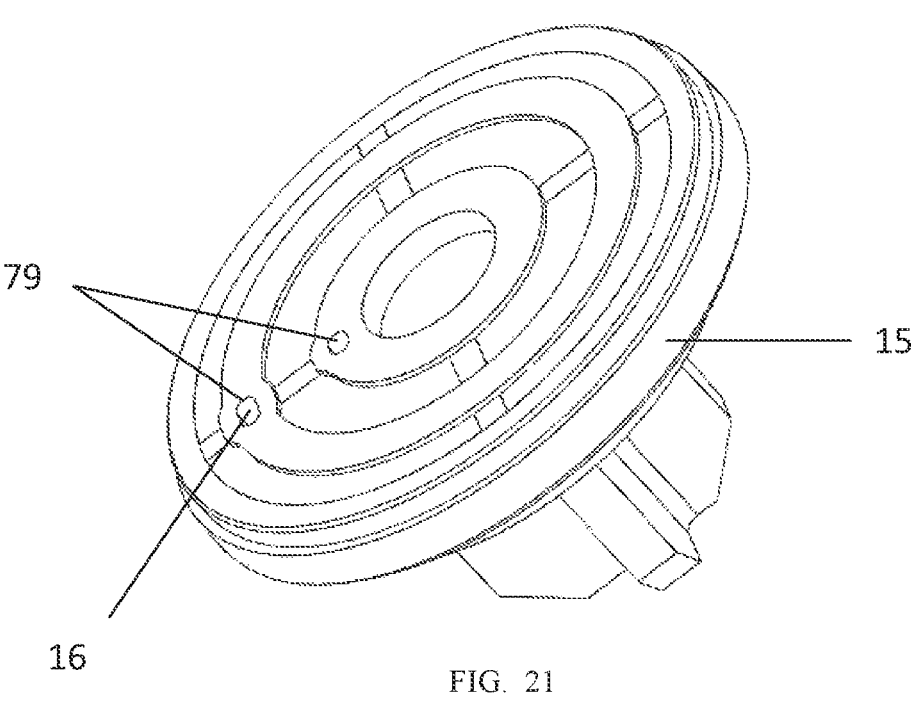
FIG. 21 is a structure diagram of a channel turntable in Embodiment 1.
Figure 22:
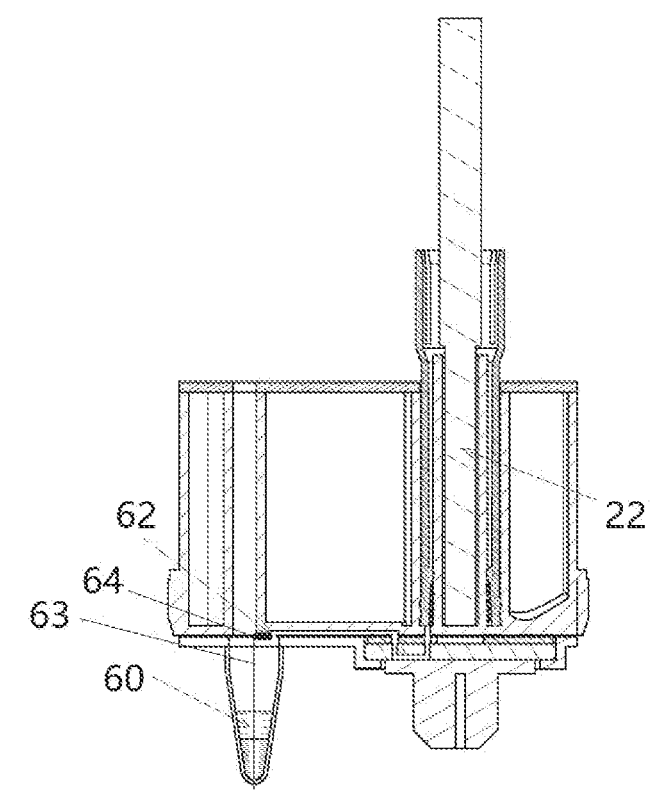
FIG. 22 is a schematic diagram of an inlet position of a PCR tube in Embodiment 1.

The nucleic acid extraction and amplification device 1 provided in this embodiment is shown in FIGS. 16-22, wherein FIG. 16 is an overall structure diagram of the nucleic acid extraction and amplification device; FIG. 17 is an exploded view of the nucleic acid extraction and amplification device; FIG. 18 is a structure diagram of a housing of the nucleic acid extraction and amplification device; FIG. 19 is an internal structure diagram of the housing; FIG. 20A is a top view of the housing; FIG. 20B is a schematic diagram of rotation angles of all chambers of the housing; FIG. 21 is a structure diagram of a channel turntable; and FIG. 22 is a schematic diagram of an inlet position of a PCR tube.

As shown in FIGS. 3-4, in order to achieve the full-automatic, totally-enclosed and integrated operation of nucleic acid extraction and amplification by the nucleic acid extraction and detection integrated machine, it is necessary to drive the channel turntable 15 of the nucleic acid extraction and amplification device 1 to rotate accurately as per a preset rotation angle at the specified time, so as to ensure that a micro-channel (for example, a bottom channel 16 in the channel turntable 15) in the nucleic acid extraction and detection integrated machine is connected precisely when needed and disconnected accurately when needed according to working program settings. The micro-channel in the nucleic acid extraction and detection integrated machine is very narrow, if there is a little error in the rotation angle or the rotation time of the channel turntable 15, the micro-channel may not be connected at the specified time, and thus the nucleic acid extraction or amplification process is interrupted and cannot be carried out normally; therefore, the driving mechanism must be used to achieve the precision control to ensure that the channel turntable rotates accurately as per the preset angle each time without any error. At the same time, the channel turntable 15 has a relatively slow rotation speed and rotates at low speed and low load, and the accurate control on the rotation angle can only be achieved by a transmission device that is most suitable for the low speed and low load and can achieve high-precision transmission, so as to achieve the full automation of the nucleic acid extraction and amplification. Regarding the nucleic acid extraction and detection integrated machine of the disclosure, the accurate control on the rotation angle of the channel turntable 15 of the nucleic acid extraction and detection integrated machine is achieved in a way of simpler structure and lower cost by using the improved worm gear and worm transmission mechanism 8 and mainly by providing the worm gear and worm anti-backlash mechanism 14 (FIG. 7), and in addition, the machine is simple in structure, low in cost and convenient to install, debug and maintain.

As shown in FIG. 5, the worm gear and worm transmission mechanism 8 for the nucleic acid extraction and detection integrated machine in this embodiment comprises the worm gear 12, a worm gear shaft 13, the worm 11, the worm shaft 10, the worm gear and worm anti-backlash mechanism 14, and a bracket 17 configured to fix the worm gear 12, the worm 11 and the worm gear and worm anti-backlash mechanism 14. The worm gear and worm anti-backlash mechanism 14 comprises the reset spring 18, which is mainly configured to provide thrust for the worm shaft 10 to make the worm 11 close to the worm gear 12 so as to eliminate a backlash. The reset spring 18 is located at a first end 19 of the worm shaft 10, and a second end 20 of the worm shaft 10 is flexibly fixed by means of an angular contact bearing 21. Due to the characteristics of the angular contact bearing 21, the second end 20 of the worm shaft 10 has certain flexibility along the shaft center.

As shown in FIG. 8, a first end 23 of the reset spring 18 is movably connected to the worm shaft 10 by means of the connecting module 24, and the connecting module 24 is provided with an arc-shaped recess 25 and is in direct contact with the worm shaft 10 by means of the arc-shaped recess 25, so that the worm shaft 10 will not be affected by the friction force during rotation. In this embodiment, the arc-shaped recess 25 is a semi-circular recess, which is convenient to connect and remove. The connecting module 24 is made of self-lubrication material POM which is low in friction coefficient and low in cost, thus free rotation of the worm shaft 10 can be achieved without adding lubricating oil and the like in the use process, the worm shaft will not be affected by the friction force in the rotation process, and the wear is reduced as much as possible. A second end 26 of the reset spring 18 is fixed to the base 27. The arc-shaped recess 25 is provided with an arc-shaped rib 28 matching with an arc-shaped groove 29 (FIG. 9) in the worm shaft 10, thus the connecting module 24 is fixed, thereby preventing the left-and-right displacement from affecting the anti-backlash effect. The elastic modulus of the reset spring 18 can be calculated according to the driving force required to drive the worm gear 12 and the worm 11 for gapless transmission; the excessively high elastic modulus of the reset spring 18 will result in increase of the rotating friction force of the worm shaft 10 and reduction of the rotation speed, which affects the transmission accuracy; and the excessively low elastic modulus of the reset spring 18 will result in reduction of the anti-backlash effect of the worm gear 12 and the worm 11, which also affects the transmission accuracy. The elastic modulus of the reset spring 18 in this embodiment needs to reach 0.5-1.0 N/m², the transmission accuracy is high at this moment, the anti-backlash effect of the worm gear 12 and the worm 11 is optimal, and the rotation angle of the channel turntable 15 in a nucleic acid extractor can be accurately controlled at the specified time.

As shown in FIGS. 5-7, the worm 11 is locked on the worm shaft 10 by means of a set screw 30, and the worm gear 12 is locked on the worm gear shaft 13 by means of a set screw 31. The angular contact bearing 21 is pressed into the bracket 17 in a shrink-fit manner, and the second end 20 of the worm shaft 10 is locked on the angular contact bearing 21 by means of a lock nut 32; and the base 27 of the reset spring 18 is fixed to the bracket 17. Of course, the angular contact bearing 21 can also be fixed to the bracket by pressing two sides of the angular contact bearing by means of bearing end caps, and then is further fixed by means of screws; and the manner of pressing the angular contact bearing into the bracket 17 in the shrink-fit manner in this embodiment is more convenient and easier to operate and control.

As shown in FIG. 5, the worm gear and worm transmission mechanism 8 for the nucleic acid extractor in this embodiment further comprises a motor 33 which can drive a motor shaft 34 to rotate; the worm shaft 10 is connected to the motor shaft 34 by means of a coupling 35; and the coupling 35 is a diaphragm coupling having flexibility. The motor 33 drives the motor shaft 34 to rotate, the motor shaft 34 drives, in a high-precision and rotation-gap-free manner, the worm shaft 10 to rotate by means of the diaphragm coupling 35 and then drives the worm gear 12 by means of the worm 11, the worm gear 12 rotates to drive the channel turntable 15 in the nucleic acid extraction consumable 1 to rotate, thus the rotation angle is accurately controlled, and the full-automatic, totally-enclosed and integrated operation of nucleic acid extraction and amplification is achieved.

As shown in FIG. 10, the nucleic acid extraction and detection integrated machine provided in this embodiment needs to achieve the extraction, purification and amplification of the nucleic acids by means of the consumable 1, the piston rod 36 in the nucleic acid extraction and detection integrated machine is mainly configured to drive the piston 9 in the consumable 1 to perform the vertical pumping and suction movement, and the pumping and suction force generated changes the air pressure in each area of the consumable 1, so as to control fluids in the consumable 1 to flow among different areas.

As shown in FIGS. 10-14, the piston driving mechanism 7 provided in this embodiment is configured to achieve the automatic docking of the piston rod 36 of the nucleic acid extraction and detection integrated machine with the piston 9 of the consumable 1. The piston driving mechanism 7 comprises the combined movement assembly 37 and the separated movement assembly 38; the combined movement assembly 37 can combine the piston 9 with the piston rod 36, thereby enabling the piston rod 36 to drive the piston 9 to move vertically; and the separated movement assembly 38 prevents the piston 9 from moving by ejecting a push rod 39, thereby enabling the piston 9 to be separated from the piston rod 36 that moves continuously. The separated movement assembly 38 in this embodiment further comprises the jacking plate 40, the ejected push rod 39 can prevent the jacking plate 40 from moving upwards, and under the restriction of the jacking plate 40, the piston 9 stops moving upwards, thus enabling the piston 9 to be separated from the piston rod 36 that moves upwards continuously.

The jacking plate 40 is of a plate structure, the push rod 39 is just across the jacking plate 40 when being ejected, making the jacking plate 40 impossible to move upwards continuously, and the piston 9 below the jacking plate 40 is also blocked by the jacking plate 40, making the piston impossible to move upwards continuously together with the piston rod 36, causing the piston 9 to be separated from the piston rod 36 that moves upwards continuously.

Preferably, the push rod 39 is controlled by an electromagnet 41 to be ejected or retracted, the push rod 39 is ejected when the electromagnet 41 is energized in one direction, and the push rod 39 is retracted when the electromagnet 41 is energized in the opposite direction. The electromagnet 41 generates the magnetism when being energized in one direction, so that the push rod 39 is pushed out due to the fact that like magnetic poles repel each other; and the electromagnet 41 generates the opposite magnetism when being energized in the other direction, so that the push rod 39 is retracted due to the fact that unlike magnetic poles attract each other.

Preferably, the vertical movements of the piston 9 and the piston rod 36 are controlled by the movement module 42, and the jacking plate 40 is arranged below the movement module 42 and can move vertically with the movement module 42. The movement module 42 is controlled by the motor in the nucleic acid extraction and detection integrated machine to move vertically so as to drive the piston rod 36, and the piston rod 36 drives the piston 9 to move vertically together.

Preferably, the piston rod 36 penetrates through the jacking plate 40 to be integrally connected with the movement module 42, and the jacking plate 40 is movably sleeved on the piston rod 36 from bottom to top. The piston rod 36 is of a cylindrical rod structure, the piston rod 36 and the movement module 42 are integrally connected, and the piston rod moves vertically with the movement module 42; and the jacking plate 40 is provided with a first round through hole 43 whose diameter matches that of the cross section of the cylinder of the piston rod 36, so that the jacking plate 40 can be sleeved on the piston rod 36 from bottom to top. A spring 44 is arranged below the jacking plate 40; when the push rod 39 is ejected to prevent the jacking plate 40 from moving upwards, the spring 44 is compressed; and when the push rod 39 is retracted, the spring 44 is restored to push the jacking plate 40 to return upwards.

Preferably, the spring 44 is sleeved on a slide rod 45, the slide rod 45 penetrates through the jacking plate 40 to be connected to the movement module 42, the jacking plate 40 can move vertically along the slide rod 45, a base 46 is arranged below the slide rod 45, and the base 46 has a diameter larger than that of the spring 44. After the jacking plate 40 is sleeved on the piston rod 36 from bottom to top, the other side of the jacking plate 40 is provided with a second round through hole 47 whose diameter matching that of the slide rod 45, the slide rod 45 is sleeved with the spring 44, and the lower end of the spring 44 is fixed by the base 46. The spring 44 and the slide rod 45 are used together to support the jacking plate 40. The slide rod 45 has a certain length, and the length of the slide rod 45 determines the maximum distance of the jacking plate 40 from the movement module 42. When the push rod 38 extends, the jacking plate 40 is blocked such that it cannot move upwards continuously with the movement module 42, thus the piston 9 is prevented from moving upwards continuously with the piston rod 36, and the piston 9 is separated from the piston rod 36. The slide rod 45 provides the sufficient length to ensure that the jacking plate 40 leaves the movement module 42 and the piston 9 and piston rod 36 are separated, that is, during the period that the jacking plate 40 is blocked and the slide rod 45 continues to move upwards with the movement module 42, the piston 9 and the piston rod 45 can be separated, so that the condition that the piston 9 and the piston rod 45 are not separated yet when the jacking plate 40 is located at the bottom of the slide rod 45 can be avoided.

Preferably, the combined movement assembly 37 comprises a groove 48 formed in an outer wall of the piston rod 36 and a rib 49 arranged on an inner wall of the piston 9; and when the piston rod 36 moves downwards to be inserted into the piston 9, the groove 48 can match with the rib 49, so that the piston 9 and the piston rod 36 are combined. In this embodiment, the groove 48 in the outer wall of the piston rod 36 is an annular groove surrounding the circumference of the piston rod 36; and the rib 49 on the inner wall of the piston 9 may be an annular rib surrounding the circumference, or may be composed of a plurality of small ribs 50 arranged symmetrically in an axial direction, which is preferred in this embodiment.

Preferably, the piston 9 is the hollow cylinder, and an upper end 51 of the piston has a cross section diameter larger than that of a lower end 52 and matching or consistent with that of the piston rod 36, so that the piston rod 36 and the upper end 51 of the piston can be closely combined.

Preferably, a cylindrical wall 53 of the upper end 51 of the piston is provided with a longitudinal open groove 54, when the piston rod 36 is inserted into the open groove, the cross section diameter of the upper end 51 of the piston can be increased under the effect of the open groove 54, and thus the piston rod 36 can be conveniently inserted into the piston 9 and combined with the rib 49 by means of the groove 48.

The configuration of the open groove 54 provides an elastic space for outward expansion for the cross section diameter of the cylindrical wall 53 of the upper end 51 of the piston. When the piston rod 36 is inserted, the piston rod 36 makes the cylindrical wall 53 of the piston 9 slightly expand around under the action of the open groove 54, so as to facilitate the smooth insertion of the piston rod 36; and after the groove 48 of the piston rod 36 matches with the rib 49 of the piston 9, the original diameter of the cylindrical wall 53 of the upper end 51 of the piston is restored, so that the piston rod 36 and the upper end 51 of the piston are closely combined. At least one open groove 54 is provided, and three open grooves 54 are provided in this embodiment.

As shown in FIG. 15, the piston rod 36 and the piston 9 in the nucleic acid extraction and detection integrated machine provided in this embodiment have four states as follows: in the first state which is the initial state, the disposable consumable 1 is placed into a corresponding recess 55 of the driving component 2 of the nucleic acid extraction and detection integrated machine, and the piston rod 36 and the movement module 42 are far away from the piston 9 at this moment; in the second state which is the combined state of the piston rod 36 and the piston 9, with downward movement of the movement module 42, the piston rod 36 moves downwards and is combined with the cylindrical wall 53 of the upper end 51 of the piston, and the groove 54 of the piston rod 36 matches with the rib 49 of the piston 9; in the third state which is the working state, the movement module 42 drives the piston rod 36 and the piston 9 to perform the vertical pumping and suction movements, so as to control the fluids in the consumable 1 to flow among the different areas; and in the fourth state which is the separated state of the piston rod 36 and the piston 9, the movement module 42 drives the piston rod 36 to move upwards at this moment, the electromagnet 41 is energized to eject the push rod 39, and the push rod 39 is located above the jacking plate 40 to prevent the jacking plate 40 from moving upwards continuously, thereby preventing the piston 9 from being separated tom the piston rod 36 that moves upwards continuously.

FIGS. 16, 17 and 18 shows that the nucleic acid extraction and amplification device 1 (hereinafter referred to as the consumable) of the nucleic acid extraction and detection integrated machine provided in this embodiment is mainly composed of the housing 56 provided with a plurality of chambers, an upper cover 57 above the housing 56 and a bottom cover 58 below the housing 56. The consumable 1 comprises a nucleic acid extraction element, the reaction chamber 59 and a nucleic acid amplification element; the nucleic acid extraction element is configured to add or store reagents required by the nucleic acid extraction and washing and a waste liquid generated; the reaction chamber 59 is the place where nucleic acid extraction takes place, and the reaction chamber 59 can be in selective communication with the nucleic acid extraction element or the nucleic acid amplification element to realize fluid exchange or mixing respectively; and the nucleic acid amplification element contains the PCR tube 60 and a PCR tube channel 61, and the PCR tube channel 61 at the inlet 62 of the PCR tube 60 deviates from a center line 63 of the PCR tube 60 (FIG. 22).

The term "fluid exchange" here refers to that the fluid can flow from one place to another and may pass through some physical structures to play a guiding role in the flow process. Passing through the physical structures generally means that the fluid passes through surfaces of the physical structures or internal spaces of the structures to passively or actively flow to another place; the passivity generally refers to the flow caused by an external force, for example, the flow under pressure. In the present utility model, it specifically means that the fluid can enter the reaction chamber from the nucleic acid extraction element and can also enter the nucleic acid extraction element or the nucleic acid amplification element from the reaction chamber and the fluid can be switched repeatedly between the different chambers.

The term "selective" here means that when the reaction chamber is in fluid communication with the nucleic acid extraction element, the nucleic acid amplification element is not in fluid communication with the reaction chamber, and when the nucleic acid amplification element is in fluid communication with the reaction chamber, the reaction chamber is not in fluid communication with the nucleic acid extraction element, that is, the reaction chamber is in selective fluid communication with the nucleic acid extraction element at a proper time and is in selective fluid communication with the nucleic acid amplification element at another proper time.

A fluid inlet 62 of the PCR tube 60 deviating from the center line 63 means that the fluid does not enter the PCR tube 60 from the center 64 of a tube port, but needs to deviate from the center 64 and enter from the position close to one side of the PCR tube 60, and cannot directly enter along a tube port wall. Since an inner wall of the tube port of the PCR tube 60 needs to be subjected to hydrophobic treatment, the fluid cannot enter directly along the tube port wall; however, if the fluid enters from the middle of the tube port, fluid sputtering occurs very easily, which affects the detection sensitivity; when the fluid enters from the position deviating from the center 64 of the tube port, the fluid can be in contact with part of the inner wall of a lower side of the PCR tube 60 in the falling process and then flows downwards along the inner wall, which obviously reduces the fluid sputtering and ensures that the inner wall near the tube port is not stained with the fluid, thereby ensuring the more accurate detection result. In this embodiment, the fluid drops from the fluid inlet 62 of the PCR tube 60 to the inner wall at the height of ⅔ of the PCR tube, and then flows downwards along the inner wall.

As shown in FIG. 19 and FIG. 20, the nucleic acid extraction element comprises a pyrolysis bin 65 and a washing bin; the pyrolysis bin 65 is configured to store the samples, a pyrolysis liquid and magnetic beads; the washing bin is configured to store a washing liquid; one or more washing bins are provided; and the bottom of the pyrolysis bin 65 and the bottom of the washing bin are both provided with through holes 66, which can be in communication with a through hole 67 of the reaction chamber 59 respectively.

Preferably, the washing bin comprises a primary washing bin 68 and a secondary washing bin 69, which are respectively applied to first washing and second washing of the samples after pyrolysis, and the bottom of the primary washing bin 68 and the bottom of the secondary washing bin 69 are both provided with the through holes 66, which can be in communication with the through hole 67 of the reaction chamber 59.

Preferably, the nucleic acid amplification element also comprises a PCR reagent bin 70 and a paraffin oil bin 71, wherein the PCR reagent bin 70 is configured to add or store a PCR reagent, and the paraffin oil bin 71 is configured to add or store paraffin oil which is used for heat-sealing of the PCR tube; and a bottom of the PCR reagent bin 70 and a bottom of the paraffin oil bin 71 are both provided with through holes 66, which can be in communication with the through hole 67 of the reaction chamber 59 respectively.

Preferably, the nucleic acid extraction and amplification device provided in this embodiment further comprises the channel turntable 15 which is provided with the bottom channel 16 (FIG. 21); and the channel turntable 15 can be rotated to enable the reaction chamber 59 to be in communication with the pyrolysis bin 65, the primary washing bin 68, the secondary washing bin 69, the PCR reagent bin 70, the paraffin oil bin 71 or the PCR tube channel 61 respectively by means of the bottom channel 16. In this embodiment, the channel turntable 15 is only provided with one bottom channel 16 capable of being in communication, so that the reaction chamber 59 can only be in communication with one chamber by means of the bottom channel 16 each time.

Preferably, the nucleic acid extraction and amplification device provided in this embodiment further comprises a film 72 which is provided with through holes 73 in communication with the reaction chamber 59, the nucleic acid extraction element and the nucleic acid amplification element, wherein the through hole 73 of the film 72 at the inlet 62 of the PCR tube 60 deviates from the center line 63 of the PCR tube 60. The through holes 73 in the film 72 are used as a part of a fluid channel, and the PCR tube channel 61 can be led to the inlet 62 of the PCR tube 60.

Preferably, the reaction chamber 59 is provided with the piston 9, and the displacement of the piston 9 causes the pressure change, so as to promote the fluid to flow between the reaction chamber 59 and the pyrolysis bin 65, or between the reaction chamber 59 and the primary washing bin 68, or between the reaction chamber 59 and the secondary washing bin 69, or between the reaction chamber 59 and the PCR reagent bin 70, or between the reaction chamber 59 and the paraffin oil bin 71, or between the reaction chamber 59 and the PCR tube channel 61. Specifically, in one embodiment, the piston 9 is movably placed inside the reaction chamber 59, when the piston 9 moves upwards along the reaction chamber 59, the volume of the reaction chamber 59 expands, the pressure decreases, and the fluid is sucked into the reaction chamber 59 from the nucleic acid extraction element or the nucleic acid amplification element; and when the fluid in the reaction chamber 59 needs to be discharged, the piston 9 moves downwards along the reaction chamber 59, the volume of the reaction chamber 59 is reduced, the pressure increases, and the fluid is pressed into the nucleic acid extraction element or nucleic acid amplification element from the reaction chamber 59.

Preferably, the reaction chamber 59 is provided with a hollow accommodating chamber 74 configured to accommodate the magnetic rod 22, the piston 9 is the hollow cylinder, and the hollow cylinder in the piston 9 has the diameter matching that of the hollow accommodating chamber 74, so that the piston 9 can be sleeved outside the hollow accommodating chamber 74 and move vertically along an outer wall of the hollow accommodating chamber 74. Therefore, the reaction chamber 59 is located on the periphery of the hollow accommodating chamber 74.

Preferably, the upper cover 57 is attached with a waterproof and gas-permeable membrane for gas exchange and biological pollution prevention; the bottom cover 58 is provided with a penetrating area 75 for accommodating the channel turntable 15; and one or more PCR tubes 60 and PCR tube channels 61 are provided. In this embodiment, three PCR tubes 60 and three PCR tube channels 61 are provided. The PCR tube 60 is integrally connected with the bottom cover 58, and the PCR tube 61 does not need to be disassembled and transferred to other devices for heating, but only needs to be provided with a matched heating base. In the housing 56, a vertical tube 76 connected to each PCR tube is provided to accommodate a lyophilized powder type PCR reagent.

Preferably, in this embodiment, the nucleic acid extraction element or the nucleic acid amplification element is further provided with a reservation bin 77 which can be in communication with the reaction chamber 59 respectively.

The nucleic acid extraction and amplification device of the disclosure does not need to be provided with a chamber for storing the waste liquid. After DNA to be tested is adsorbed by the magnetic beads, the magnetic beads are always attracted in the reaction chamber 59 under the attraction action of the magnetic rod 22 on the magnetic beads, and the waste liquid generated after pyrolysis and washing is pressed back to the pyrolysis bin 65 and the washing bin respectively under the action of the piston 9. Since the channel turntable 15 is only provided with one bottom channel 16, with the rotation of the channel turntable 15, the pyrolysis bin 65 and the washing bin are no longer in communication with the reaction chamber 59, so that the DNA to be tested is completely separated from the waste liquid.

For a nucleic acid amplification reaction, the reagent in each chamber is applied in the pre-qualified sequence, for example, the samples are added to the pyrolysis bin for pyrolysis, then the mixed liquid after pyrolysis enters the reaction chamber, and the liquid in the washing bin enters the reaction chamber for washing, then is mixed with the PCR reagent and is led into the PCR tube finally for nucleic acid amplification. Theses chambers cannot be in communication with one another, which may cause cross contamination. In addition, the micro-channel of the turntable is configured to achieve the repeated liquid communication between these chambers and the reaction chamber for processing of the different samples. Relying on the rotation of the turntable, it is hoped that the rotation of the turntable will not cause liquid leakage, and in addition, it is also necessary to avoid liquid mixing between the chambers, which will cause the final detection failure. Thus, the rotation of the turntable needs to be precisely controlled. Besides, the turntable achieves the repeated communication between the reaction chamber and other chambers by means of the micro-channel. In order to reduce the cost, the overall structure for the nucleic acid amplification is disposable and is always made of cheap plastic materials by means of injection molding, and the rotation of the turntable needs to be precisely controlled, so that the samples can be processed in sequence; however, the turntable is provided with the micro-channel, for example, the micro-channel having the diameter of 100-600 microns, and besides, the various micro-pores needs to be accurately aligned to complete liquid flow, which needs accurate communication and switching of various chambers of the turntable and the reaction chamber. Such rotation does not need to be too fast, but needs to be very accurate and stable. One solution is to use the precision motor for control, but the cost is very high, and about RMB 3000 is needed for such precision motor. Moreover, the installed precision motor occupies a large volume, making the equipment appear bulky. In addition, the increase in the weight of the entire equipment is bound to significantly increase the cost. In addition, the worm gear and worm anti-backlash mechanism is used in the disclosure, and the simple mechanical design is adopted, so that the rotation angle of the turntable can be accurately controlled, leakage and other problems cannot be caused, and the equipment may be smaller and lighter and is very applicable to home or bedside diagnosis, and even to roadside detection.

The worm gear and worm transmission mechanism 8 of the nucleic acid extraction and detection integrated machine provided in this embodiment can accurately control the rotation angle of the channel turntable 15 of the nucleic acid extraction and detection integrated machine each time, wherein the aperture of the micro-channel of the channel turntable 15 is 600 microns, and the rotation angle of the channel turntable 15 is 35-151 degrees each time.

As shown in FIGS. 18, 19, 20-1, 20-2 and 21, the nucleic acid extractor in this embodiment comprises the nucleic acid extraction and amplification device 1 and the channel turntable 15, wherein the channel turntable 15 precisely matches with a turntable base 78 connected to the worm gear shaft 13 (FIG. 4); the nucleic acid extraction and amplification device 1 is mainly composed of the housing 56 having the plurality of chambers, the chambers include the reaction chamber 59, the pyrolysis bin 65, the primary washing bin 68, the secondary washing bin 69, the PCR reagent bin 70, the paraffin oil bin 71, the PCR tube 60, the PCR tube channel 61 and the reservation bin 77, and the bottom of each chamber is respectively provided with the micro-pores 67 or 66, and the nine micro-pores 67 corresponding to the pyrolysis bin 62, the primary washing bin 68, the secondary washing bin 69, the PCR reagent bin 70, the paraffin oil bin 71, the reservation bin 77 and the three PCR tube channels 61 are respectively provided around the bottom of the reaction chamber 59; and the channel turntable 15 is provided with two turntable micro-pores 79 and one bottom channel 16 in communication with the two turntable micro-pores 79, and the bottom channel 16 is 3 mm deep from the surface of the channel turntable 15. The channel turntable 15 can be rotated to enable the reaction chamber 59 to be in communication with the pyrolysis bin 65, the primary washing bin 68, the secondary washing bin 69, the PCR reagent bin 70, the paraffin oil bin 71, the reservation bin 77 or the PCR tube channel 61 respectively by means of the bottom channel 16. In the initial position (FIG. 20-2), the reaction chamber 59 is in communication with the pyrolysis bin 65 by means of the bottom channel 16 of the channel turntable 15; after the pyrolysis is completed, the channel turntable 15 needs to rotate clockwise by 50 degrees to communicate the reaction chamber 59 with the primary washing bin 68; after the primary washing is completed, the channel turntable 15 needs to rotate clockwise by 50 degrees to communicate the reaction chamber 59 with the secondary washing bin 69; after the secondary washing is completed, the channel turntable 15 needs to rotate clockwise by 42 degrees to communicate the reaction chamber 59 with the PCR reagent bin 70; after the nucleic acid extraction is completed, the nucleic acids to be tested are transferred to the reaction chamber 59, and the channel turntable 15 needs to rotate clockwise by 128 degrees at this moment to communicate the reaction chamber 59 with the second PCR tube channel 61; after the nucleic acids to be tested are transferred to the PCR tube 60, the channel turntable 15 needs to rotate anticlockwise by 93 degrees to communicate the reaction chamber 59 with the paraffin oil bin 71; and after the paraffin oil is transferred to the reaction chamber 59, the channel turntable 15 needs to rotate clockwise by 128 degrees to communicate the reaction chamber 59 with the second PCR tube channel 61 again to transfer the paraffin oil to the PCR tube 60 for heat-sealing, and then the PCR amplification reaction is performed. In addition, the reaction chamber 59 can also be in communication with the reservation bin 77 for adding other reagents for reaction. Besides, the upper surface of the channel turntable 15 is made of silica gel materials, which can help to play a certain sealing role.

In this embodiment, the micro-pores 66 of the various chambers of the consumable 1, as well as the micro-pores 79 and the bottom channel 16 of the channel turntable 15, all have the apertures of 600 microns. It can be understood that the smaller the aperture, the higher the precision of the rotation angle of the channel turntable 15 that needs to be controlled, and a slight error may lead to sample leakage and other problems; and in addition, the stability needs to be provided by the worm gear shaft 13 for the precise matching of the channel turntable 15 with the turntable base 78, so that the turntable base 78 is more stable, and the precise rotation of the channel turntable 15 is guaranteed. The expensive precision motor (with the cost being about 3000 yuan) used in the early stage of study is replaced by the worm gear and worm transmission mechanism 8 which is provided in this embodiment and is simple in structure, low in cost (about 500 yuan), small and convenient to install, debug and maintain, so that the accurate communication of the micro-pores having the aperture of 600 microns and the micro-channel under the load-speed and low-load conditions of the nucleic acid extraction and detection integrated machine is successfully achieved, the stability can be kept after the communication, and the problem of sample leakage can be avoided.

Figure 23:
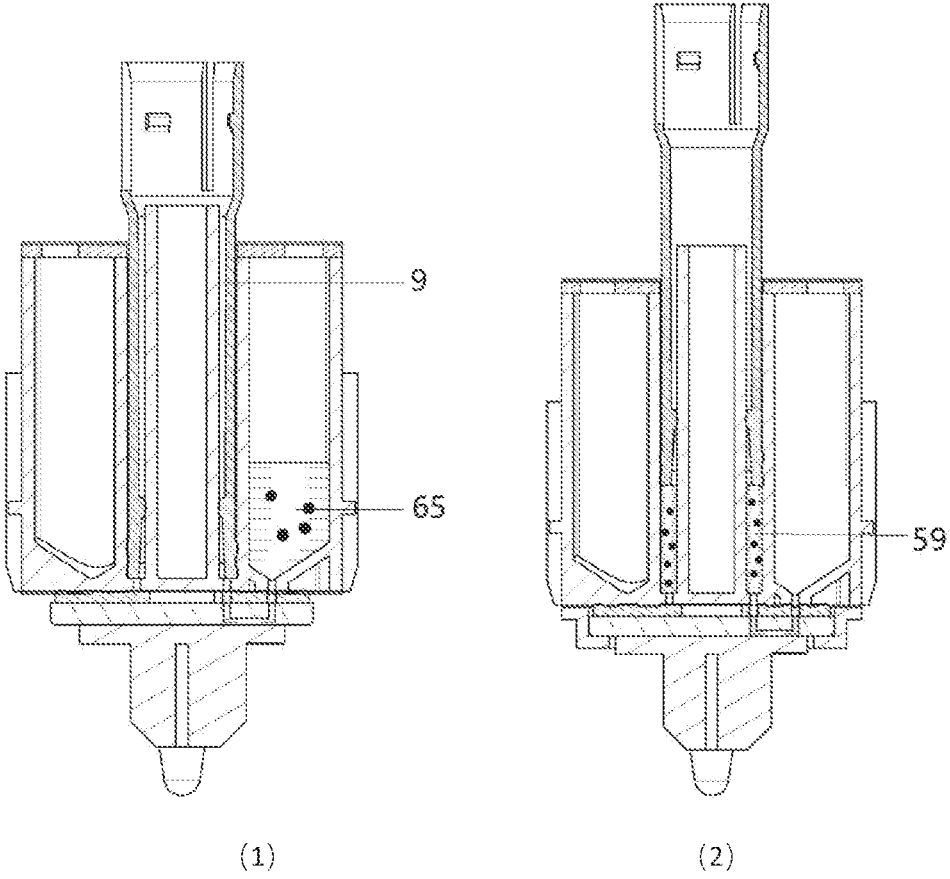
FIG. 23 is a schematic diagram of the different states of a pyrolysis bin in Embodiment 2; (1) is a schematic diagram of an initial state when a pyrolysis bin of a consumable in Embodiment 2 contains mixed samples, pyrolysis liquid and magnetic beads; (2) is a schematic diagram of a piston of the consumable in Embodiment 2 moving upwards to pump the mixed liquid into a reaction chamber.
Figure 24:
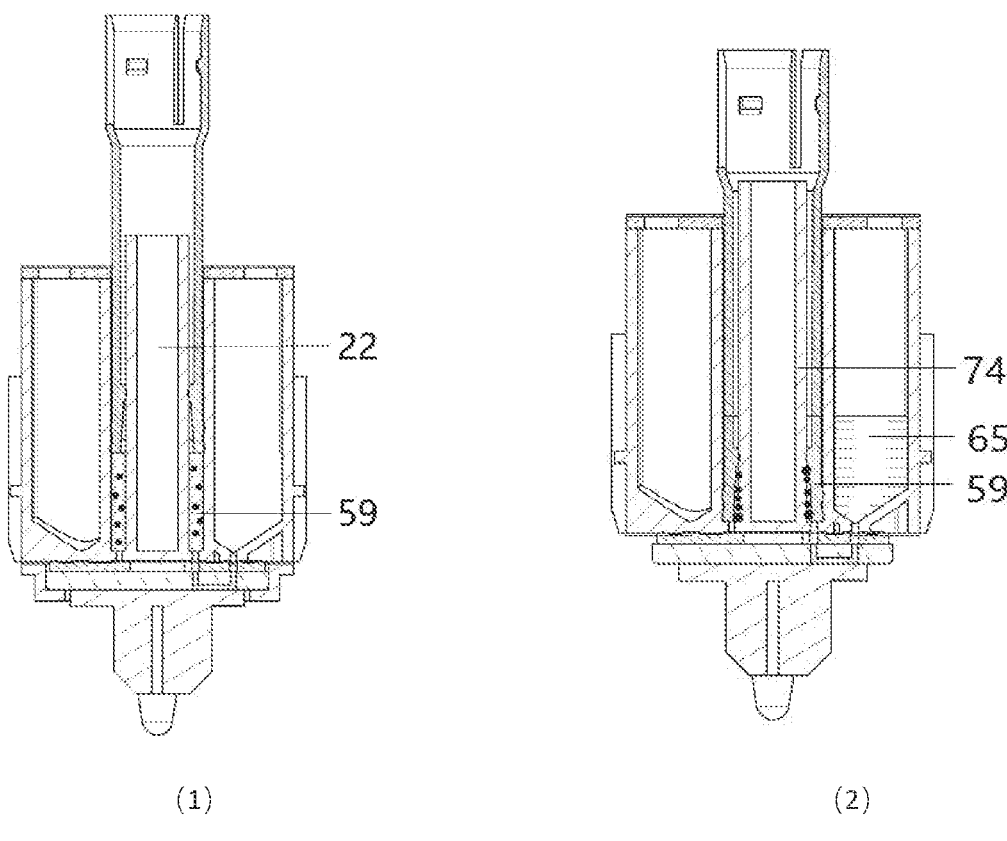
FIG. 24 is a schematic diagram of the different states of a pyrolysis bin in Embodiment 2; (1) is a schematic diagram of a magnetic rod in Embodiment 2 moving downwards such that nucleic acids are adsorbed by the magnetic beads and the magnetic beads are attracted to an outer wall of a hollow accommodating chamber; (2) is a schematic diagram of a piston of the consumable in Embodiment 2 moving upwards to pump the mixed liquid into a reaction chamber.
Figure 25:
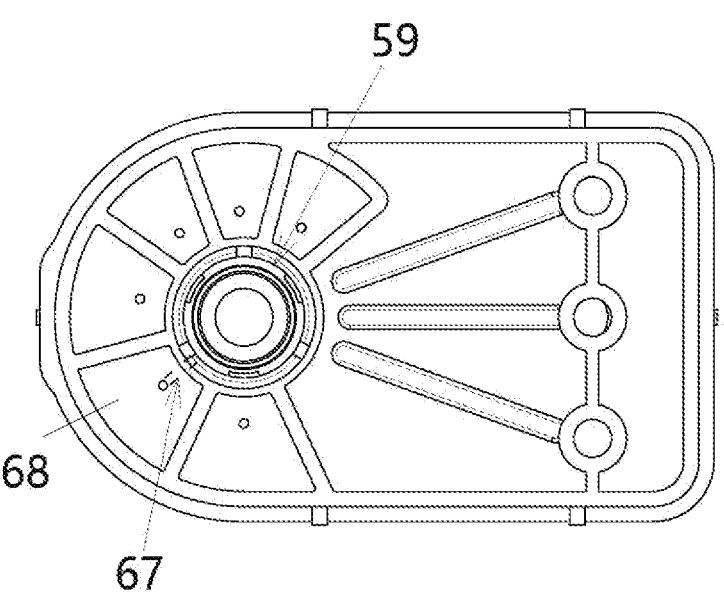
FIG. 25 is a schematic diagram of a channel turntable in Embodiment 2 rotating by a certain angle to communicate a bottom channel with a primary washing bin and the reaction chamber.

Embodiment 2. Process of Nucleic Acid Extraction and Amplification Performed by Nucleic Acid Extraction and Detection Integrated Machine In this embodiment, the nucleic acid extraction and amplification device-consumable 1 provided in Embodiment 1 is used to perform the nucleic acid extraction and amplification, and the process comprises the following steps:

1. adding collected samples to the pyrolysis bin 65, and at this moment, the pyrolysis bin 65 containing a mixed liquid: a pyrolysis liquid+the samples+the magnetic beads, as shown in FIG. 23(1);
2. the piston 9 moving upwards to pump the mixed liquid into the reaction chamber 59, as shown in FIG. 23(2);
3. the piston 9 moving downwards to press the mixed liquid back to the pyrolysis bin 65, so as to achieve first hammering of the liquid;
4. hammering the liquid repeatedly for the specified number of times;
5. the magnetic rod 22 moving downwards, as shown in FIG. 24(1), nucleic acids in the mixed liquid being adsorbed by the magnetic beads, and the magnetic beads being attracted on the outer wall of the hollow accommodating chamber 74 in the reaction chamber 59 under the action of the magnetic force of the magnetic rod 22;
6. the piston 9 moving downwards to press the mixed liquid back to the pyrolysis bin 65, and as shown in FIG. 24(2), and the magnetic beads being still attracted inside the reaction chamber 59 at this moment;
7. the channel turntable 15 rotating by a certain angle (rotating clockwise and horizontally by 50 degrees in this embodiment) to communicate the bottom channel 16 with the primary washing bin 68 and the reaction chamber 59, as shown in FIG. 25;
8. repeating actions in 2-6, and performing first washing on the magnetic beads and the nucleic acids;
9. the channel turntable 15 rotating by a certain angle (rotating clockwise and horizontally by 50 degrees in this embodiment) to communicate the bottom channel 16 with the secondary washing bin 69 and the reaction chamber 59;
10. repeating actions in 2-6, and performing second washing on the magnetic beads and the nucleic acids;
11. the channel turntable 15 rotating by a certain angle (rotating clockwise and horizontally by 42 degrees in this embodiment) to communicate the bottom channel 16 with the PCR reagent bin 70 and the reaction chamber 59;
12. repeating actions in 2-6, and performing elution on the magnetic beads and the nucleic acids;
13. the channel turntable 15 rotating by a certain angle (rotating clockwise and horizontally by 128 degrees in this embodiment) to communicate the bottom channel 16 with the PCR tube channel 61 and the reaction chamber 59, as shown in FIG. 22;
14. the piston 9 moving downwards to extrude a mixed solution of a PCR liquid and the nucleic acids into the PCR tube 60;
15. the channel turntable 15 rotating by a certain angle (rotating anticlockwise and horizontally by 93 degrees in this embodiment) to communicate the bottom channel 16 with the paraffin oil bin 71 and the reaction chamber 59;
16. the piston 9 moving upwards to extract a certain volume of paraffin oil;
17. the channel turntable 15 rotating by a certain angle (rotating clockwise and horizontally by 93 degrees in this embodiment) to communicate the bottom channel 16 with the PCR tube channel 61 and the reaction chamber 59;
18. the piston 9 moving downwards to extrude the paraffin oil into the PCR tube 60; and 19. later, heating the PCR tube 60 by means of a temperature control module in the driving component 2, and collecting fluorescence for analysis after nucleic acid amplification.

Figure 26:
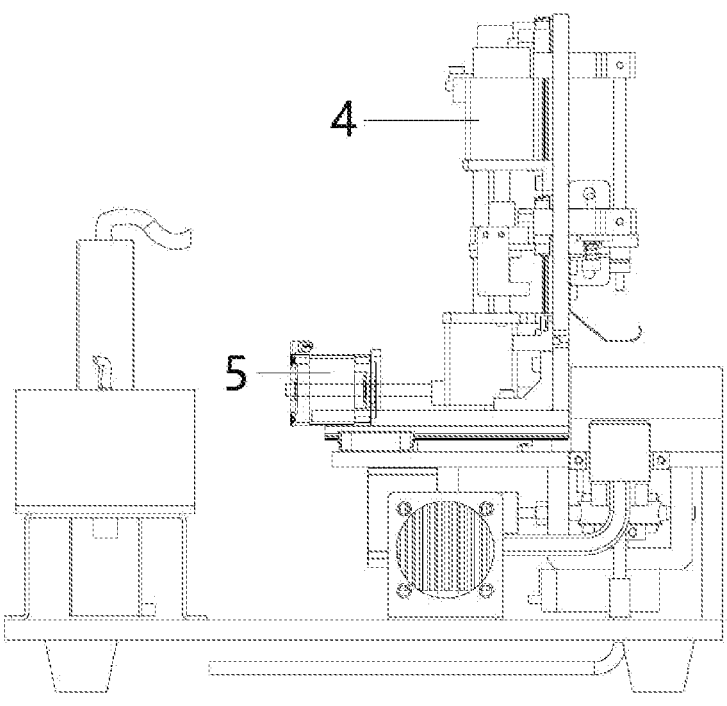
FIG. 26A is a schematic diagram of a nucleic acid extraction and detection integrated machine in Embodiment 3 in an initial state.
FIG. 26B is a schematic diagram of a horizontal movement component in Embodiment 3 driving a vertical movement component to move backwards together.
Figure 26:
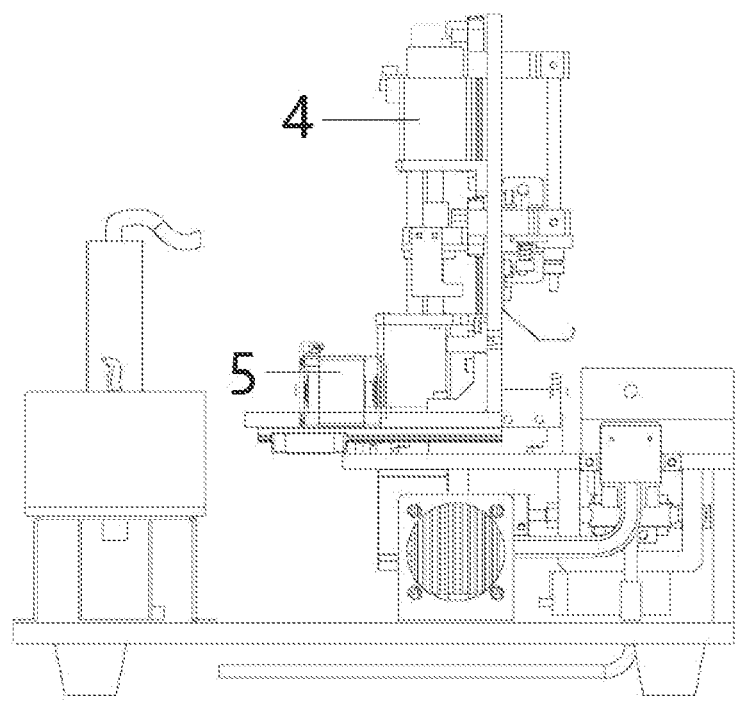
Figure 27:
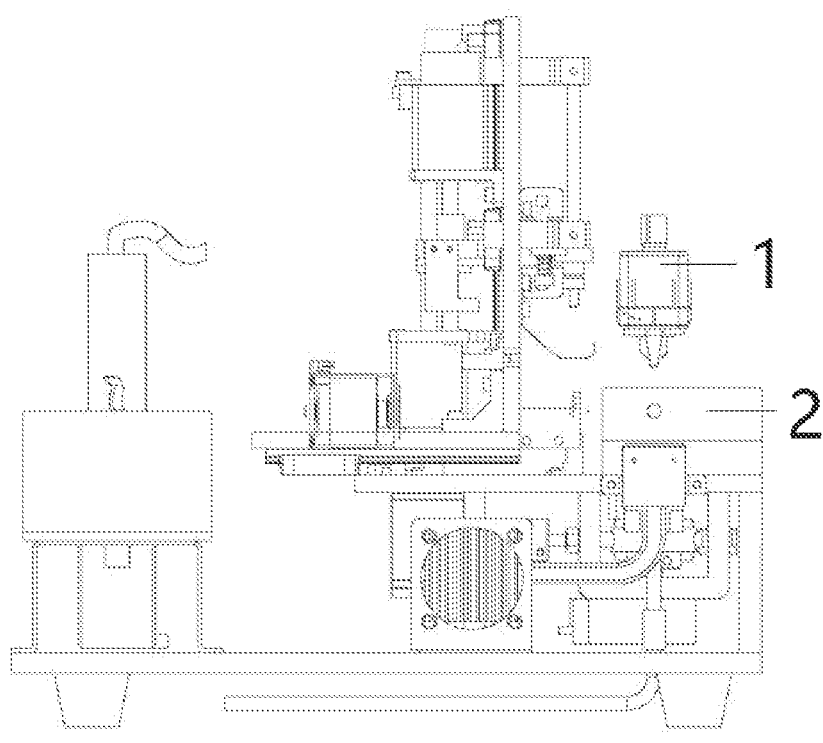
FIG. 27A is a schematic diagram of installing a consumable in Embodiment 3 into a driving component.
FIG. 27B is a schematic diagram of a piston rod in Embodiment 3 moving downwards to be combined with a piston.
Figure 27:
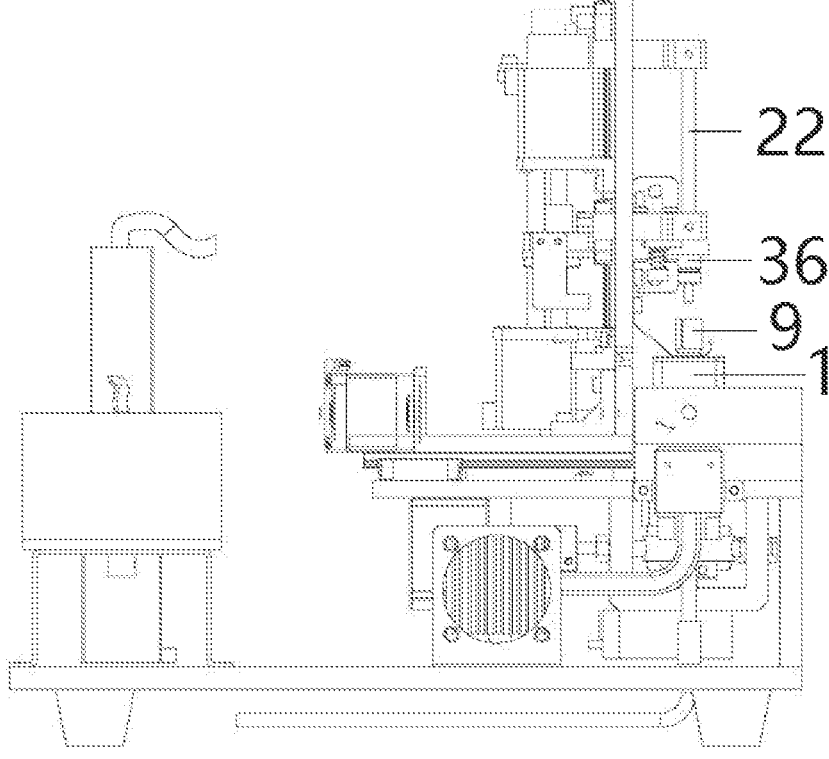

Embodiment 3. Working Process of Nucleic Acid Extraction and Detection Integrated Machine In this embodiment, the nucleic acid extraction and detection integrated machine provided in Embodiment 1 is used to perform the nucleic acid extraction, amplification and detection, and the process comprises the following steps:

(1) the nucleic acid extraction and detection integrated machine being in an initial state, as shown in FIG. 26A;

(2) the horizontal movement component 5 driving the vertical movement component 4 to move backwards together, as shown in FIG. 26B;

(3) installing the consumable 1 into the driving component 2, as shown in FIG. 27A;

(4) the piston rod 36 moving downwards to be combined with the piston 9 in the consumable 1, as shown in FIG. 27B;

(5) the piston 9 in the consumable 1 reciprocating vertically to perform the nucleic acid extraction and amplification, and the specific process being carried out according to the steps provided in Embodiment 2;

(6) collecting fluorescence by means of the light path component 3 and performing analysis to obtain a result; and (7) the piston rod 36 moving upwards, the piston 9 moving upwards being blocked by the electromagnet 41 and the jacking plate 40, the piston rod 36 and the piston 9 being separated, the consumable 1 being taken out by a vertical component, and thus the work being completed.

Embodiment 4. Effects of Reset Springs Having Different Working Elasticity on Rotation Angle of Channel Turntable of Nucleic Acid Extraction and Detection Integrated Machine The worm gear and worm transmission mechanism for the nucleic acid extraction and detection integrated machine provided in Embodiment 1 is used in this embodiment, and the reset springs having different elastic moduli are used respectively to perform 1000 times of repeated rotation experiments on the channel turntable of the nucleic acid extraction and detection integrated machine, so as to investigate the effects of the elastic moduli of the reset springs in the worm gear and worm transmission mechanism provided by the disclosure on control of the rotation angle of the channel turntable. The detection results are shown in Table 1.

Table 1. Effects of Reset Springs Having Different Working Elasticity on Rotation Angle of Channel Turntable of Nucleic Acid Extraction and Detection Integrated Machine

| S/N | Working Elasticity (N) | 1000 Times of Rotation Experiments |
|---|---|---|
| 1 | 2 | Micro-channel not in communication for 62 times |
| 2 | 3 | Micro-channel not in communication for 1 time |
| 3 | 4 | All accurately controlled |
| 4 | 5 | Micro-channel not in communication for 1 time |

-continued

| S/N | Working Elasticity (N) | 1000 Times of Rotation Experiments |
|---|---|---|
| 5 | 6 | Micro-channel not in communication for 45 times |
| 6 | 7 | Micro-channel not in communication for 78 times |

It can be seen from Table 1 that the worm gear and worm transmission mechanism for the nucleic acid extraction and detection integrated machine provided by the disclosure can basically accurately control the rotation angle of the channel turntable of the nucleic acid extractor, the control effect is good when the elastic force is 3-5N, and especially when the elastic force is 4N, the rotation angle of the channel turntable of the nucleic acid extraction and detection integrated machine can be completely accurately controlled.

Figure 28:
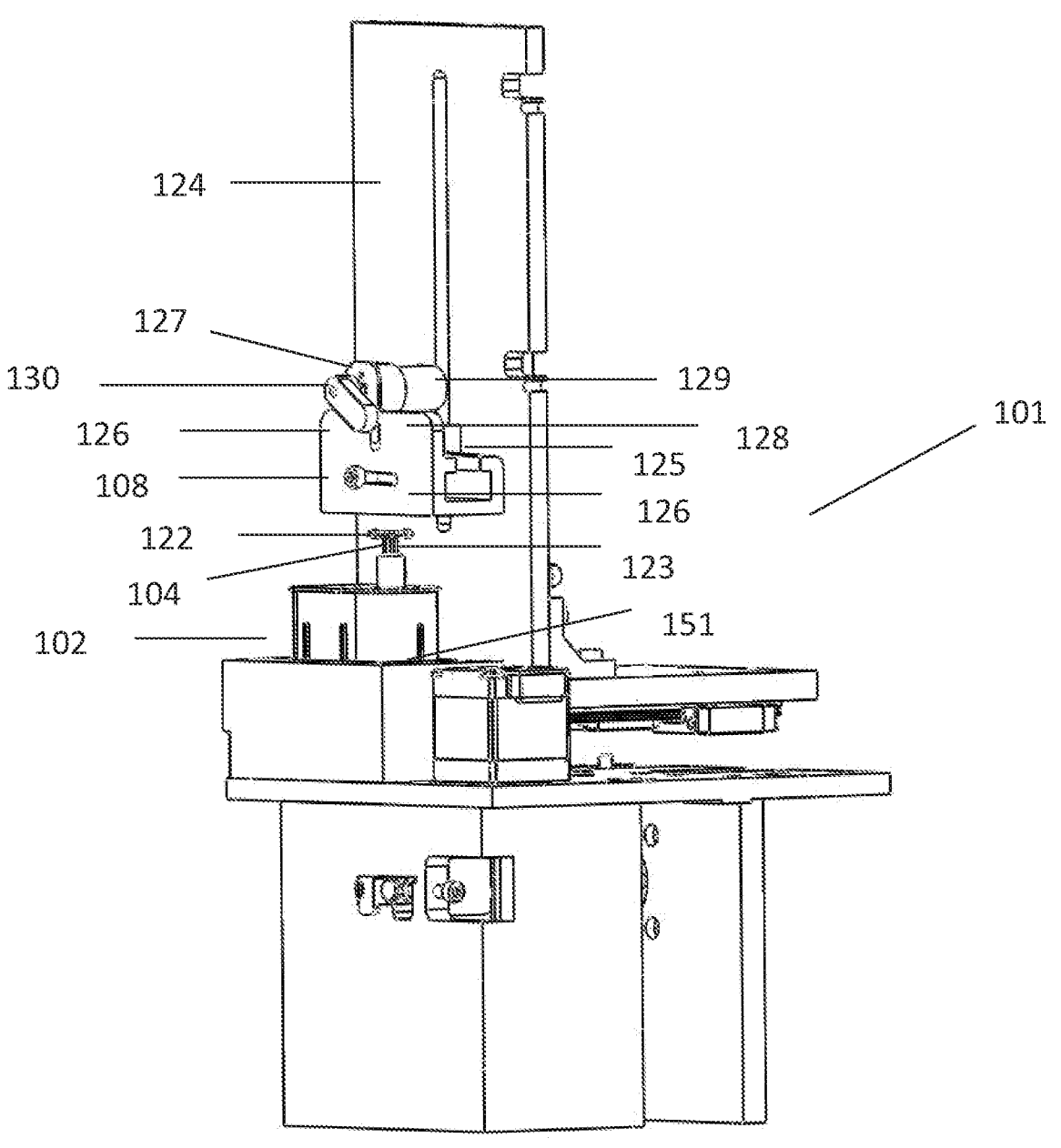
FIG. 28 is an overall structure diagram of a nucleic acid extraction and detection integrated machine in Embodiment 5.
Figure 29:
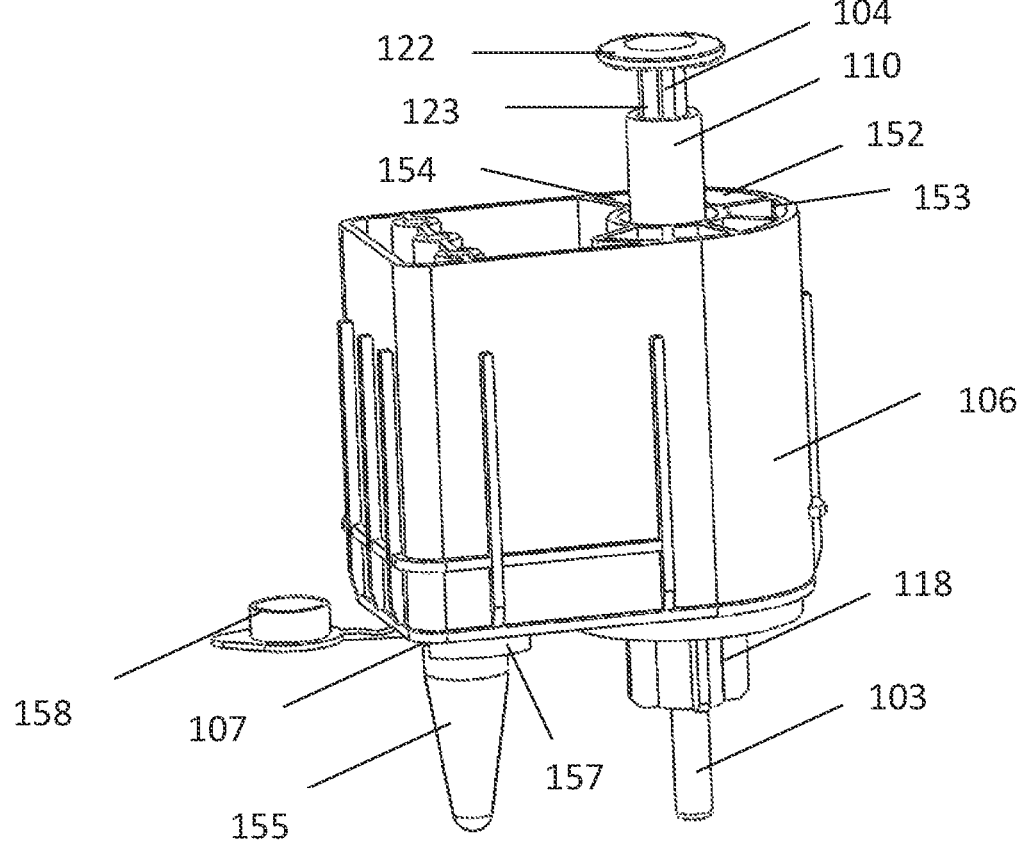
FIG. 29 is a structure diagram of a consumable in Embodiment 5.
Figure 30:
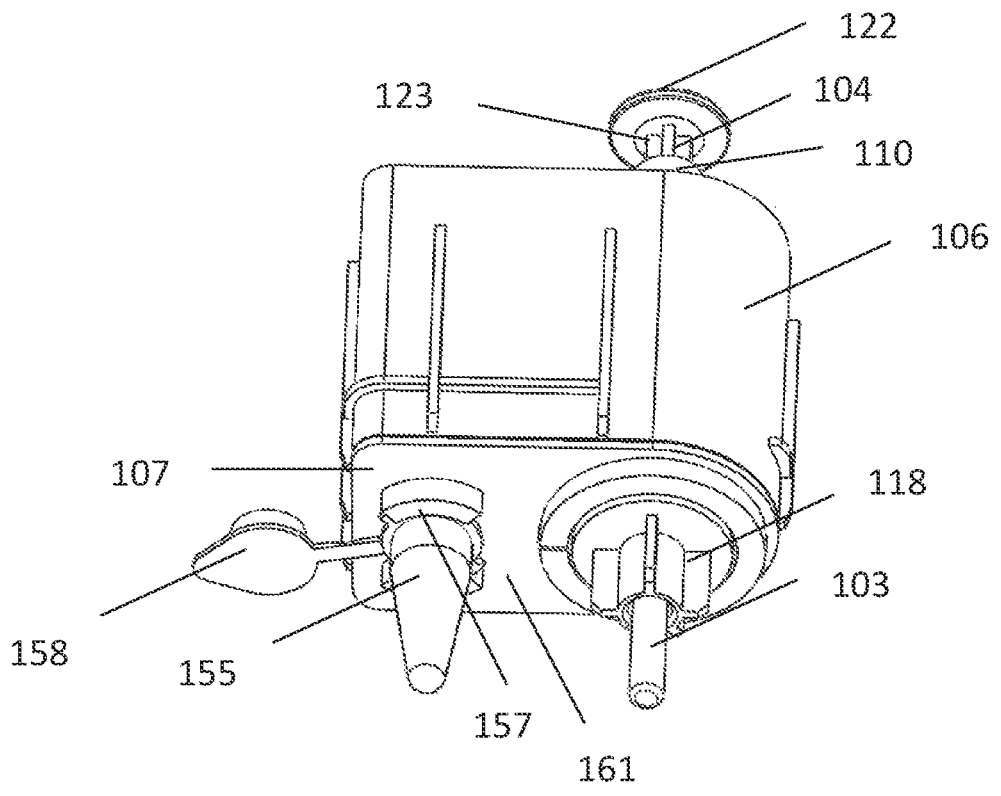
FIG. 30 is a structure diagram of the consumable in Embodiment 5 viewed from bottom to top.
Figure 31:
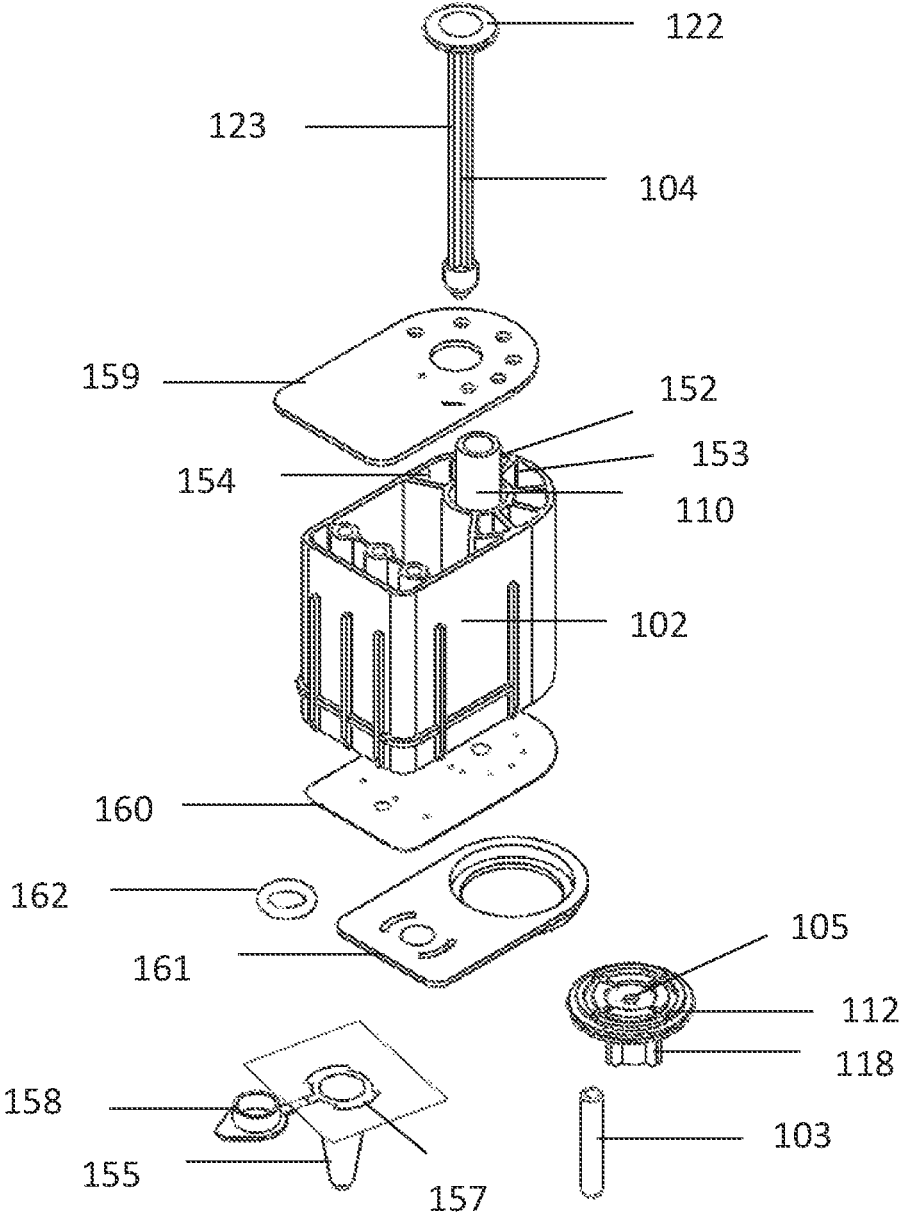
FIG. 31 is an exploded view of the consumable in Embodiment 5.
Figure 32:
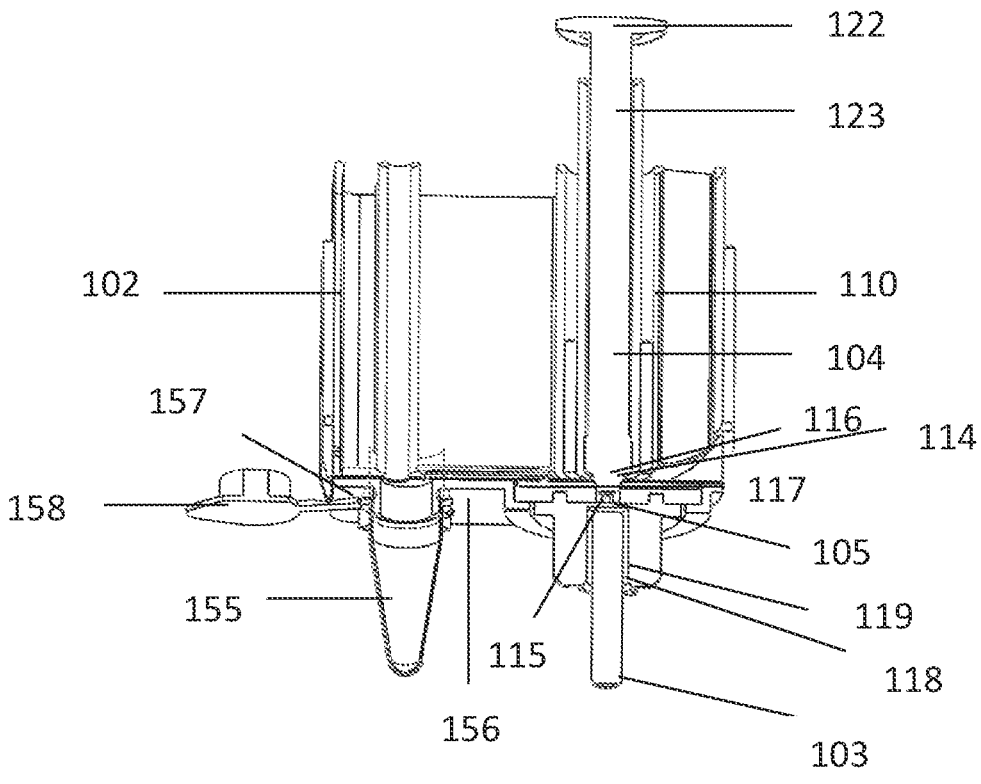
FIG. 32 is a sectional view of the consumable in Embodiment 5.
Figure 33:
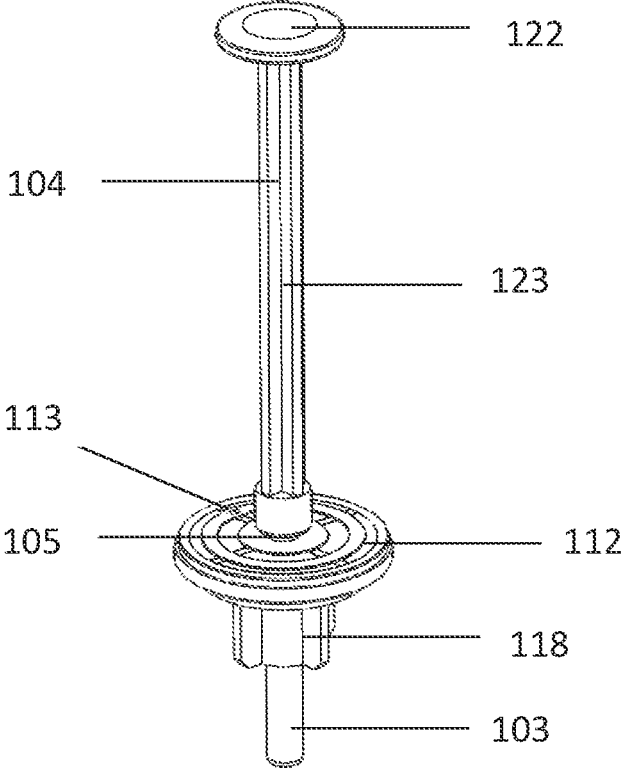
FIG. 33 is a schematic diagram of a piston, a channel turntable and a magnetic rod in the consumable in Embodiment 5.
Figure 34:
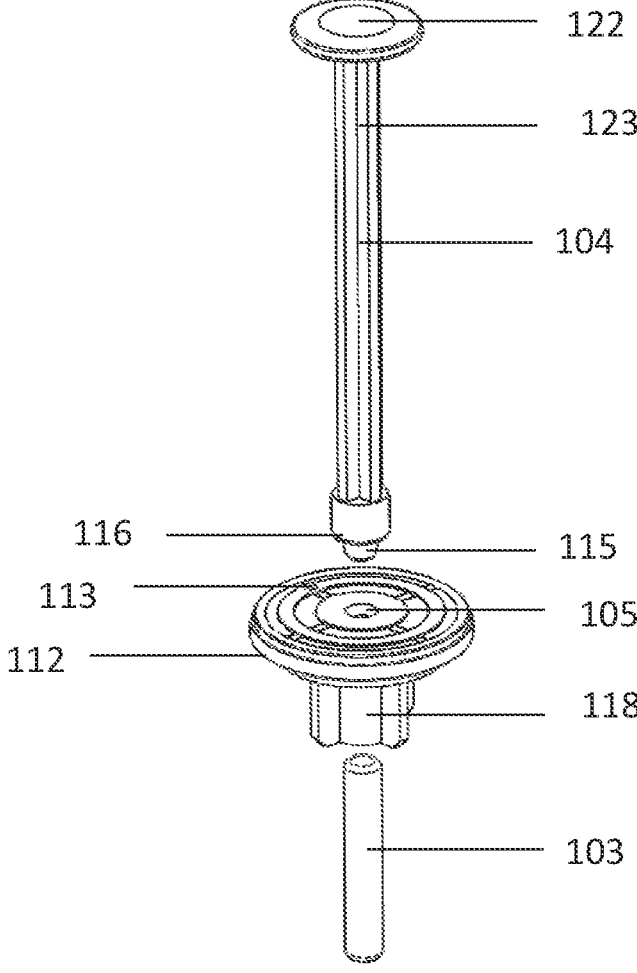
FIG. 34 is an exploded view of the piston, the channel turntable and the magnetic rod in the consumable in Embodiment 5.
Figure 35:
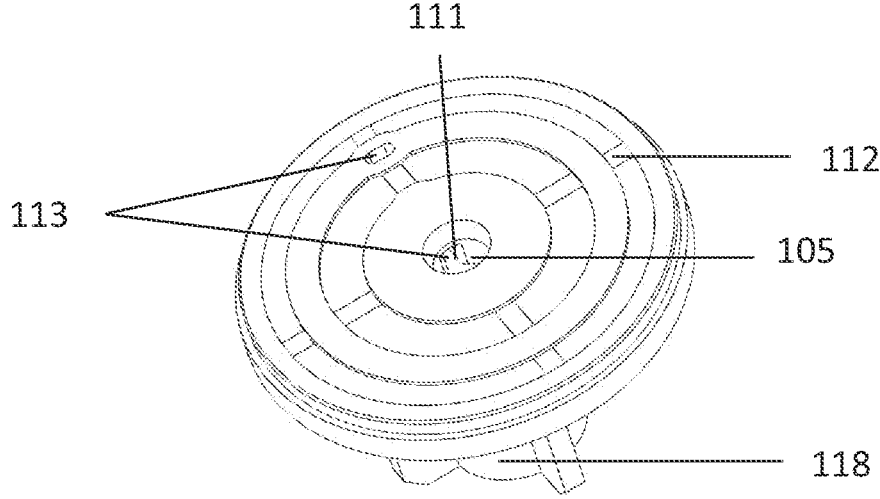
FIG. 35 is a structure diagram of the channel turntable in Embodiment 5.
Figure 36:
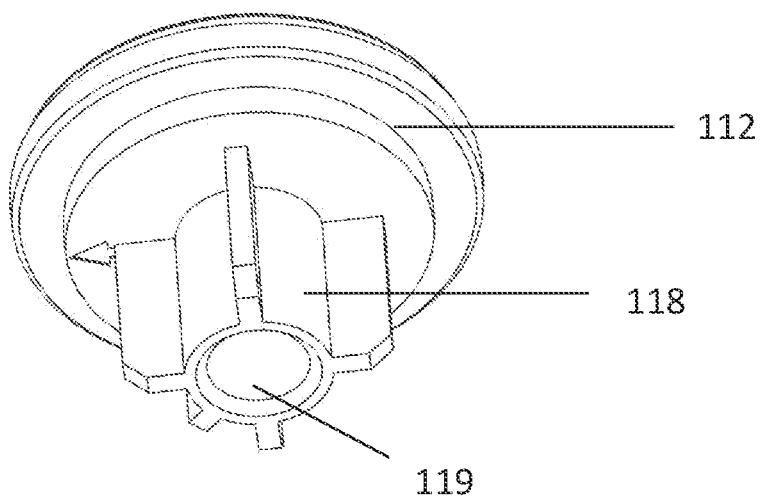
FIG. 36 is a structure diagram of the channel turntable in Embodiment 5 viewed from bottom to top.
Figure 37:
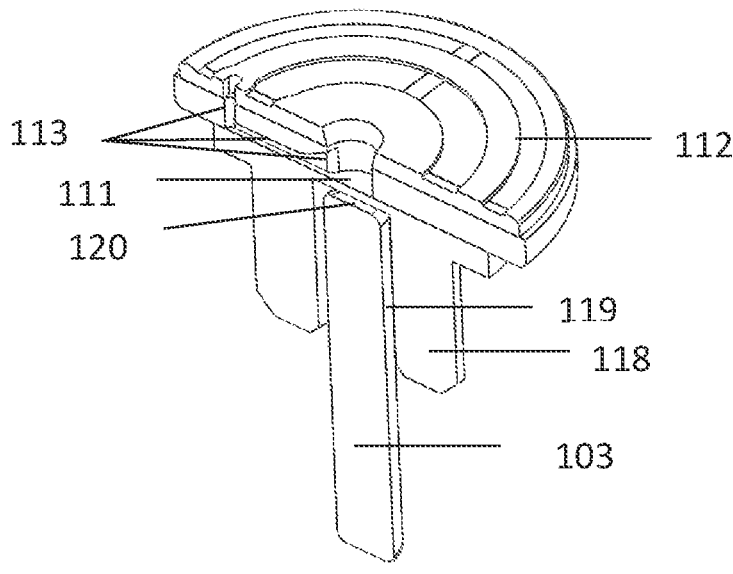
FIG. 37 is a sectional view of the channel turntable and the magnetic rod in Embodiment 5.
Figure 38:
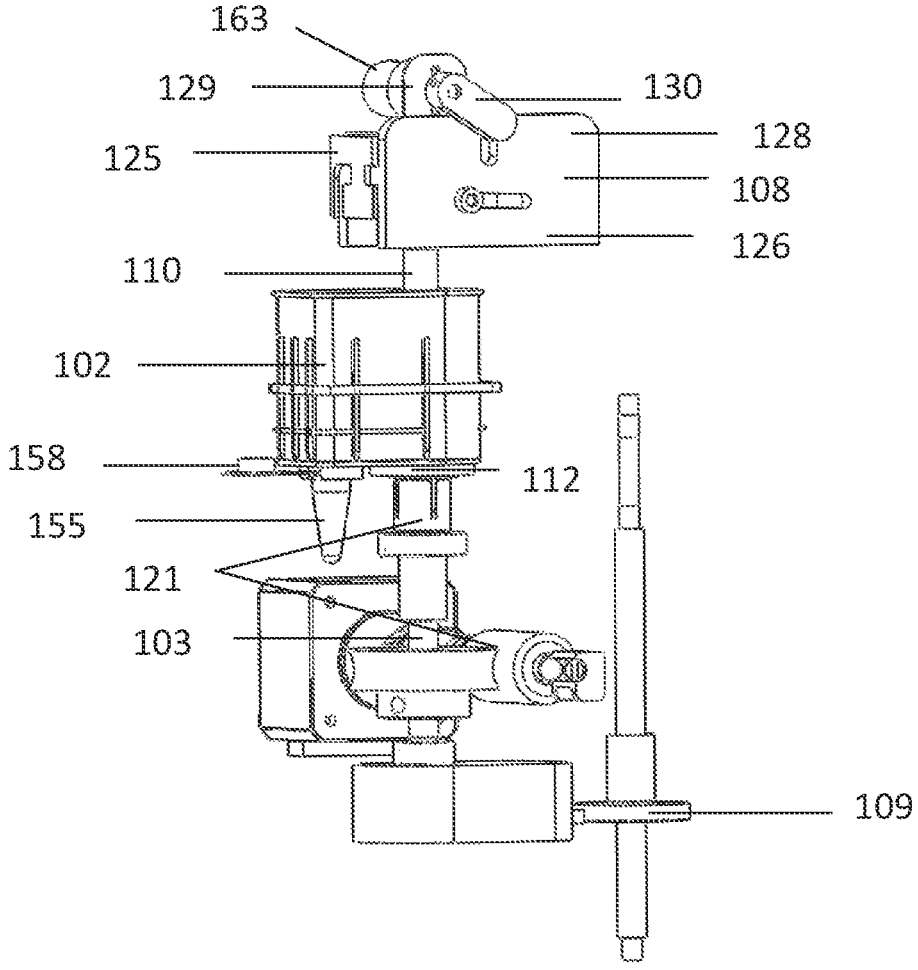
FIG. 38 is a structure diagram of a piston driving mechanism, the consumable, a worm gear and worm transmission mechanism and a magnetic rod driving mechanism of the nucleic acid extraction and detection integrated machine in Embodiment 5.
Figure 39:
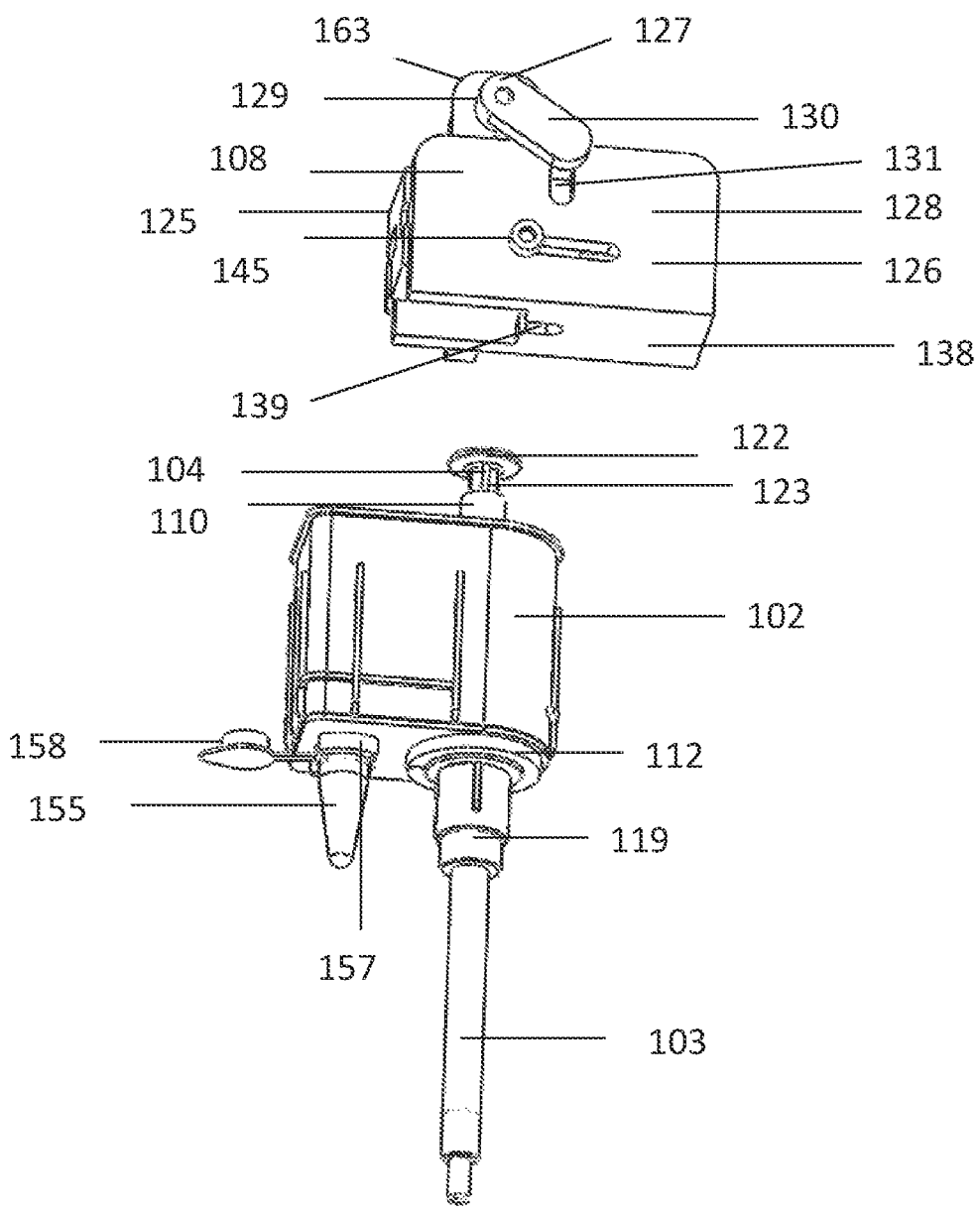
FIG. 39 is a structure diagram of the piston driving mechanism and the consumable in Embodiment 5.
Figure 40:
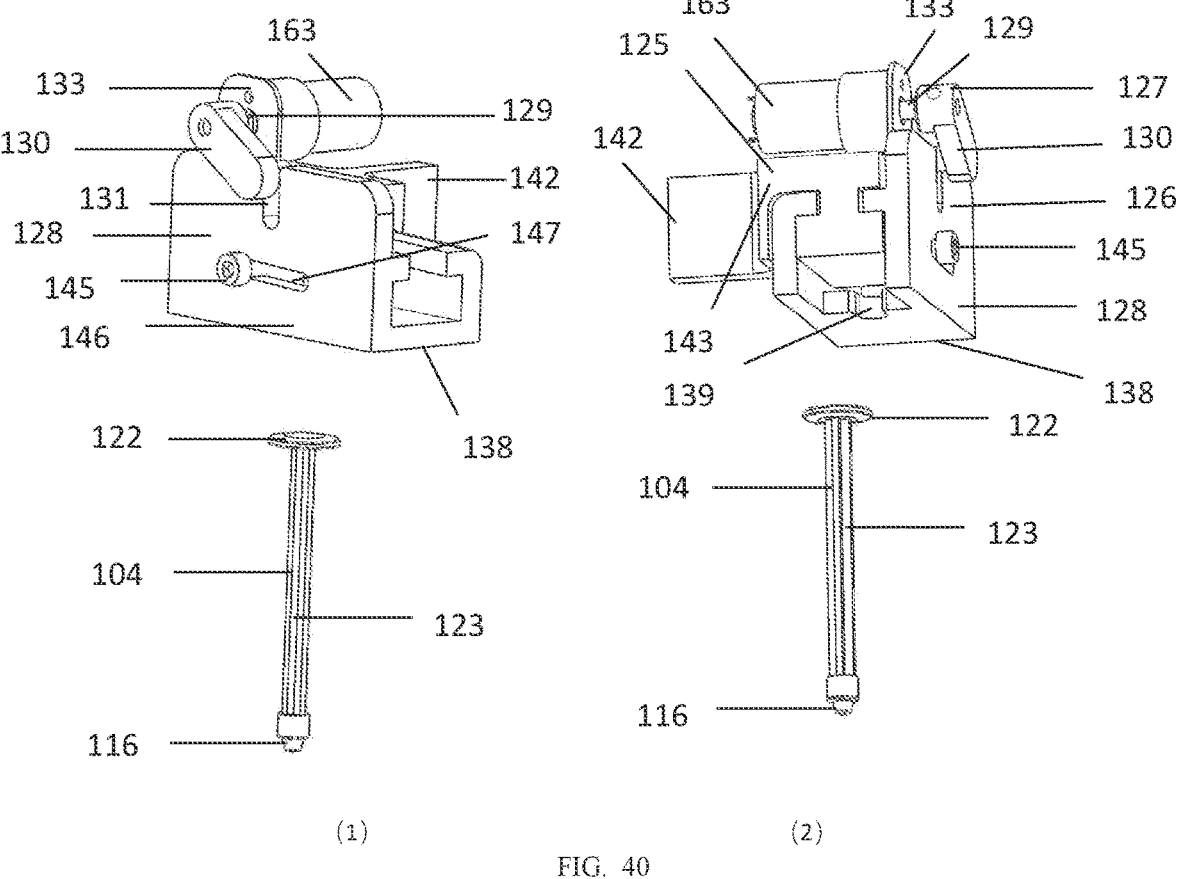
FIG. 40 is a structure diagram of the piston driving mechanism and the consumable in Embodiment 5, in which (1) and (2) are the structure diagrams at different viewing angles.
Figure 41:
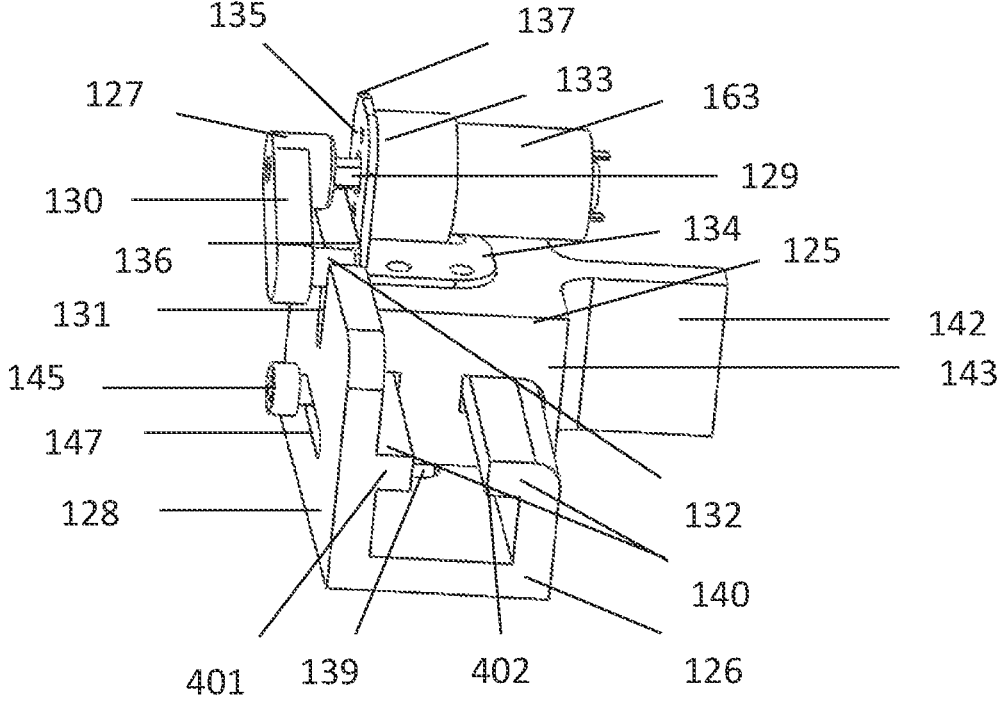
FIG. 41 is a structure diagram of the piston driving mechanism in Embodiment 5.
Figure 42:
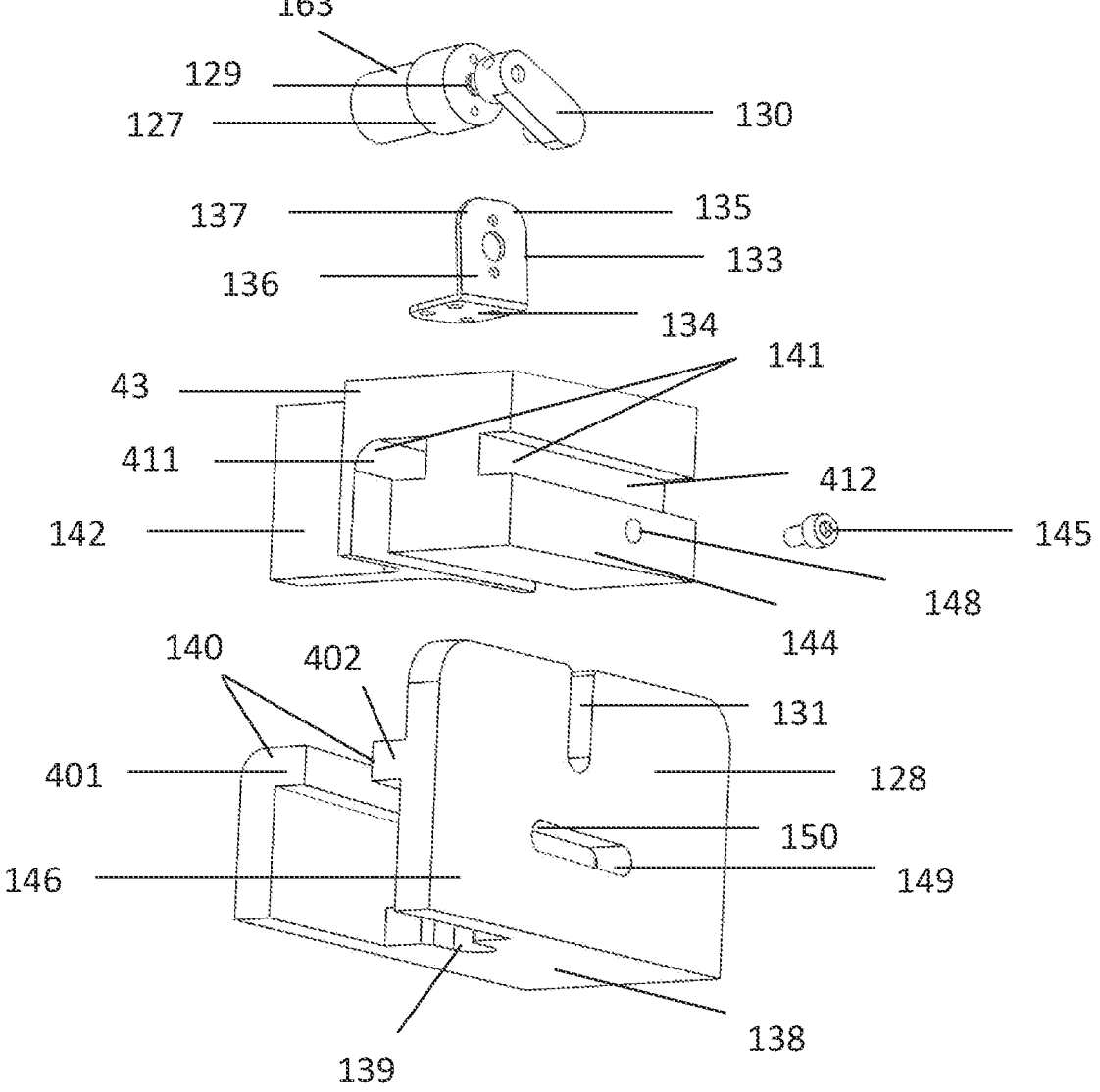
FIG. 42 is an exploded view of the piston driving mechanism in Embodiment 5.
Figure 43:
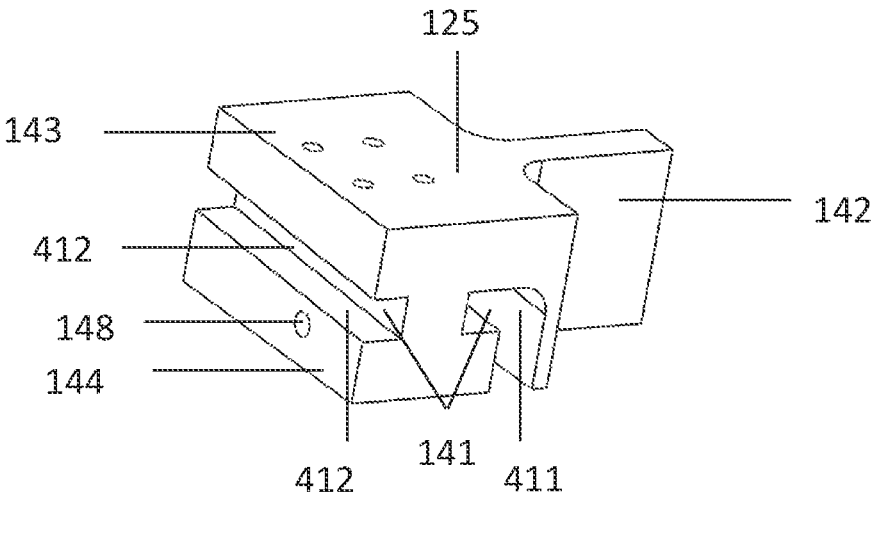
FIG. 43 is a structure diagram of a vertical movement module in Embodiment 5.
Figure 44:
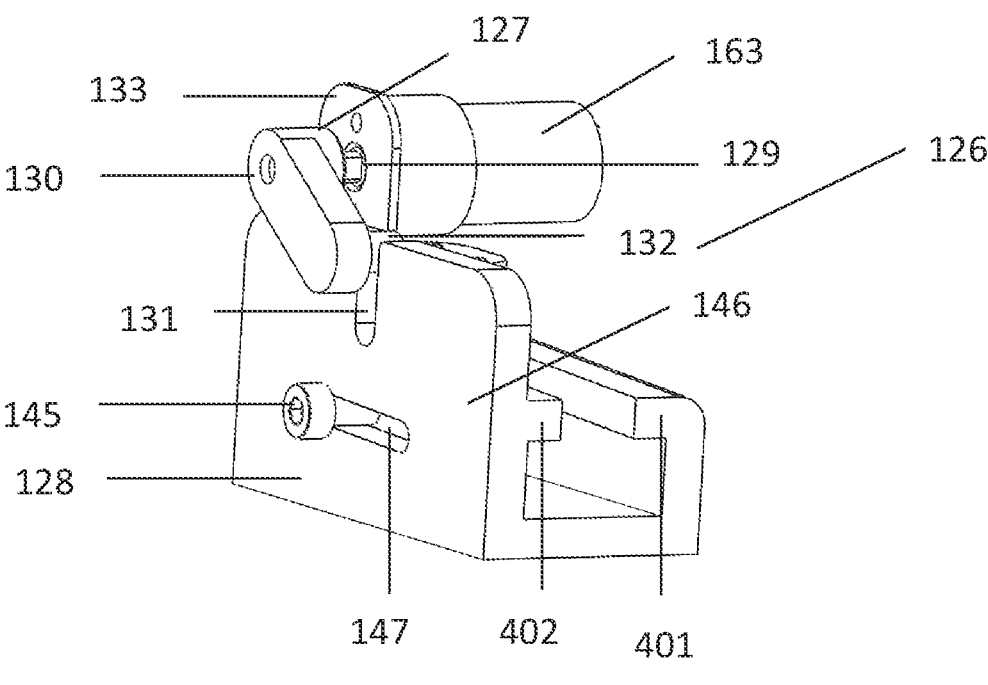
FIG. 44 is a structure diagram of a lateral movement module in Embodiment 5.
Figure 45:
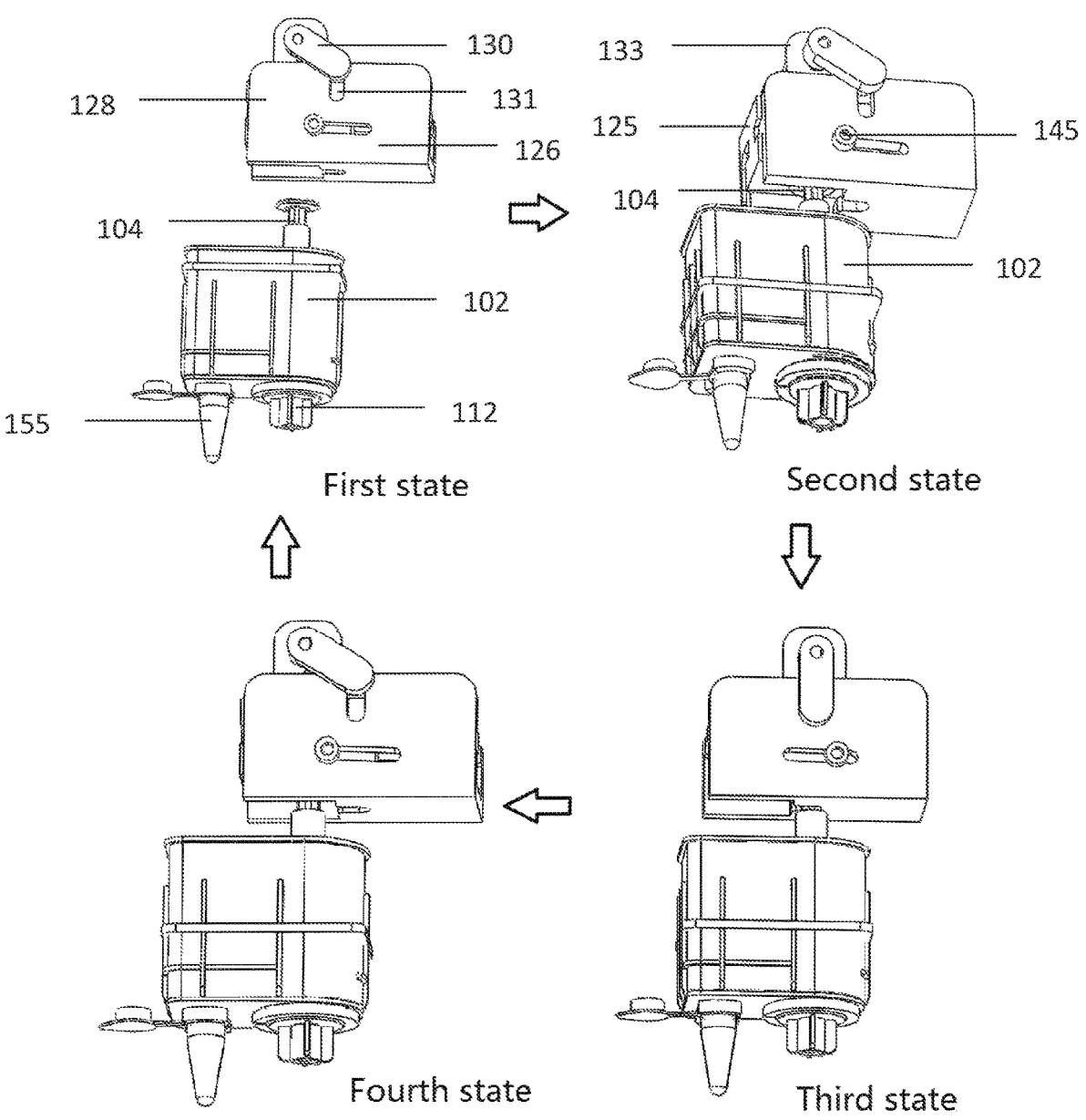
FIG. 45 is a change diagram of combined and separated states of the piston and the piston driving mechanism in Embodiment 5.

Embodiment 5. Another Consumable (Piston, Reaction Chamber and Magnetic Rod being Arranged in Sequence from Top to Bottom) and Matching Piston Driving Mechanism The nucleic acid extraction and amplification device provided in this embodiment is shown in FIGS. 28-45, wherein FIG. 28 is an overall structure diagram of a nucleic acid extraction and detection integrated machine; FIG. 29 is a structure diagram of the consumable; FIG. 30 is a structure diagram of the consumable viewed from bottom to top; FIG. 31 is an exploded view of the consumable; FIG. 32 is a sectional view of the consumable; FIG. 33 is a schematic diagram of a piston, a channel turntable and a magnetic rod in the consumable; FIG. 34 is an exploded view of the piston, the channel turntable and the magnetic rod in the consumable; FIG. 35 is a structure diagram of the channel turntable; FIG. 36 is a structure diagram of the channel turntable viewed from bottom to top; FIG. 37 is a sectional view of the channel turntable and the magnetic rod; FIG. 38 is a structure diagram of a piston driving mechanism, the consumable, the worm gear and worm transmission mechanism and a magnetic rod driving mechanism of the nucleic acid extraction and detection integrated machine; FIG. 39 is a structure diagram of the piston driving mechanism and the consumable; FIG. 40 is a structure diagram of the piston driving mechanism and the consumable, in which (1) and (2) are the structure diagrams at different viewing angles; FIG. 41 is a structure diagram of the piston driving mechanism; FIG. 42 is an exploded view of the piston driving mechanism; FIG. 43 is a structure diagram of a vertical movement module; FIG. 44 is a structure diagram of a lateral movement module; and FIG. 45 is a change diagram of combined and separated states of the piston and the piston driving mechanism.

It can be seen from FIG. 28 that the nucleic acid extraction and amplification device provided in this embodiment is another disposable consumable 102 (hereinafter referred to as the consumable 2) used in the nucleic acid extraction and detection integrated machine 101, is made of plastics and other materials, and is configured to help the nucleic acid extraction and detection integrated machine 101 to achieve extraction, purification and amplification of nucleic acids. The consumable 102 mainly comprises a nucleic acid extraction assembly 106 and a nucleic acid amplification assembly 107 (FIGS. 29-32), wherein the nucleic acid extraction assembly 106 is configured to extract the nucleic acids in the samples and comprises the piston 104, the reaction chamber 105 and a permanent magnet, the permanent magnet in this embodiment is the magnetic rod 103, and the piston 104, the reaction chamber 105 and the magnetic rod 103 are arranged in sequence from top to bottom. The nucleic acid amplification assembly 107 is configured to amplify the nucleic acids extracted by the nucleic acid extraction assembly 106.

As shown in FIG. 38, the nucleic acid extraction and detection integrated machine 101 is internally provided with the piston driving mechanism 108 and the magnetic rod driving mechanism 109, the piston driving mechanism 108 is configured to control the piston 104 in the consumable 102 to move vertically in a piston channel 110, and the magnetic rod driving mechanism 109 is configured to control the magnetic rod 103 to move vertically in a magnetic rod channel 119. Regarding the nucleic acid extraction and detection integrated machine 101, the piston driving mechanism 108 is mainly used to drive the piston 104 in the consumable 102 to perform vertical pumping and suction movements to generate the pumping and suction force to change the air pressure in each area of the consumable 102 and control the flow direction of a fluid in the consumable 102, and cooperates with the magnetic rod driving mechanism 109 to drive the magnetic rod 103 to move vertically to control positions of magnetic beads, so as to complete the adsorption of the nucleic acids, the washing of the magnetic beads, and the elution of the nucleic acids in the consumable 102 (mainly the reaction chamber 105). The magnetic rod 103, the magnetic rod driving mechanism 109 and the piston driving mechanism 108 are reusable and are not disposable consumables. Therefore, in order to improve the nucleic acid detection sensitivity and accuracy of the nucleic acid extraction and detection integrated machine 101, the nucleic acid extraction and purification in the consumable 102 must be fully and thoroughly completed.

In order to make the magnetic beads more concentrated in the reaction chamber 105, make the nucleic acid adsorption, washing and elution more sufficient, and ensure that the vertical movement of the piston 104 and the vertical movement of the magnetic rod 103 do not interfere with each other, in this embodiment, the structure of the consumable 102 is improved as shown in FIGS. 33 and 34, so that the reaction chamber 105, the piston 104 and the magnetic rod 103 can be arranged independently, the defects caused by nesting are avoided, meanwhile, the structure of the consumable 102 is still compact without affecting the external dimensions, the internal structure operates more smoothly, and the overall operation of the nucleic acid extraction and detection integrated machine 101 is not affected.

As shown in FIG. 35, the reaction chamber 105 is a cylindrical recess with an upward opening; and the piston 104 is located above the reaction chamber 105 (FIG. 34). The reaction chamber 105 is changed from the original narrow annular channel surrounding the periphery of the piston 104 into the cylindrical recess with the upward opening under the piston 104, that is, the reaction chamber 105 is still in communication with the piston 104, but the piston 104 cannot move downwards to the bottom of the reaction chamber 105 and can only reach the upper side of the reaction chamber 105. The reaction chamber 105 is separated from the piston 104 to form the complete reaction chamber 105 independently, the magnetic beads can be more evenly scattered in the samples in the reaction chamber 105 and can be quickly and completely converged when being attracted by the magnetic rod 103, thus the dead corners are eliminated, and the efficiency of the processes of nucleic acid adsorption, washing and elution is effectively improved.

Since the piston 104 cannot enter the reaction chamber 105, the problem that the piston 104 may stick and take away the samples or the magnetic beads due to the vertical movement of the piston can be avoided, which further ensures the precision of the nucleic acid extraction process. The piston 104 moves vertically in the piston channel 110, the piston channel 110 is in communication with the reaction chamber 105, and when the piston 104 performs the vertical pumping and suction in the piston channel 110, the piston can generate the pumping and suction force on the fluid in the reaction chamber 105, thereby changing the air pressure in each area of the consumable 102 (including the reaction chamber 105 and other chambers in the consumable 102).

The magnetic rod 103 is located under the reaction chamber 105, so that the piston 104, the reaction chamber 105 and the magnetic rod 103 are arranged vertically and independently in sequence from top to bottom; when the magnetic rod 103 moves upwards to get close to the reaction chamber 105, the magnetic attraction force is located at the bottom 111 of the reaction chamber, so that the magnetic beads can be gathered at the bottom 111 of the reaction chamber, are more concentrated and are easy to collect, and thus errors are reduced; when the magnetic rod 103 moves downwards to get away from the reaction chamber 105, the magnetic attraction force disappears, and the magnetic beads are scattered in the cylindrical reaction chamber 105, so that the magnetic beads can make contact with the samples more completely and sufficiently and can also be washed and eluted more sufficiently; therefore, there is no dead corner in the reaction chamber 105 for the magnetic beads, the adsorption, washing and elution of the nucleic acids by the magnetic beads can be more sufficient and thorough, the influence of the dead corners is eliminated, the efficiency of the nucleic acid extraction is improved, and the sensitivity of the nucleic acid detection is improved.

As shown in FIGS. 32-38, the nucleic acid extraction assembly 106 further comprises the channel turntable 112; the reaction chamber 105 is located on the channel turntable 112; and a micro-channel 113 in communication with the reaction chamber 105 is provided in the channel turntable 112. The reaction chamber 105 is the recess with the upward opening that is provided in the center of the channel turntable 112; the size of a lower end of the piston 104 and the size of a lower end 114 of the piston channel 110 are reduced; when the piston 104 moves downwards to the lowest position, the piston 104 is blocked by the piston channel 110 and cannot enter the reaction chamber 105; and a bottom surface 115 of the piston and the reaction chamber 105 in the center of the channel turntable 112 form a sealed chamber jointly. The reaction chamber 105 of the consumable 102 is essentially a groove formed in the center of the channel turntable 112, the groove may rotate along with the channel turntable 112, but is always located at the position of a rotating shaft in the center of the channel turntable 112, and the groove is always located under the piston 104. Since the relatively small reaction chamber 105 is required by the nucleic acid extraction, the reaction chamber 105 has the relatively small cross section diameter. The lower end of the piston 104, that is, a piston head 116 is in the shape of an inverted cone (funnel), and the cross section thereof is gradually reduced, and meanwhile, a lower end 117 of the piston channel 110 is also gradually reduced, so that when the piston 104 moves downwards to the lowest position, the piston head 116 is blocked by the piston channel 110 and cannot enter the reaction chamber 105.

As shown in FIG. 36, a lower portion of the channel turntable 112 is provided with a cross-shaped fixing element 118, a central rotating shaft of the fixing element 118 is a hollow cylinder, and the hollow cylinder is the magnetic rod channel 119 for the vertical displacement of the magnetic rod 103; and as shown in FIG. 10, a bottom surface 120 of the reaction chamber 105 is a top end of the magnetic rod channel 119. The channel turntable 112 can be fixed to the worm gear and worm transmission mechanism 121 of the nucleic acid extraction and detection integrated machine 101 by means of the fixing element 118, and the worm gear and worm transmission mechanism 121 drives the channel turntable 112 to rotate precisely, thereby ensuring that the micro-channel 113 in the channel turntable 112 is precisely connected to certain chambers when needed and disconnected accurately when needed according to working program settings. When the worm gear and worm transmission mechanism 121 rotates to drive the channel turntable 112 to rotate, although the rotating shaft in the center of the fixing element 118 also rotates, it will not move, while other positions will move annularly around the rotating shaft. In this embodiment, by skillfully using the characteristic that the rotating shaft rotates without displacement, the rotating shaft is changed into a hollow cylinder to serve as the magnetic rod channel 119, so that the magnetic rod 103 can move vertically in the hollow cylinder of the rotating shaft; and at this moment, it should be noted that although the magnetic rod channel 119 is rotating, the magnetic rod 103 does not rotate, and the magnetic rod 103 can only move vertically in the rotating magnetic rod channel 119.

The piston 104 needs to change the air pressure in each area in the consumable 102 by means of the pumping and suction force generated by the vertical pumping and suction movements, thereby controlling the flow directions of the fluids in the consumable 102; when the piston 104 moves downwards, the air pressure in the reaction chamber 105 is increased, and the fluid in the reaction chamber 105 is pressed into other chambers via the micro-channel 113; when the piston 104 moves upwards, the air pressure in the reaction chamber 105 is decreased, and the fluids in other chambers flow into the reaction chamber 105 via the micro-channel 113. The magnetic rod 103 needs to control the positions of the magnetic beads through the vertical movement; when the magnetic rod 103 moves upwards to get close to the bottom surface 120 of the reaction chamber 105, the magnetic rod generates the magnetic attraction force on the magnetic beads in the reaction chamber 105, so that the magnetic beads are gathered near the bottom surface 120 of the reaction chamber 105; and when the magnetic rod 103 moves downwards to get away from the bottom surface 120 of the reaction chamber 105, the magnetic attraction force on the magnetic beads in the reaction chamber 105 is reduced, so that the magnetic beads are scattered in the reaction chamber 105. Therefore, the nucleic acid extraction and detection integrated machine 101 must be provided with the piston driving mechanism 108 and the magnetic rod driving mechanism 109 so as to control the vertical movements of the piston 104 and the magnetic rod 103 respectively. The magnetic rod 103 is fixed in the nucleic acid extraction and detection integrated machine 101, the lower end of the magnetic rod 103 is also fixedly provided with the magnetic rod driving mechanism 109, and the magnetic rod driving mechanism 109 is driven by a motor to move vertically so as to drive the magnetic rod 103 to move vertically. In addition, the piston 104 is a part of the consumable 102 and needs to be replaced frequently, thus the design of the piston driving mechanism 108 is more complex, and the piston driving mechanism needs to be automatically combined with the piston 104 before driving the piston 104 to move vertically and also needs to be automatically separated from the piston 104 after the piston 104 moves vertically.

In the nucleic acid extraction and detection integrated machine 101 provided by this embodiment, the piston 104 is no longer a hollow cylinder, and the magnetic rod 103 has also been moved out of the piston 104 and placed below the piston 104 and the reaction chamber 105, which also brings great benefits to the design of the piston driving mechanism 108. The piston 104 in the consumable 102 does not need to be in the hollow cylinder shape any more, but can be a solid piston 104 directly, a piston cover 122 is provided at the top of the piston 104, and a piston rod 123 is arranged below the piston cover 122. The piston driving mechanism 108 is redesigned for the solid piston 104 provided with the piston cover 122, so that it can drive the piston 104 more easily and smoothly to complete the pumping and suction movements to complete the extraction and purification of the nucleic acids. The piston driving mechanism 108 is installed on a panel 124 of the nucleic acid extraction and detection integrated machine 101, and when the consumable 2 is put into the nucleic acid extraction and detection integrated machine 101, the piston driving mechanism 108 is located above the consumable 102.

As shown in FIGS. 39-41, the piston driving mechanism 108 comprises the vertical movement module 125 and the lateral movement module 126, wherein the vertical movement module 125 is configured to drive the piston 104 to move vertically, so as to control the pumping and suction movement of the piston 104 in the consumable 102; the lateral movement module 126 can move left and right relative to the vertical movement module 125 and is configured to realize the combination or separation of the piston 104 and the piston driving mechanism 108; and the vertical movement module 125 and the lateral movement module 126 are integrally nested and combined.

In the working process of the nucleic acid extraction and detection integrated machine 101, the consumable 102 is required to be placed into a recess 151 of the nucleic acid extraction and detection integrated machine 101 firstly, at this moment, the piston 104 and the piston driving mechanism 108 are separated, then the piston driving mechanism 108 is started to enable the lateral movement module 126 of the piston driving mechanism 108 to move to the left or right, and when the lateral movement module moves to the proper position, the piston driving mechanism 108 is combined with the piston 104, so that the next vertical pumping and suction movement of the piston 104 can be carried out; and after the vertical pumping and suction movement of the piston 104 is completed, the lateral movement module 126 moves to the right or left in the opposite direction, so that the piston driving mechanism 108 is separated from the piston 104.

As shown in FIG. 41, the lateral movement module 126 comprises a curved rod structure 127 and a slider structure 128; the curved rod structure 127 is located above the slider structure 128; and the curved rod structure 127 rotates to enable the slider structure 128 to move left and right, so as to drive the piston 104 and the piston driving mechanism 108 to be combined or separated. The curved rod structure 127 comprises a fixed shaft 129 and a rocking handle 130, one end of the rocking handle 130 is connected to the fixed shaft 129, the rocking handle 130 can perform the circular movement around the fixed shaft 129, and the fixed shaft 129 is driven by a direct current motor 163 to rotate. The lateral movement module 126 moves left and right mainly by means of the principle of the curved rod and slider structures, and the rocking handle 130 of the curved rod structure 127 performs the circular movement by means of the motor, so as to drive the slider structure 128 to move left and right.

The slider structure 128 is provided with a slide rail 131 with an upward opening; the other end of the rocking handle 130 is provided with a connecting rod 132; and in the process of the circular movement of the rocking handle 130, when the connecting rod 132 is inserted into the slide rail 131, the rocking handle 130 rotates to drive, by means of the connecting rod 132, the slide rail 131 to move, thereby driving the slider structure 128 to move left and right. When the rocking handle 130 performs the clockwise circular movement around the fixed shaft 129, in the process that the rocking handle rotates to the lower semicircle, the connecting rod 132 of the rocking handle 130 may slide into the slide rail 131, and in the process of the continuous clockwise circular movement, the connecting rod 132 of the rocking handle 130 may continue to move downwards and to the left at the same time; in the process of the downward movement, the connecting rod 132 also moves downwards along the slide rail 131, in the process of the leftward movement, the connecting rod 132 drives the slider structure 128 to move to the left, and when the slider structure 128 moves to the left to reach a specific position, the slider structure 128 and the piston 104 are smoothly separated. In a similar way, when the rocking handle 130 performs the anticlockwise circular movement around the fixed shaft 129, in the process that the rocking handle rotates to the lower semicircle, the connecting rod 132 of the rocking handle 130 may slide into the slide rail 131, and in the process of the continuous clockwise circular movement, the connecting rod 132 of the rocking handle 130 may continue to move downwards and to the right at the same time; in the process of the downward movement, the connecting rod 132 also moves downwards along the slide rail 131, in the process of the rightward movement, the connecting rod 132 drives the slider structure 128 to move to the right, and when the slider structure 128 moves to the right to reach a specific position, the slider structure 128 and the piston 104 are smoothly separated. Therefore, all that is needed for smoothly combining the slider structure 128 with the piston 104 is to control the rocking handle 130 to perform the clockwise circular movement of the lower semicircle (only ¼ circumference of the lower semicircle is required in this embodiment) around the fixed shaft 129 firstly, and then the pumping and suction movement of the piston 104 can be started; and after the pumping and suction movement is completed, all that is needed for smoothly separating the slider structure 128 from the piston 104 is to control the rocking handle 130 to perform the anticlockwise circular movement of the lower semicircle (only ¼ circumference of the lower semicircle is required in this embodiment) around the fixed shaft 129.

As shown in FIGS. 41 and 42, the curved rod structure 127 is provided with a bracket 133, the direct current motor 163 wrapped outside the fixed shaft 129 is in direct contact with the bracket 133, and the curved rod structure 127 is fixed above the vertical movement module 125 by means of the bracket 133. The bracket 133 is composed of a horizontal plate 134 and a vertical plate 135, the horizontal plate 134 is fixed to the vertical movement module 125, a lower end 136 of the vertical plate 135 is fixed to the slider structure 128, and an upper end 137 thereof is used to fix the fixed shaft 129 of the curved rod structure 127.

As shown in FIG. 42, a bottom surface 138 of the slider structure 128 is provided with an arc-shaped notch 139 with an opening; as shown in FIG. 40, the piston 104 comprises the piston cover 122 and the piston rod 123, and the piston cover 122 has the diameter greater than the cross section diameter of the piston rod 123; and when the slider structure 128 gets close to the piston 104, the arc-shaped notch 139 is sleeved on the piston rod 123, so that the piston 104 is combined with the piston driving mechanism 108 and moves vertically with the vertical movement module 125. The piston cover 122 has the cross section diameter obviously greater than that of the piston rod 123, and the piston cover 122 is in a shape similar to a cake structure. Since the consumable 102 is fixed in the nucleic acid extraction and detection integrated machine 101, the piston 104 of the consumable 102 is also fixed, can only perform the vertical pumping and suction movement and cannot move left and right. Therefore, after the slider structure 128 moves to the left and the arc-shaped notch 139 in the bottom surface 138 is sleeved on the piston rod 123, as long as the slider structure 128 does not retreat to the right, the piston 104 is always combined with the slider structure 128 and cannot be separated, and at this moment, the vertical movement module 125 can move vertically to drive the piston 104 to perform the pumping and suction movement; and after the pumping and suction movement is completed, the slider structure 128 moves to the right, and then the piston 104 can be separated from the slider structure 128.

As shown in FIG. 41, the lateral movement module 126 is integrally nested with the vertical movement module 125 by means of the slider structure 128 and can move left and right relative to the vertical movement module 125. The vertical movement module 125 can only move vertically and cannot move left and right; and although the lateral movement module 126 is integrally nested with the vertical movement module 125, the lateral movement module can move left and right relative to the vertical movement module 125, that is, the lateral movement module 126 can slide left and right relative to the vertical movement module 125. The slider structure 128 is provided with two bumps 140, which are respectively a first bump 401 and a second bump 402; the vertical movement module 125 is provided with two grooves 141, which are respectively a first groove 411 and a second groove 412; and when the vertical movement module 125 and the lateral movement module 126 are integrally nested and combined, the first bump 401 and the second bump 402 are embedded into the first groove 411 and the second groove respectively 412. The first bump 401, the second bump 402, the first groove 411 and the second groove 412 are all obliquely provided at an angle of 1-10 degrees with the horizontal direction, and when they are provided at a certain inclination angle, the piston driving mechanism 108 and the piston 104 can be combined and separated more easily and can fit seamlessly. Of course, the inclination angle should not be too large, the first bump, the second bump, the first groove and the second groove are just slightly inclined, and the inclination angle needs to be controlled at an angle of 1-10 degrees, preferably 2 degrees. When the lateral movement module 125 moves left and right, the first bump 401 and the second bump 402 slide left and right in the first groove 411 and the second groove 412 respectively.

As shown in FIG. 43, the vertical movement module 125 comprises a movement handle 142 and a main movement body 143, the first groove 411 and the second groove 412 are provided on the main movement body 143, the first bump 401 and the second bump 402 of the slider structure 128 can be inserted into the first groove 411 and the second groove 412 respectively from one side of the main movement body 143, and the slider structure 128 can move left and right along the first groove 411 and the second groove 412, that is, the lateral movement module 126 moves left and right relative to the vertical movement module 125. The first bump 401, the second bump 402, the first groove 411 and the second groove 412 are all obliquely provided at an angle of 2 degrees with the horizontal direction; and when the lateral movement module moves left and right, the first bump 401 and the second bump 402 slide left and right in the first groove 411 and the second groove 412 respectively. When the lateral movement module 126 moves left and right, the first bump 401 and the second bump 402 slide left and right in the first groove 411 and the second groove 412 respectively.

Preferably, a limiting mechanism 145 is arranged on a side wall 144 of the vertical movement module 125, a limiting rail 147 is arranged on a side wall 146 of the lateral movement module 126, and the limiting mechanism 145 moves left and right in the limiting rail 147 and is configured to limit the left-and-right displacement of the lateral movement module 126. In this embodiment, the limiting mechanism 145 is a screw, which can be fixed to a screw hole 148 of the side wall 144.

The limiting mechanism 145 can only move left and right in the limiting rail 147, which limits the maximum distance of the left-and-right displacement of the lateral movement module 126. Meanwhile, after the rocking handle 130 performs the clockwise circular movement of the lower semicircle around the fixed shaft 129 firstly, the lateral movement module 126 moves to the left to reach the leftmost end, the limiting mechanism 145 is located at the rightmost end 149 of the limiting rail 147 at this moment, and the slider structure 128 is smoothly combined with the piston 104; and after the rocking handle 130 performs the anticlockwise circular movement of the lower semicircle around the fixed shaft 129, the lateral movement module 126 moves to the right to reach the rightmost end, the limiting mechanism 145 is located at the leftmost end 150 of the limiting rail 147 at this moment, and the slider structure 128 is smoothly separated from the piston 104.

As shown in FIG. 45, the piston 104 and the piston driving mechanism 108 in the nucleic acid extraction and detection integrated machine 101 provided in this embodiment have four states as follows: in the first state which is the initial state, the disposable consumable 102 is placed into the corresponding recess 151 of the nucleic acid extraction and detection integrated machine 101, and the piston driving mechanism 108 is far away from the piston 104 at this moment; in the second state which is the ready state, the piston driving mechanism 108 moves downwards to get close to the piston 104; in the third state which is the working state, the rocking handle 130 is rotated clockwise, so that the piston driving mechanism 108 moves to the left to be combined with the piston 104 to enter the working state to perform the vertical pumping and suction movement of the piston 104; and in the fourth state which is the restoring state, the rocking handle 130 is rotated anticlockwise, so that the piston driving mechanism 108 moves to the right to be separated from the piston 104; and after the fourth state is completed, the piston driving mechanism 108 moves upwards to get away from the piston 104, so that the consumable 102 can be taken out conveniently.

As shown in FIG. 29, the nucleic acid extraction assembly 106 further comprises a pyrolysis bin 154, a washing bin 152 and an elution bin 153; the pyrolysis bin 154 is configured to store the samples, a pyrolysis liquid, the magnetic beads and a waste liquid generated after pyrolysis; the washing bin 152 is configured to store a washing liquid and a waste liquid generated after washing; one or more washing bins 152 are provided; the elution bin 153 is configured to store an eluent; through holes are provided in a bottom of the pyrolysis bin 154, a bottom of the washing bin 152 and a bottom of the elution bin 153; and the channel turntable 112 can be rotated to enable the micro-channel 113 to be in selective communication with the bottom through hole of the pyrolysis bin 154, the washing bin 152 or the elution bin 153, so that the reaction chamber 105 is in selective communication with the pyrolysis bin 154, the washing bin 152 or the elution bin 153. The communication mentioned in this embodiment refers to fluid communication, and the fluid can flow from one place to another and may pass through some physical structures to play a guiding role in the flow process. Passing through the physical structures generally means that the fluid passes through surfaces of the physical structures or internal spaces of the structures to passively or actively flow to another place; the passivity generally refers to the flow caused by an external force, for example, the flow under pressure. In this embodiment, it specifically means that the fluid can enter the reaction chamber 105 from other chambers of the consumable 102 and can also enter other chambers from the reaction chamber 105 and the fluid can be switched repeatedly between the different chambers. The term "selective" here means that when the reaction chamber 105 is in fluid communication with the pyrolysis bin 154, the washing bin 152 and the elution bin 153 are not in fluid communication with the reaction chamber 105; when the washing bin 152 is in fluid communication with the reaction chamber 105, the reaction chamber 105 is not in fluid communication with the pyrolysis bin 154 and the elution bin 153; when the elution bin 153 is in fluid communication with the reaction chamber 105, the reaction chamber 105 is not in fluid communication with the pyrolysis bin 154 and the washing bin 152; and that is, the reaction chamber 105 is in selective fluid communication with other chambers of the consumable 102 at the proper time.

As shown in FIGS. 30 and 31, the nucleic acid amplification assembly 107 comprises a PCR tube 155 and a PCR tube channel 156, the PCR tube 155 is detachably connected to the bottom surface 161 of the consumable 102, and the sealed connection can be realized after the connection; and after the nucleic acid extraction is completed, the channel turntable 112 is rotated to enable the micro-channel 113 to be in selective communication with the PCR tube channel 156, so that the reaction chamber 105 is in selective communication with the PCR tube 155. The PCR tube 155 of the nucleic acid amplification assembly 107 provided in this embodiment is of a detachable structure, that is, other portions of the consumable 102 are integrally formed and prepared, and a connection port 157 is reserved at the position of the PCR tube 155; the PCR tube 155 is prepared separately, meanwhile, the reagent required by a nucleic acid amplification reaction is placed in the PCR tube 155 in advance, and the PCR tube is covered with a lid 158 for sealed storage; when nucleic acid detection is required to be performed, the lid 158 of the PCR tube 155 is removed, and then the PCR tube is connected to the reserved connection port 157 of the consumable 102, and the reserved connection port 157 is further provided with a sealing ring 162, which helps achieve the sealed connection. The PCR tube 155 with the thinner wall that is prepared in advance is adopted in this embodiment, and the PCR tube 155 is connected to the consumable 102 when being used, which can well solve the problem of slow temperature rise and greatly improve the detection efficiency. In addition, the PCR tube 155 prepared separately can store the reaction reagent in advance, which is more beneficial to storage and transportation. In this embodiment, the consumable 102 further comprises an upper cover 159, a lower cover 160 and the bottom surface 161.

Embodiment 6. Nucleic Acid Extraction and Detection Integrated Machine Applicable to Consumable (Piston, Reaction Chamber and Magnetic Rod being Arranged in Sequence from Top to Bottom)

In this embodiment, the nucleic acid extraction and detection integrated machine 101 applicable to the consumable provided in Embodiment 5 is prepared according to the consumable, and meanwhile, the temperature control module for controlling the temperature of the PCR tube 155 and a fluorescence detection module for detecting the content of the nucleic acids in the PCR tube 155 are provided in the nucleic acid extraction and detection integrated machine 101.

Embodiment 7. Process of Nucleic Acid Extraction and Amplification Performed in Consumable In this embodiment, the nucleic acid extraction and amplification device-consumable 102 provided in Embodiment 5 is used to perform the nucleic acid extraction and amplification, and the process comprises the following steps:

1. the lid 158 of the PCR tube 155 containing the reagent required by the nucleic acid amplification reaction in advance is removed, and then the PCR tube is connected to the reserved connection port 157 of the consumable 102 to achieve the sealed connection;
2. adding collected samples to the pyrolysis bin 154, and at this moment, the pyrolysis bin 154 containing a mixed liquid: a pyrolysis liquid+the samples+the magnetic beads;
3. the piston 104 moving upwards to pump the mixed liquid into the reaction chamber 105;
4. the piston 104 moving downwards to press the mixed liquid back to the pyrolysis bin 154, so as to achieve first hammering of the liquid;
5. hammering the liquid repeatedly for the specified number of times;
6. the magnetic rod 103 moving upwards, the nucleic acids in the mixed liquid being adsorbed by the magnetic beads, and the magnetic beads being attracted and gathered at the bottom 111 of the reaction chamber 105 under the action of the magnetic force of the magnetic rod 103;
7. the piston 104 moving downwards to press the mixed liquid back to the pyrolysis bin 154, and the magnetic beads being still attracted inside the reaction chamber 105 at this moment;
8. the channel turntable 112 rotating by a certain angle (rotating clockwise and horizontally by 50 degrees in this embodiment) to communicate the micro-channel 113 with the washing bin 152 and the reaction chamber 105;
9. repeating actions in 2-6, and performing washing on the magnetic beads and the nucleic acids;
10. the channel turntable 112 rotating by a certain angle (rotating clockwise and horizontally by 50 degrees in this embodiment) to communicate the micro-channel 113 with the elution bin 153 and the reaction chamber 105;
11. repeating actions in 2-6, and performing elution on the magnetic beads and the nucleic acids;
12. the channel turntable 112 rotating by a certain angle (rotating clockwise and horizontally by 120 degrees in this embodiment) to communicate the micro-channel 113 with the PCR tube 155 and the reaction chamber 105;
13. the piston 104 moving downwards to extrude a mixed solution of the nucleic acids into the PCR tube 155; and
14. later, heating the PCR tube 155 by means of the temperature control module in the nucleic acid extraction and detection integrated machine, and collecting fluorescence for analysis after nucleic acid amplification.

Embodiment 8. Working Process of Nucleic Acid Extraction and Detection Integrated Machine In this embodiment, the nucleic acid extraction and detection integrated machine provided in Embodiment 6 is used to perform the nucleic acid extraction, amplification and detection, and the process comprises the following steps:

(1) installing the consumable 102 provided with the PCR tube 155 and containing samples to be tested into the recess 151 of the nucleic acid extraction and detection integrated machine 101;
(2) the piston driving mechanism 108 moving downwards and leftwards to be combined with the piston 104 in the consumable 102;
(5) the piston 104 in the consumable 102 reciprocating vertically to perform the nucleic acid extraction and amplification, and the specific process being carried out according to the steps provided in Embodiment 5;
(6) collecting fluorescence by means of the fluorescence detection module of the nucleic acid extraction and detection integrated machine 101 and performing analysis to obtain a result; and
(7) the piston driving mechanism 108 moving rightwards to be separated from the piston 104 in the consumable 102 and then moves upwards, and taking out the consumable 102 to complete working.

Embodiment 9. Comparison of Nucleic Acid Detection Effects

In this embodiment, the nucleic acid extraction and detection integrated machine provided in Embodiment 6 and the nucleic acid extraction and detection integrated machine provided in Embodiment 1 are used respectively to perform nucleic acid detection, wherein samples are $10^6$ copies/ml of novel coronavirus pseudoviruses, nucleic acids to be tested are N genes of novel coronavirus, the amplification conditions are as follows: 50 DEG C. for 10 min and 95 DEG C. for 5 min at a constant-temperature section and 95 DEG C. for 25 s and 55 DEG C for 55 s at a circulation section, the cycle number is 40, and the detection results are shown in Table 1.

TABLE 1

| | Nucleic Acid Detection Results of Different Nucleic Acid Extraction and Detection Integrated Machines | |
|---|---|---|
| S/N | Nucleic acid extraction and detection integrated machine | Measured fluorescence value |
| 1 | Embodiment 6 (piston, reaction chamber and magnetic rod being arranged vertically in sequence) | 5100 |
| 2 | Embodiment 1 | 2300 |

It can be seen from Table 1 that after the same samples are amplified by the nucleic acid extraction and detection integrated machine (No. 1) provided in Embodiment 6 of the disclosure, the measured fluorescence value is obviously higher than the detection result of the nucleic acid extraction and detection integrated machine provided in Embodiment 1, which is mainly caused by the fact that the piston, the reaction chamber and the magnetic rod of the nucleic acid extraction and amplification device (consumable) of the machine are arranged separately and vertically in sequence, the magnetic beads can be more evenly scattered in the samples in the reaction chamber and can be quickly and completely converged when being attracted by the magnetic rod, the dead corners are eliminated, the efficiency of the processes of nucleic acid adsorption, washing and elution is effectively improved, and thus the sensitivity and accuracy of the nucleic acid detection is effectively improved.

The application of the disclosure is not limited to this. For example, it can be expanded according to the scope of application in the aspect of environmental protection. Those skilled in the art can make various changes and modifications without departing from the spirit and scope of the disclosure. Therefore, the scope of protection of the disclosure shall be subject to the scope defined in the claims.

The invention claimed is:

1. A nucleic acid extraction device, comprising:
a driving component, a piston, a turntable, a plurality of chambers, a permanent magnet, and a plurality of magnetic beads;
wherein the driving component is configured to carry and drive components of the nucleic acid extraction device to work, the driving component comprises a piston driving mechanism and a worm gear and worm transmission mechanism, the worm gear and worm transmission mechanism comprises a worm, a worm shaft, a worm gear, an elastic element, and a connecting module;
the piston driving mechanism is configured to drive the piston of the nucleic acid extraction device to move vertically;
the worm gear and worm transmission mechanism is configured to drive the turntable to rotate, thereby connecting or disconnecting the plurality of chambers of the nucleic acid extraction device; and the worm gear and worm transmission mechanism is provided with the elastic element capable of resetting, which is configured to provide thrust to the worm shaft to make the worm close to the worm gear so as to eliminate a backlash;
wherein the elastic element capable of resetting is a reset spring, the reset spring is located at a first end of the worm shaft, and a second end of the worm shaft is flexibly fixed by means of an angular contact bearing;
wherein a first end of the reset spring is movably connected to the worm shaft by means of the connecting module, and the connecting module is provided with an arc-shaped recess and is in direct contact with the worm shaft by means of the arc-shaped recess;
wherein the plurality of chambers comprises a reaction chamber, the piston is configured to control a flow direction of a fluid; the reaction chamber is configured to provide a place for the magnetic beads to adsorb, wash and elute nucleic acids; the permanent magnet is configured to provide a magnetic attraction force for the magnetic beads; the permanent magnet is a magnetic rod; and the piston is located inside or outside the reaction chamber.

2. The nucleic acid extraction device according to claim 1, wherein the connecting module is made of lubricating materials, and the arc-shaped recess is provided with an arc-shaped rib which matches with an arc-shaped groove in the worm shaft.

3. The nucleic acid extraction device according to claim 1, wherein the connecting module is made of POM or Teflon materials, a second end of the reset spring is fixed to a base, and the reset spring has an elastic modulus of 0.5-1.0 N/m2.

4. A nucleic acid extraction device, comprising:
a driving component, a piston, a turntable, a plurality of chambers, a permanent magnet, and a plurality of magnetic beads;
wherein the driving component is configured to carry and drive components of the nucleic acid extraction device to work, the driving component comprises a piston driving mechanism and a worm gear and worm transmission mechanism, the worm gear and worm transmission mechanism comprises a worm, a worm shaft, a worm gear, an elastic element, and a connecting module;
the piston driving mechanism is configured to drive the piston of the nucleic acid extraction device to move vertically;
the worm gear and worm transmission mechanism is configured to drive the turntable to rotate, thereby connecting or disconnecting the plurality of chambers of the nucleic acid extraction device; and the worm gear and worm transmission mechanism is provided with the elastic element capable of resetting, which is configured to provide thrust to the worm shaft to make the worm close to the worm gear so as to eliminate a backlash,
wherein the plurality of chambers comprises a reaction chamber, the piston is configured to control a flow direction of a fluid; the reaction chamber is configured to provide a place for the magnetic beads to adsorb, wash and elute nucleic acids; the permanent magnet is configured to provide a magnetic attraction force for the magnetic beads; the permanent magnet is a magnetic rod; and the piston is located inside or outside the reaction chamber;
wherein when the piston is located inside the reaction chamber, the reaction chamber is internally provided with the piston and a hollow accommodating chamber; the hollow accommodating chamber is configured to accommodate the permanent magnet, the piston is a hollow cylinder, and the hollow cylinder in the piston has the diameter matching that of the hollow accommodating chamber, so that the piston can be sleeved outside the hollow accommodating chamber and move vertically along an outer wall of the hollow accommodating chamber; and the displacement of the piston causes the pressure change, thereby promoting the fluids to flow between the reaction chamber and other chambers.

5. The nucleic acid extraction device according to claim 4, wherein the piston driving mechanism comprises a combined movement component and a separated movement component; the combined movement component can combine the piston with a piston rod, thereby enabling the piston rod to drive the piston to move vertically; and the separated movement component prevents the piston from moving by ejecting a push rod, thereby enabling the piston to be separated from the piston rod that moves continuously; and the push rod is controlled by an electromagnet to be ejected or retracted, the push rod is ejected when the electromagnet is energized in one direction, and the push rod is retracted when the electromagnet is energized in the opposite direction.

6. The nucleic acid extraction device according to claim 5, wherein the combined movement component comprises a movement module, the movement module is configured to control the vertical movements of the piston and the piston rod, and a jacking plate is arranged below the movement module and can move vertically with the movement module; the piston rod penetrates through the jacking plate to be integrally connected with the movement module, and the jacking plate is movably sleeved on the piston rod from bottom to top; a spring is arranged below the jacking plate, when the push rod is ejected to prevent the jacking plate from moving upwards, the spring is compressed, and when the push rod is retracted, the spring is restored to push the jacking plate to return upwards; and the spring is sleeved on a slide rod, the slide rod penetrates through the jacking plate to be connected to the movement module, the jacking plate can move vertically along the slide rod, a base is arranged below the slide rod, and the base has a diameter larger than that of the spring.

7. The nucleic acid extraction device according to claim 6, wherein the combined movement component comprises a groove formed in an outer wall of the piston rod and a rib arranged on an inner wall of the piston; when the piston rod moves downwards to be inserted into the piston, the groove can match with the rib, so that the piston and the piston rod are combined; the piston is the hollow cylinder, and an upper end of the piston has a cross section diameter larger than that of a lower end and matching that of the piston rod, so that the piston rod and the upper end of the piston can be closely combined; and a cylindrical wall of the upper end of the piston is provided with a longitudinal open groove, when the piston rod is inserted into the open groove, the cross section diameter of the upper end of the piston can be increased under the effect of the open groove, and thus the piston rod can be conveniently inserted into the piston and combined with the rib by means of the groove.

8. The nucleic acid extraction device, comprising:

a driving component, a piston, a turntable, a plurality of chambers, a permanent magnet, and a plurality of magnetic beads;

wherein the driving component is configured to carry and drive components of the nucleic acid extraction device to work, the driving component comprises a piston driving mechanism and a worm gear and worm transmission mechanism, the worm gear and worm transmission mechanism comprises a worm, a worm shaft, a worm gear, an elastic element, and a connecting module;

the piston driving mechanism is configured to drive the piston of the nucleic acid extraction device to move vertically;

the worm gear and worm transmission mechanism is configured to drive the turntable to rotate, thereby connecting or disconnecting the plurality of chambers of the nucleic acid extraction device; and the worm gear and worm transmission mechanism is provided with the elastic element capable of resetting, which is configured to provide thrust to the worm shaft to make the worm close to the worm gear so as to eliminate a backlash, wherein the plurality of chambers comprises a reaction chamber, the piston is configured to control a flow direction of a fluid; the reaction chamber is configured to provide a place for the magnetic beads to adsorb, wash and elute nucleic acids; the permanent magnet is configured to provide a magnetic attraction force for the magnetic beads; the permanent magnet is a magnetic rod; and the piston is located inside or outside the reaction chamber;

wherein when the piston is located outside the reaction chamber, the permanent magnet and the piston are separately arranged; the piston is located above the reaction chamber; the permanent magnet is located below the reaction chamber; and the permanent magnet is the vertically placed magnetic rod, and the piston, the reaction chamber and the magnetic rod are arranged vertically in sequence from top to bottom.

9. The nucleic acid extraction device according to claim 8, wherein the reaction chamber is a recess with an upward opening that is provided in the center of the channel turntable; the piston moves vertically in a piston channel, and the piston channel is in communication with the reaction chamber; and a micro-channel in communication with the reaction chamber is provided in the channel turntable.

10. The nucleic acid extraction device according to claim 9, wherein the size of the lower end of the piston and the size of a lower end of the piston channel are reduced; when the piston moves downwards to the lowest position, the piston is blocked by the piston channel and cannot enter the reaction chamber; and when the piston moves downwards to the lowest position, a bottom surface of the piston and the reaction chamber in the center of the channel turntable form a sealed chamber jointly.

11. The nucleic acid extraction device according to claim 10, wherein a lower portion of the channel turntable is provided with a cross-shaped fixing element, a central rotating shaft of the fixing element is a hollow cylinder, and the hollow cylinder is a magnetic rod channel for the vertical displacement of the magnetic rod; a bottom surface of the reaction chamber is a top end of the magnetic rod channel; the lower end of the magnetic rod is provided with a magnetic rod driving mechanism for controlling the vertical displacement of the magnetic rod in the magnetic rod channel; and the upper end of the piston is provided with the piston driving mechanism for controlling the vertical displacement of the piston in the piston channel.

12. The nucleic acid extraction device according to claim 11, wherein the piston driving mechanism comprises a vertical movement module and a lateral movement module; the vertical movement module is configured to drive the piston to move vertically; the lateral movement module is configured to realize the combination or separation of the piston and the piston driving mechanism; and the vertical movement module and the lateral movement module are integrally nested and combined.

13. The nucleic acid extraction device according to claim 12, wherein the lateral movement module comprises a curved rod structure and a slider structure; the curved rod structure is located above the slider structure; the curved rod structure rotates to enable the slider structure to move left and right, so as to drive the piston and the driving mechanism to be combined or separated; the curved rod structure comprises a fixed shaft and a rocking handle, one end of the rocking handle is connected to the fixed shaft, and the rocking handle can perform the circular movement around the fixed shaft; the slider structure is provided with a slide rail with an upward opening; the other end of the rocking handle is provided with a connecting rod; and in the process of the circular movement of the rocking handle, when the connecting rod is inserted into the slide rail, the rocking handle rotates to drive, by means of the connecting rod, the slide rail to move, thereby driving the slider structure to move left and right.

14. The nucleic acid extraction device according to claim 13, wherein a bottom surface of the slider structure is provided with an arc-shaped notch with an opening; the piston comprises a top cover and the piston rod, and the top cover has the diameter greater than the cross section diameter of the piston rod; when the slider structure gets close to the piston, an open portion of the arc-shaped notch is sleeved on the piston rod, so that the piston is combined with the driving mechanism and moves vertically with the vertical movement module; and the lateral movement module is integrally nested with the vertical movement module by means of the slider structure and can move left and right relative to the vertical movement module.

15. The nucleic acid extraction device according to claim 14, wherein the slider structure is provided with two bumps, which are respectively a first bump and a second bump; the vertical movement module is provided with two grooves, which are respectively a first groove and a second groove; when the vertical movement module and the lateral movement module are integrally nested and combined, the first bump and the second bump are embedded into the first groove and the second groove respectively; and when the lateral movement module moves left and right, the first bump and the second bump slide left and right in the first groove and the second groove respectively.

16. The nucleic acid extraction device according to claim 15, wherein the nucleic acid extraction and amplification component comprises a nucleic acid extraction assembly and a nucleic acid amplification assembly; the nucleic acid extraction assembly is configured to extract the nucleic acids in samples; the piston, the reaction chamber and the permanent magnet belong to the nucleic acid extraction assembly; the nucleic acid amplification assembly is configured to amplify the nucleic acids extracted by the nucleic acid extraction assembly; the nucleic acid extraction assembly further comprises a pyrolysis bin, a washing bin and an elution bin; the pyrolysis bin is configured to store the samples, a pyrolysis liquid, the magnetic beads and a waste liquid generated after pyrolysis; the washing bin is configured to store a washing liquid and a waste liquid generated after washing; one or more washing bins are provided; the elution bin is configured to store an eluent; through holes are provided in a bottom of the pyrolysis bin, a bottom of the washing bin and a bottom of the elution bin; the micro-channel is provided in the channel turntable; and the channel turntable can be rotated to enable the micro-channel to be in selective communication with the bottom through hole of the pyrolysis bin, the washing bin or the elution bin, so that the reaction chamber is in selective communication with the pyrolysis bin, the washing bin or the elution bin.

17. The nucleic acid extraction device according to claim 16, wherein the nucleic acid amplification assembly comprises a PCR tube and a PCR tube channel; after the nucleic acid extraction is completed, the channel turntable is rotated to enable the micro-channel to be in selective communication with the PCR tube channel, so that the reaction chamber is in selective communication with the PCR tube; the PCR tube is fixedly or detachably connected to a bottom surface of the nucleic acid extraction and amplification device, and the sealed connection can be realized after the connection; and the PCR tube channel at an inlet of the PCR tube deviates from the center line of the PCR tube.

* * * * *